US00RE41895E

(19) United States
(12) Reissued Patent
Vite et al.

(10) Patent Number: US RE41,895 E
(45) Date of Reissued Patent: Oct. 26, 2010

(54) EPOTHILONE DERIVATIVES

(75) Inventors: Gregory D. Vite, Titusville, NJ (US); Soong-Hoon Kim, Lawrenceville, NJ (US); Robert M. Borzilleri, Lawrenceville, NJ (US); James A. Johnson, Lawrenceville, NJ (US)

(73) Assignee: Bristol-Myers Squibb Company, Princeton, NJ (US)

(21) Appl. No.: 12/539,496

(22) Filed: Aug. 11, 2009

Related U.S. Patent Documents

Reissue of:
(64) Patent No.: 6,605,599
Issued: Aug. 12, 2003
Appl. No.: 09/084,542
Filed: May 26, 1998

U.S. Applications:
(60) Provisional application No. 60/051,951, filed on Jul. 8, 1997, and provisional application No. 60/067,524, filed on Dec. 4, 1997.

(51) Int. Cl.

| | |
|---|---|
| ***C07D 493/04*** | (2006.01) |
| ***C07D 491/04*** | (2006.01) |
| ***C07D 413/04*** | (2006.01) |
| ***A61K 31/4184*** | (2006.01) |
| ***A61K 31/423*** | (2006.01) |
| ***A61P 35/00*** | (2006.01) |

(52) U.S. Cl. ..... 514/365; 514/450; 514/63; 514/183; 514/366; 548/202; 548/203; 548/204; 549/270; 549/71; 549/346; 549/355; 540/452; 540/462; 540/463; 540/468

(58) Field of Classification Search ..... 514/365, 514/450; 548/202, 203, 204; 549/270, 271
See application file for complete search history.

(56) References Cited

U.S. PATENT DOCUMENTS

| | | | |
|---|---|---|---|
| 4,272,525 | A | 6/1981 | Wright |
| 4,820,695 | A | 4/1989 | Debono et al. |
| 5,545,624 | A | 8/1996 | Hecker et al. |
| 5,610,178 | A | 3/1997 | Zeeck et al. |
| 5,716,939 | A | 2/1998 | Lundy et al. |
| 5,760,011 | A | 6/1998 | Jaynes et al. |
| 5,763,429 | A | 6/1998 | Bishop et al. |
| 5,786,348 | A | 7/1998 | Bishop et al. |
| 5,795,882 | A | 8/1998 | Bishop et al. |
| 5,798,345 | A | 8/1998 | Knutson et al. |
| 6,124,453 | A | 9/2000 | Fehr et al. |
| 6,194,181 | B1 | 2/2001 | Hofmann et al. |
| 6,204,388 | B1 | 3/2001 | Danishefsky et al. |
| 6,211,412 | B1 | 4/2001 | Georg et al. |
| 6,242,469 | B1 | 6/2001 | Danishefsky et al. |
| 6,316,630 | B1 | 11/2001 | Danishefsky et al. |
| 6,365,749 | B1 | 4/2002 | Kim et al. |
| 6,369,234 | B1 | 4/2002 | Danishefsky et al. |
| 6,380,394 | B1 | 4/2002 | Nicolaou et al. |
| 6,387,927 | B1 | 5/2002 | Altmann et al. |
| 6,441,186 | B1 | 8/2002 | Nicolaou et al. |
| 6,518,421 | B1 | 2/2003 | Li et al. |
| 6,576,651 | B2 | 6/2003 | Bandyopadhyay et al. |
| 6,605,599 | B1 | 8/2003 | Vite et al. |
| 6,656,961 | B2 | 12/2003 | Danishefsky et al. |
| 6,670,384 | B2 | 12/2003 | Bandyopadhyay et al. |
| 6,686,380 | B2 | 2/2004 | Lee |
| 6,689,802 | B2 | 2/2004 | DiMarco et al. |
| 6,867,305 | B2 | 3/2005 | Danishefsky et al. |
| 7,022,330 | B2 | 4/2006 | Bandyopadhyay et al. |
| 7,125,893 | B1 | 10/2006 | Klar et al. |
| 7,125,899 | B2 | 10/2006 | Vite et al. |
| 7,241,755 | B2 | 7/2007 | Vite et al. |
| 2003/0073677 | A1 | 4/2003 | Lee |
| 2007/0255055 | A1 | 11/2007 | Vite et al. |

FOREIGN PATENT DOCUMENTS

| | | |
|---|---|---|
| DE | 4138042.8 | 5/1993 |
| DE | 4316836.1 | 11/1994 |
| DE | 19542986.9 | 5/1997 |
| DE | 19636343.8 | 10/1997 |
| DE | 19639456.2 | 3/1998 |
| DE | 19645361.5 | 4/1998 |
| DE | 19645362.3 | 4/1998 |
| DE | 19647580.5 | 5/1998 |
| DE | 19701758.4 | 7/1998 |
| DE | 19707505.3 | 9/1998 |
| DE | 19713970 | * 10/1998 |
| DE | 19713970.1 | 10/1998 |
| DE | 19720312 | * 11/1998 |
| DE | 19821954 | * 11/1998 |
| DE | 19720312.4 | 11/1998 |
| DE | 19821954.7 | 11/1998 |
| DE | 19726627 | * 12/1998 |
| DE | 19726627.4 | 12/1998 |
| EP | 0 103 465 | 3/1984 |
| EP | 0 512 779 | 11/1992 |
| EP | 0 586 738 | 3/1994 |
| EP | 0 606 747 | 7/1994 |

(Continued)

OTHER PUBLICATIONS

U.S. Appl. No. 08/856,533, filed May 14, 1997, Nicolaou et al.

(Continued)

*Primary Examiner*—Bruck Kifle
(74) *Attorney, Agent, or Firm*—McDonnell, Boehnen Hulbert & Berghoff LLP

(57) ABSTRACT

The present invention relates to epothilone derivatives, having the following formula in which the variables G, W, Q, X, Y, $B_1$, $B_2$, $Z_1$, $Z_2$, and $R_1$–$R_7$ are as defined herein, methods for the preparation of the derivatives and intermediates thereof.

34 Claims, No Drawings

FOREIGN PATENT DOCUMENTS

| | | |
|---|---|---|
| EP | 0 778 283 | 6/1997 |
| EP | 879 605 | * 11/1998 |
| EP | 0 879 605 | 11/1998 |
| JP | 3101679 | 4/1991 |
| WO | WO 92/19247 | 11/1992 |
| WO | WO 93/10121 | 5/1993 |
| WO | WO 94/13324 | 6/1994 |
| WO | WO 94/21657 | 9/1994 |
| WO | WO 95/02594 | 1/1995 |
| WO | WO 96/09312 | 3/1996 |
| WO | WO 96/11398 | 4/1996 |
| WO | WO 96/26182 | 8/1996 |
| WO | WO 97/19086 | 5/1997 |
| WO | WO 97/19088 | 5/1997 |
| WO | WO 98/08849 | 3/1998 |
| WO | WO 98/22461 | 5/1998 |
| WO | WO 98/22462 | 5/1998 |
| WO | WO 98/24427 | 6/1998 |
| WO | WO 98/25929 | 6/1998 |
| WO | WO 98/31892 | 9/1998 |
| WO | WO 98/47891 | 10/1998 |
| WO | WO 99/01124 | 1/1999 |
| WO | WO 99/03848 | 1/1999 |
| WO | WO 99/07692 | 2/1999 |
| WO | WO 99/39694 | 8/1999 |
| WO | WO 99/42602 | 8/1999 |
| WO | WO 99/43320 | 9/1999 |
| WO | WO 99/43653 | 9/1999 |
| WO | WO 99/67252 | 12/1999 |
| WO | WO 00/00485 | 1/2000 |
| WO | WO 00/31247 | 6/2000 |
| WO | WO 00/37473 | 6/2000 |
| WO | WO 00/49021 | 8/2000 |
| WO | WO 0066589 | 11/2000 |

OTHER PUBLICATIONS

U.S. Appl. No. 60/032864, filed Dec. 12, 1996, Nicolaou et al.

Information concerning inactivities of certain compounds cited Mar. 26, 1998.

Altmann et al., "Epothilones and Related Structures—A New Class of Microtubule Inhibitors With Patent In Vivo Antitumor Activity," *Biochim. Biophys Acta*,, 1470:M79–M81 (2000).

Balasubramanian et al., Recent Developments in Cancer Cytotoxics, Annual Reports in Medicinal Chemistry, vol. 33, pp. 151–162, 1998.

Balog, et al., Stereoselective Synthesis and Evaluation of Compounds in the 8–Desmethylepothilone A Series: Some Surprising Observations Regarding Their Chemical and Biological Properties, *Tetrahedron Letters*, vol. 38, No. 26, pp. 4529–4532, (1997).

Balog et al., 1996, "Total Synthesis of (–)–Epothilone A", *Angew. Chem. Int. Ed. Engl.*, 35(23–24):2801–2803.

Banker et al., Modern Pharmaceutics, Third Edition, Revised and Expanded, p. 908, 1996.

Bennett et al., Cecil Textbook of Medicine, 20$^{th}$ Edition, Index, 1996.

Bertinato P., et al., 1996, "Studies Toward a Synthesis of Epothilone A; Stereocontrolled Assembly of the Acyl Region and Models for Macrocycilization", *J. Org. Chem.*, 61(23):8000–8001.

Bertini et al., 1970, "Alkenes from Expoxides by Reductive Elimination with Magnesium Bromide–Magnesium Amaigam", *Chem. Commun.*, 144.

Bollag D., 1997, "Epothilones: Novel Microtubule–Stabilising Agents", *Expert Opin. Invest. Drugs*, 6(7):867–873.

Bollag D., et al., 1995, "Epothilone, A New Structural Class of Microtubule Stablizer", Abstract, *Proc. Am. Assoc. Cancer Res.*36(86): Meet. 454.

Bollag et al., 1995, "Epothilones, A New Class of Microtubule–stabilizing Agents with a Taxol–like Mechanism of Action", *Cancer Res.*, 55, No. 11, 2325–2333.

Chemical & Engineering News, 1996, "Epothilone Epiphany: Total Synthesis", 74( 52):24–26.

Chemical & Engineering News, 1997, "First Total Synthesis of Epothilone B", 75(13):23.

Chemical & Engineering News, 1997, "Solid–Phase Epothilone Synthesis Used to Create Analog Library", 75(20):33.

Claus et al., 1997, "Synthesis of the C1–C9 Segment of Epothilons", Tetrahedron Lett., 38(8):1359–1362.

De Brabander et al., 1997 "Iowards a Synthesis of Epothilone A: Rapid Assembly of the C1–C6 and C7–C12 Fragments", *Synlett*, 7: 824–826.

Fujisawa et al., 1974, "Deoxygenation of Epoxides to Olefins with $FeCI_3$—BuLi System", *Chem. Lett.*, 883–886.

Fujisawa et al., 1978, "Reductive Coupling of Carbonyl Compounds to Olefins by Tungsten Hexachloride–Lithium Aluminum Hydride and Some Tungsten and Molybdenum Carbonyls", *J. Org. Chem.*, 43(12): 2477–2479.

Gabriel T. and Wessjohann, L., 1997"The Chromium–Reformatsky Reaction; Asymmetric Synthesis of the Aldol Fragment of the Cytotoxic Epothilons from 3–(2–Bromoacyl)–2–Oxazolidinones", *Tetrahedron Lett.*, 38(8):1363–1366.

Gerth K., et al., 1996, "Epothilons A and B: Antifungal and Cytotoxic Compounds from *Sorangiusm celluiosum* (Myxobacteria) Production Physico–chemical and Biological Properties", *J. Antibiotics*, 49(6): 560–563.

Gladysz et al., 1976. "Deoxygenation of Epoxides by Metal Atom Cocondensation", *J. Org. Chem.*, 41(22): 3647–3648.

Hofle et al., 1996, "Epothilone A and B—Novel 16–Membered Macrolides with Cytotoxic Activity: Isolation, Crystal Structure, and Conformation in Solution", *Angew. Chem. Int. Ed Engl.*, 35(13–14):1567–1569.

Hofle et al., 1999, "N–Oxidation of Epothilone A–C and O–Acyl Rearrangement to C–19 and C–21—Substituted Epothilones", *Angew. Chem.* Int. Ed., 38(13/14):1971–1974.

Inokuchi et al., 1992, "Opening of Epoxides to Olefins or Halohydrins with Vanadium(II)—Tetrahydrofuran or Vanadium(III)—Tetrahydrofuran Complexes", *Synlett*, No. 6, 510–512.

Kowalski et al., 1997, "Activities of the Microtubule–stabilizing Agents Epothilones A and B with Purified Tubulin and in Cells Resistant to Paclitaxel (Taxol®)" *J. Biol. Chem.*, 272(4):2534–2541.

Kupchan et al., 1971, "Reductive Elimination of Epoxides to Olefins with Zinc–Copper Couple", *J. Org. Chem.*, 36(9):1187–1190.

Marshall A., "Total Synthesis of Epothilone", Nature Biotechnology, vol. 15, No. 3, 205 (1997).

Martin et al., 1984, "Epoxides as Alkene Protecting Groups. A Mild and Efficient Deoxygenation", *Tetrahedron Letters*, 25(3):251–254.

McMurry et al, 1975, "Reduction of Epoxides to Olefins with Low Valent Titanium", *J. Org. Chem.*, 40(17):2555–2556.

McMurry et al., 1978, "Some Deoxygenation Reactons with Low–Valent Titanium ($TiC_3/LiAlH_4$)", *J. Org. Chem.*, 43(17):3249–3254.
Meng D., et al., "Remote Effects in Macrolide Formation Through Ring–Forming Olefin Metathesis: An Application to the Synthesis of Fully Active Epothilone Congeners", *J. Am. Chem. Soc.*, vol. 119, No. 11, 2733–2734 (1997).
Meng D., et al., "Studies Toward a Synthesis of Epothilone A: Use of Hydropyran Templates for the Managment of Acyclic Stereochemical Relationships", *J. Org. Chem.*, vol. 61, No. 23, 7998–7999 (1996).
Meng D., et al., "Total Synthesis of Epothilones A and B", *J. Am. Chem. Soc.*, vol. 119, No. 42, 10073–10092 (1997).
Mensching, S. and Kalesse, M., "Generaton of Thiazoles by Column Dehydrogenation of Thiazolidines with $MnO_2$", *J. Prakat. Chem.*, vol. 339, No. 1, 96–97 (1997).
Mulzer, J. and Mantoulidis, A., "Synthesis of the C(1)–C(9) Segment of the Cytotoxic Macrolides Epothilon A and B", *Tetrahedron Lett.*, vol. 37 No. 51, 9179–9182 (1996).
Nicolaou et al., "Chemistry and Biology of Epothilones", *Angew. Chem. Int. Ed.*, 37, pp. 2014–2045, 1998.
Nicolaou et al., "Designed Epothilones: Combinatorial Synthesis, Tubulin Assembly Properties, and Cytotoxic Action Against Taxol–Resistant Tumor Cells", *Angew. Chem. Int. Ed. Engl.*, vol. 36, No. 19, 2097–2103 (1997).
Nicolaou et al., "Total Synthesis of Epothilone E and Analogs with Modified Side Chains Through the Stille Coupling Reaction", *Angew Chem. Int. Ed.*, 37, pp. 84–87, 1998.
Nicolaou K. C., et al., 1996, "An Approach to Epothilones Based on Olefin Metathesis", *Angew. Chem. Int. Ed. Engl.*, 35(20):2399–2401.
Nicolaou K. C., et al., 1998, "Synthesis and Biological Properties of C12, 13–Cyclopropylepothilone A and Related Epothilones", *Chemistry & Biology*, 5(7): 365–372.
Nicolaou K., et al., 1997, "Total Synthesis of Epothilone E and Related Side—chain Modified Analogues Via a Stille Coupling Based Strategy", Bloorg. Med. Chem., 7(5): 665–697.
Nicolaou K., et al., 1999, "Chemistry, Biology and Medicine of Selected Tubulin Polymerizing Agents", Pure Appl. Chem., 71(6): 989–997.
Nicolaou K.C. et al., 1997, "Synthesis of Epothilones A and B in Solid And Solution Phase", Nature, 387: 268–272.
Nicolaou K.C. et al., 1997, "Synthesis of Epothilones A and B in Solid and Solution Phase", (Correction to Nature 387, 268–272 (1997)), Nature 390, 100.
Nicolaou K.C. et al., 1997, "The Olefin Metathesis Approach to Epothilone A and its Analogues", J. Am. Chem. Soc., 119(34): 7960–7973.
Nicolaou K.C. et al., 1997, "Total Syntheses of Epothilones A and B via a Macrolactonization–Based Strategy", J. Am. Chem. Soc., 1199(34): 7974–7991.
Nicolaou K. C. et al., 1997, "Total Synthesis of Epothilone A: The Macrolactonization Approach", Angew. Chem. Int. Ed. Engl., 36(5):525–527.
Raucher, S., et al., 1986, "Total Synthesis of (+)–Dihydrocostunolide via Tandem Cope–Claisen Rearrangement", J. Org. Chem., 51(26): 5503–5505.
Sato M. et al., 1982, "Reduction of Organic Compounds with Low–Valent Nioblum ($NbCL_5/NaAlH_4$)", Chem. Letters, 157–160.
Schinzer D. et al., 1997, "Total Synthesis of (–)–Epothilone A", Angew. Chem. Int. Ed. Engl., 36(5):523–524.
Schinzer D., et al., 1996, "Studies Towards the Synthesis of Epothilones: Asymmetric Synthesis of the Key Fragments", Chem. Eur. J., 2(22): 1477–1482.
Schinzer D., et al., "Total Synthesis of (–)–Epothilone A", Chem. Eur. J., 5(9): 2483–2491, (1999).
Schinzer D., et al., "Synthesis of (–)–Epothilone B", Chem. Eur. J., 5(9): 2492–2500, (1999).
Schobert R., et al., 1990, "Reduction and Isomerization of Oxiranes and—Diazoketones by Various Early Transition Metallocenes", Synlett, 8: 465–466.
Sharpless K.B., et al., 1972, "Lower Valent Tungsten Halides. A New Class of Reagents for Deoxygenation of Organic Molecules", J. Amer. Chem. Soc., 94(18): 6538–6540.
Su D.–S. et al., 1997, "Total Synthesis of (–)–Epothilone B: An Extension of the Suzuki Coupling Method and Insights into Structure–Activity Realationships of the Epothilones", Angew. Chem. Int. Ed. Engl., 36(7): 757–759.
Su D.–S., et al., 1997, "Structure–Activity Relationships of the Epothilones and the First In Vivo Comparison with Paclitaxel", Angew. Chem. Int. Ed. Engl., 36(19):2093–2096.
Taylor and Haley, J., 1997, "Towards the Synthesis of Epothilone A: Enantioselective Preparation of the Thiazole Sidechain and Macrocyclic Ring Closure", Tetrahedron Lett., 38(12):2061–2064.
Victory, S.F., et al., 1996, "Relative Stereochemistry and Solution Conformation of the Novel Pacilitaxel–Like Antimitotic Agent Epothilone A", Bloorg. Med. Chem. Letts., 6(7):893–898.
Winkler J. D. et al., 1996, "A Model For The Taxol (Pacitaxel)/Epothilone Pharmacophore", Bloorg. Med. Chem. Letts., 6(24): 2963–2966.
Yang Z., et al., 1997, "Total Synthesis of Epothilone A: The Olefin Metathesis Approach", Angew. Chem. Int. Ed. Engl., 36(1/2): 166–168.
Gerth, et al., "The Soraphens: A Family of Novel Antifungal Compounds From *Sorangium callulosum* (Myxobacteria)", The Journal of Antibiotics, 1993, vol.47, No. 1, pp.23–31.
Schummer et al., "Chemical Modification of the Antifungal Macolide Soraphen A1α:Cleavage and Reconstruction of the Lactone Bond: Chemical Modification of Soraphen A," in Antibiotics and Antiviral Compounds—Chemical Synthesis and Modifications, Krohn et al. (Eds.), VCH Verlagsgesellschaft, 1993, pp. 133–141.
"Partial Synthesis of Soraphen Analogs in the ring segment C–3/O–17", Dissertation of Thorsten Jahn of Schleswig, 1995, (English translation and original German dissertation enclosed).
Hunt, "Discovery of Ixabepilone", Mol. Cancer Ther., Feb. 2009, 8(2):275–281.
Borzilleri, et al., "A Novel Application of a Pd(0)–Catalyzed Nucleophilic Substitution Reaction to the Regio– and Stereoselective Synthesis of Lactam Analogues of the Epothilone Natural Products", J. Am. Chem. Soc., 2000, 122:8890–8897.
Information concerning inactivity of cetain compounds dated 1998 and 1999.
U.S. Appl. No. 08/923,869, Nicolaou et al., filed Sep. 4, 1997.*

* cited by examiner

EPOTHILONE DERIVATIVES

Matter enclosed in heavy brackets [ ] appears in the original patent but forms no part of this reissue specification; matter printed in italics indicates the additions made by reissue.

*Notice: More than one reissue application has been filed for the reissue of U.S. Pat. No. 6,605,599. The reissue applications are U.S. Ser. No. 12/539,492, filed Aug. 11, 2009; U.S. Ser. No. 12/539,496, filed Aug. 11, 2009 (the present reissue application); and U.S. Ser. No. 12/539,498, filed Aug. 11, 2009. All three are reissue applications of U.S. Pat. No. 6,605,599.*

FIELD OF THE INVENTION

This application claims benefit to U.S. Provisional Application Serial No. 60/051,951, filed Jul. 8, 1997 and claims benefit to U.S. Provisional Application Serial No. 60/067,524, filed Dec. 4, 1997.

The present invention relates to epothilone derivatives, methods for the preparation of the derivatives and intermediates therefor.

BACKGROUND OF THE INVENTION

Epothilones are macrolide compounds which find utility in the pharmaceutical field. For example, Epothilones A and B having the structures:

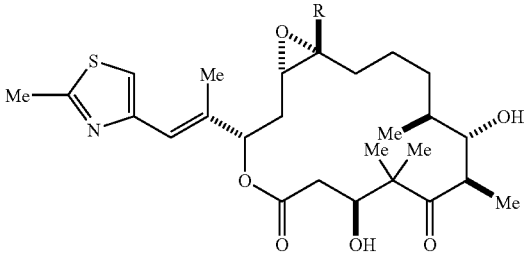

I Epothilone A R = H
II Epothilone B R = Me have been found to exert microtubule-stabilizing effects similar to TAXOL and hence cytotoxic activity against rapidly proliferating cells, such as, tumor cells or other hyperproliferative cellular disease, see Angew. Chem. Int. Ed. Engl., 1996, 35, No. 13/14.

SUMMARY OF THE INVENTION

The present invention relates to compounds of the formula

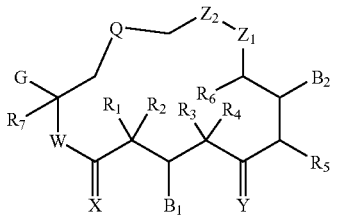

V

Q is selected from the group consisting of

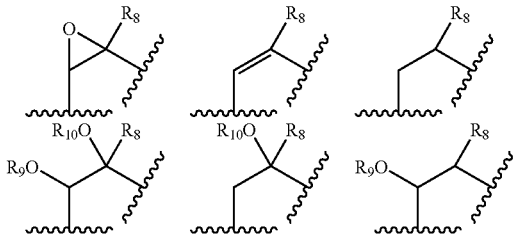

G is selected from the group consisting of alkyl, substituted alkyl, substituted or unsubstituted aryl, heterocyclo,

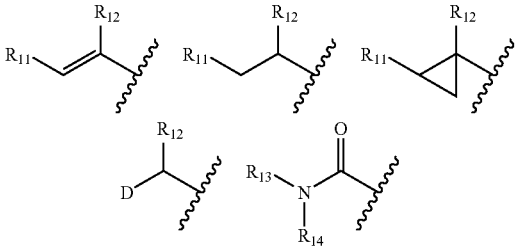

W is O or $NR_{15}$;

X is O or H, H;

Y is selected from the group consisting of O; H, $OR_{16}$; $OR_{17}$, $OR_{17}$; $NOR_{18}$; H, $NOR_{19}$; H, $NR_{20}R_{21}$; H, H; or $CHR_{22}$; $OR_{17}$ $OR_{17}$ can be a cyclic ketal;

$Z_1$, and $Z_2$ are selected from the group consisting of $CH_2$, O, $NR_{23}$, S, or $SO_2$, wherein only one of $Z_1$ and $Z_2$ can be a heteroatom;

$B_1$ and $B_2$ are selected from the group consisting of $OR_{24}$, or $OCOR_{25}$, or $O_2CNR_{26}R_{27}$; when $B_1$ is OH and Y is OH, H they can form a six-membered ring ketal or acetal;

D is selected from the group consisting of $NR_{28}R_{29}$, $NR_{30}COR_{31}$ or saturated heterocycle;

$R_1$, $R_2$, $R_3$, $R_4$, $R_5$, $R_6$, $R_7$, $R_{13}$, $R_{14}$, $R_{18}$, $R_{19}$, $R_{20}$, $R_{21}$, $R_{22}$, $R_{26}$, and $R_{27}$ are selected from the group H, alkyl, substituted alkyl, or aryl and when $R_1$ and $R_2$ are alkyl can be joined to form a cycloalkyl; $R_3$ and $R_4$ are alkyl can be joined to form a cycloalkyl;

$R_9$, $R_{10}$, $R_{16}$, $R_{17}$, $R_{25}$, and $R_{31}$ are selected from the group H, alkyl, or substituted alkyl;

$R_8$, $R_{11}$, $R_{12}$, $R_{28}$, $R_{30}$, $R_{32}$, $R_{33}$, and $R_{30}$ are selected from the group consisting of H, alkyl, substituted alkyl, aryl, substituted aryl, cycloalkyl, or heterocyclo;

$R_{15}$, $R_{23}$ and $R_{29}$ are selected from the group consisting of H, alkyl, substituted alkyl, aryl, substituted aryl, cycloalkyl, heterocyclo, $R_{32}C{=}O$, $R_{33}SO_2$, hydroxy, O-alkyl or O-substituted alkyl;

and any salts, solvates or hydrates thereof.

Proviso

The present invention does not include compounds of formula V wherein

W and X are both O; and $R_1$, $R_2$, $R_7$, are H; and $R_3$, $R_4$, $R_6$, are methyl; and $R_8$, is H or methyl; and $Z_1$, and $Z_2$, are $CH_2$; and G is 1-methyl-2-(substituted-4-thiazolyl)ethenyl;

Q is as defined above.

DETAILED DESCRIPTION OF THE INVENTION

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkyoxy, heterocylooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl; substituted alkyl, halo, trifluoromethoxy, trifluoromethyl, hydroxy, alkoxy, cycloalkyloxy, heterocylooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl.

The term "cycloalkyl" refers to optionally substituted, saturated cyclic hydrocarbon ring systems, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b] pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl groups as described above or one or more groups described above as alkyl substituents. Also included are smaller heterocyclos, such as, epoxides and aziridines.

The term "heteroatoms" shall include oxygen, sulfur and nitrogen.

The compounds of formula V may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be obtained, for example, by exchanging the carboxylic acid protons, if they contain a carboxylic acid, in compounds of formula V with the desired ion in a medium in which the salt precipitates or in an aqueous medium followed by evaporation. Other salts can be formed as known to those skilled in the art.

The compounds for formula V form salts with a variety of organic and inorganic acids. Such salts include those formed with hydrogen chloride, hydrogen bromide, methanesulfonic acid, hydroxyethanesulfonic acid, sulfuric acid, acetic acid, trifluoroacetic acid, maleic acid, benzenesulfonic acid, toluenesulfonic acid and various others (e.g., nitrates, phosphates, borates, tartrates, citrates, succinates, benzoates, ascorbates, salicylates and the like). Such salts are formed by reacting a compound of formula V in an equivalent amount of the acid in a medium in which the salt precipitates or in an aqueous medium followed by evaporation.

In addition, zwitterions ("inner salts") are formed.

Compounds of the formula V may also have prodrug forms. Any compound that will be converted in vivo to provide the bioactive agent (i.e., the compound for formula V) is a prodrug within the scope and spirit of the invention.

For example compounds of the formula V may form a carboxylate ester moiety. The carboxylate esters are conveniently formed by esterifying any of the carboxylic acid functionalities found on the disclosed ring structure(s).

Various forms of prodrugs are well known in the art. For examples of such prodrug derivatives, see:

a) Design of Prodrugs, edited by H. Bundgaard, (Elsevier, 1985) and Methods in Enzymology, Vol.42, p.309–396, edited by K. Widder, et al. (Acamedic Press, 1985);

b) A Textbook of Drug Design and Development, edited by Krosgaard-Larsen and H. Bundgaard, Chapter 5, "Design and Application of Prodrugs," by H. Bundgaard, p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Phar Bull, 32, 692 (1984).

It should further be understood that solvates (e.g., hydrates) of the compounds of formula V are also within the scope of the present invention. Methods of solvation are generally known in the art.

Use and Utility

The compounds of formula V are microtubule-stabilizing agents. They are thus useful in the treatment of a variety of cancers or other abnormal proliferative diseases, including (but not limited to) the following;

carcinoma, including that of the bladder, breast, colon, kidney, liver, lung, ovary, pancreas, stomach, cervix, thyroid and skin; including squamous cell carcinoma;

hematopoietic tumors of lymphoid lineage, including leukemia, acute lymphocytic leukemia, acute lymphoblastic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

tumors of the central and peripheral nervous system, including astrocytoma, neuroblastoma, glioma, and schwannomas;

tumors of mesenchymal origin, including fibrosarcoma, rhabdomyosarcoma, and osteosarcoma; and other tumors including melanoma, xenoderma, pigmentosum, keratoactanthoma, seminoma, thyroid follicular cancer and teratocarcinoma.

Compounds of formula V may also inhibit tumor angiogenesis, thereby affecting abnormal cellular proliferation. Such anti-angiogenesis properties of the compounds of formula V may also be useful in the treatment of certain forms of blindness related to retinal vascularization, arthritis, especially inflammatory arthritis, multiple sclerosis, restinosis and psoriasis.

Compounds of formula V may induce or inhibit apoptosis, a physiological cell death process critical for normal development and homeostasis. Alterations of apoptotic pathways contribute to the pathogenesis of a variety of human diseases. Compounds of formula V, as modulators of apoptosis, will be useful in the treatment of a variety of human diseases with aberrations in apoptosis including cancer (particularly, but not limited to follicular lymphomas, carcinomas with p53 mutations, hormone dependent rumors of the breast, prostrate and ovary, and precancerous lesions such as familial adenomatous polyposis), viral infections (including but not limited to herpesvirus, poxvirus, Epstein-Barr virus, Sindbis virus and adenovirus), autoimmune diseases (including but not limited to systemic lupus erythematosus, immune mediated glomerulonephritis, rheumatoid arthritis, psoriasis, inflammatory bowel diseases and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including but not limited to chronic anemia and aplastic anemia), degenerative diseases of the musculoskeletal system (including but not limited to osteoporosis and arthritis), aspirin-sensitive rhinosinusitis, cystic fibrosis, multiple sclerosis, kidney diseases, and cancer pain.

The compounds of this invention are also useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula V can be used sequentially with known anticancer or cytotoxic agents and treatment, including radiation when a combination formulation is inappropriate. Especially useful are cytotoxic drug combinations wherein the second drug chosen acts in a different phase of the cell cycle, e.g. S phase, than the present compounds of formula V which exert their effects at the $G_2$-M phase.

e.g.

Thymidilate Synthase Inhibitors,
DNA Cross Linking Agents
Topoisomerase I and II Inhibitors
DNA Alkylating Agents
Ribonucleoside Reductase Inhibitors
Cytotoxic Factors e.g. TNF-alpha or
Growth factor inhibitors e.g. HER 2 receptor MAB's The present compounds may exist as multiple optical, geometric, and stereoisomers. Included within the present invention are all such isomers and mixtures thereof.

The compounds of this invention can be formulated with a pharmaceutical vehicle or diluent for oral, intravenous or subcutaneous administration. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds are administered in a dosage range of about 0.05 to 200 mg/kg/day, preferably less than 100 mg/kg/day, in a single dose or in 2 to 4 divided doses.

Preferred Compounds
Especially preferred compounds of formula V are those wherein —Q is —
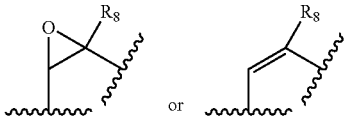
X is O
Y is O
$Z_1$ and $Z_2$ are $CH_2$ and
W is $NR_{15}$.
Method of Preparation
Compounds of formula V are prepared by the following schemes.
Scheme 1
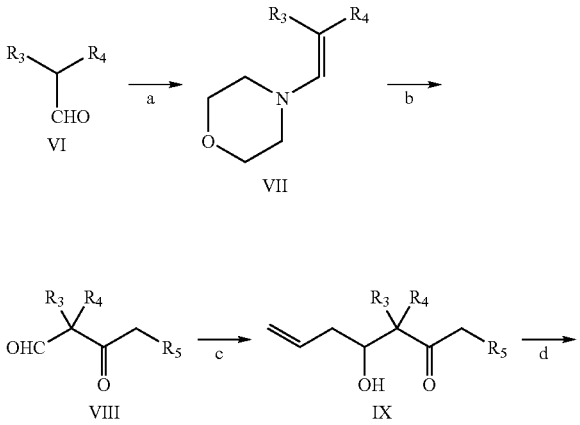
-continued
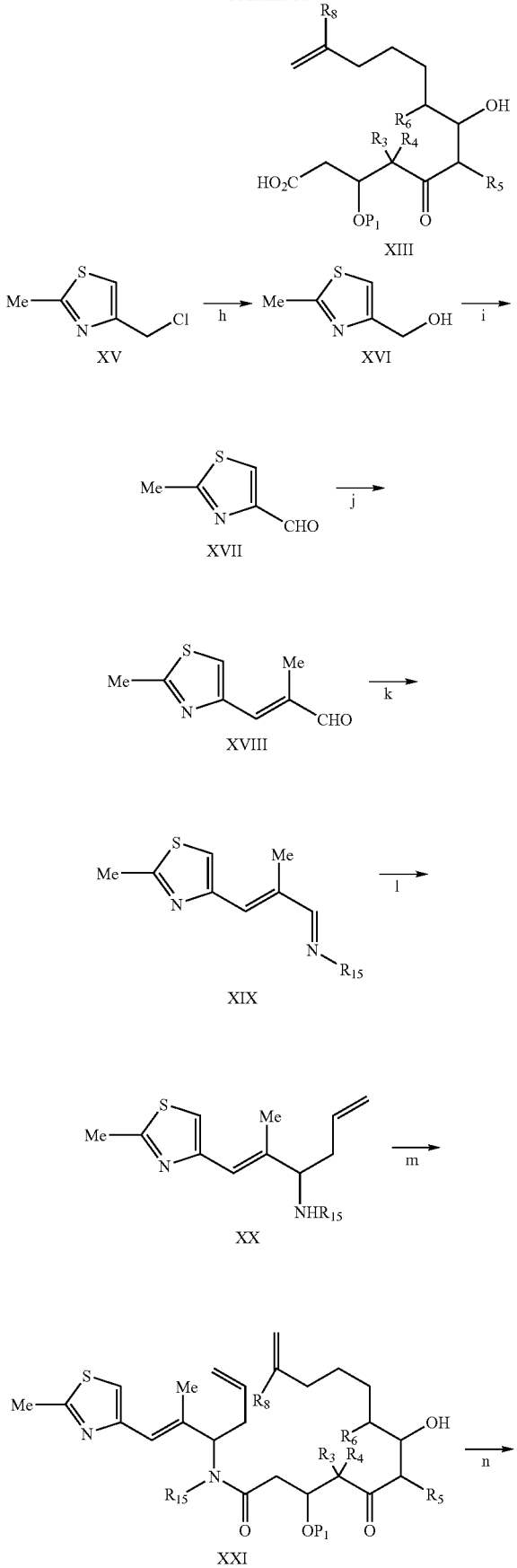

-continued

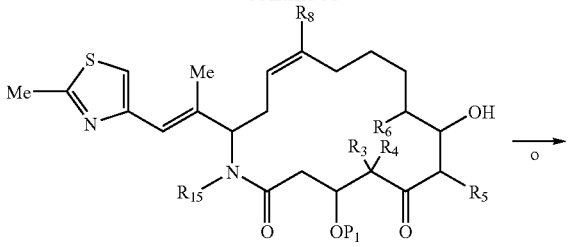

XXII

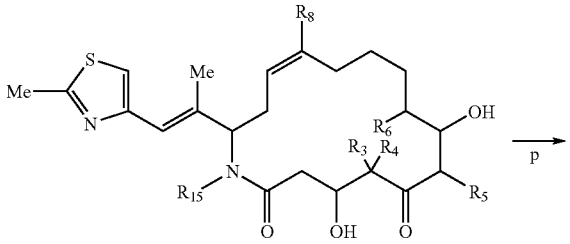

V (Q is ethylene group)

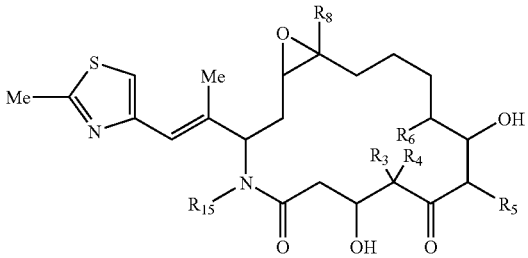

V (Q is oxirane group)

wherein $R_3$, $R_4$, $R_5$, $R_6$, $R_8$ and $R_{15}$ are as above and $P_1$ is an oxygen protecting group.

Compounds of formula V where W is $NR_{15}$ and X is O can be prepared as outlined in Scheme 1. A compound of formula XII, where $P_1$ is an oxygen protecting group such as t-butyldimethylsilyl, can be prepared from a compound of formula VI by known methods (i.e., Nicolaou, K. C, et al., Angew. Chem. Int. Ed. Engl., (1997) 36, 166–168). Aldol reaction of a compound of formula XII and a compound of formula XIV provides a compound of formula XIII. The compound of formula XIV can be prepared by known methods (i.e., Schinzer, D., et al., Eur. Chem. Chron., (1996) 1, 7–10). An aldehyde of formula XVIII can be prepared from a compound of formula XV as shown in Scheme 1 or by using known methods (i.e., Taylor, R. E., et al., Tetrahedron Lett., (1997), 38, 2061–2064). A compound of formula XIX can be prepared from a compound XVIII by treatment with an amine using dehydrating conditions such as catalytic p-toluenesulfonic acid and azeotropic removal of water. A compound of formula XX can be prepared from a compound of formula XIX by treatment with an allylating reagent such as allylmagnesium bromide. A compound of formula XXI can be prepared from compounds of formulas XIII and XX, by standard amide bond coupling agents (i.e., DCC, BOP, EDC/HOBT, PyBrOP). A compound of formula XXII can be prepared from a compound of formula XXI by ring-closing metathesis using either the Grubbs ($RuCl_2$(=CHPh)$(PCY_3)_2$; see Grubbs, R. H., et al, Angew. Chem. Int. Ed. Engl.; (1995) 34, 2039) or Schrock catalysts (Sec Schrock, R. R., et al., J. Am. Chem. Soc., (1990) 112, 3875). Deprotection of a compound of formula XXI using, for example when $P_1$ is a t-butyldimethylsily group, hydrogen fluoride in acetronitrile or tetra-n-butyl ammonium fluoride in THF provides a compound of formula V where Q is an ethylene group, W is $NR_{15}$, X is O, an $R_3$, $R_4$, $R_5$, $R_6$ are defined as described above. Regioselective epoxidation of a compound of formula V where Q is an ethylene group using dimethyldioxirane provides a compound of formula V where Q is an oxirane group, W is $NR_{15}$, X is O, and $R_3$, $R_5$, $R_{15}$ are defined as described above.

Scheme 2

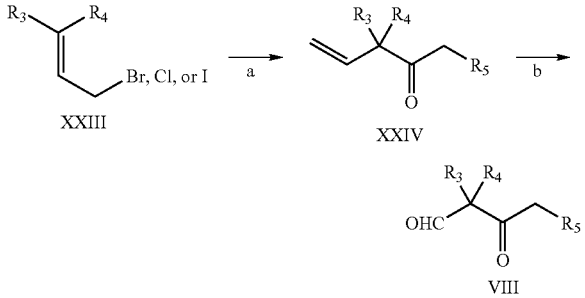

Alternatively, a compound of formula VIII can be prepared by reaction of a compound of formula XXIII with magnesium and an acid chloride ($R_5CH_2COCl$) to give a compound of formula XXIV (See for example: Heathcock, C; et. al., J. Org. Chem., 1990, 55, 1114–1117), followed by ozononolysis to give a compound of formula VIII as shown in Scheme 2.

Scheme 3

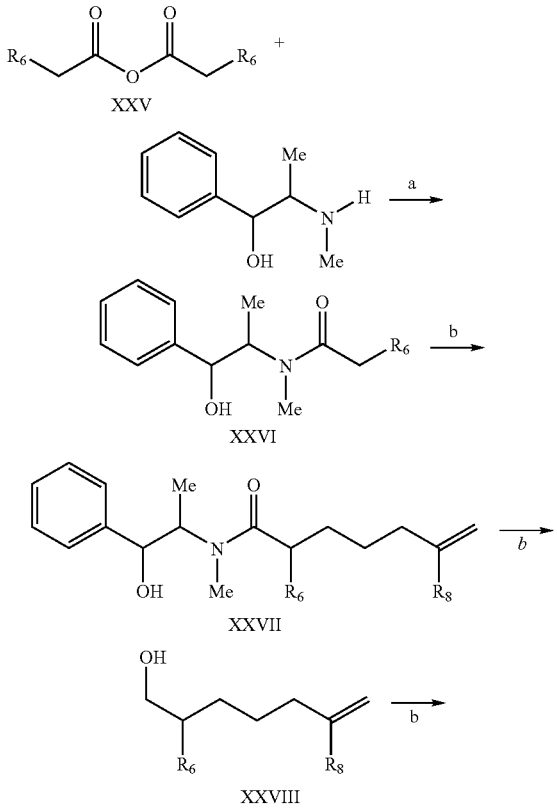

-continued

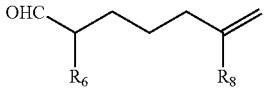

XIV

Alternatively, a compound of formula XIV can be prepared as shown in Scheme 3. Reaction of a compound of formula XXV and pseudoephedrine provides a compound of formula XXVI. A compound of formula XXVII can be prepared from a compound of formula XXVI by alkylation with a pentenyl halide such as 5-bromopentene according to the method of Meyers (i.e., Meyers, A.; et. al., J. Am. Chem. Soc., 1994, 116, 9361–9362). A compound of formula XXVIII can be prepared from a compound of formula XXVII with a reducing agent such as lithium pyrrolidinyl borohydride. Oxidation of a compound of formula XXVIII, using for example pyridinium cblorochromate, provides a compound of formula XIV. Direct conversion of a compound of formula XXVII to a compound of formula XIV can be accomplished with a reducing agent such as lithium triethoxy-aluminum hydride.

Scheme 4

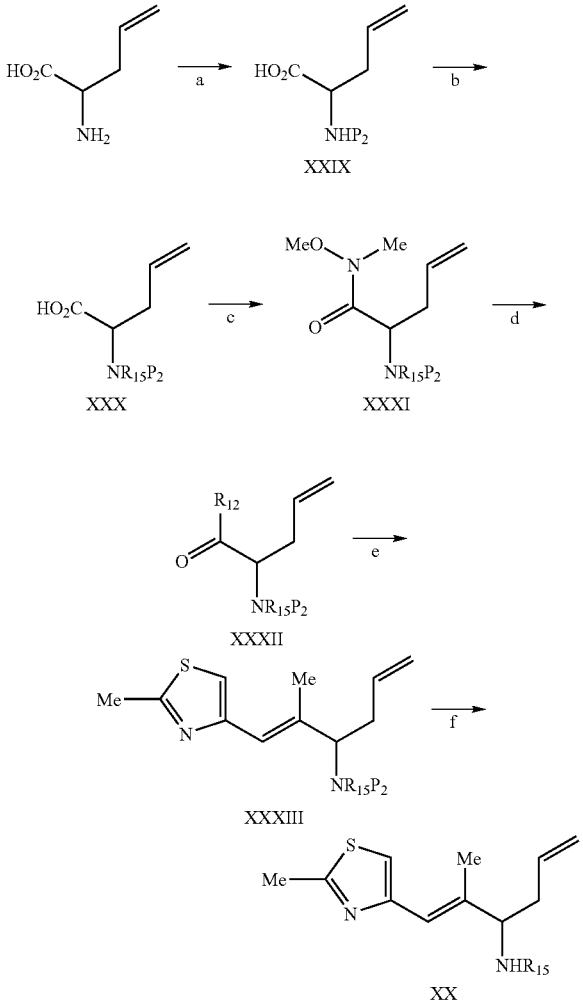

Alternatively, a compound of formula XX can be prepared from allylglycine as shown in Scheme 4. Allylglycine can be N-protected using methods known in the art to give a compound of formula XXIX, where $P_2$ is a suitable N-protecting group such as t-butyloxycarbonyl. Optionally, where $R_{29}$ is not hydrogen, a compound of formula XXX can be prepared from a compound of formula XXIX by alkylation with an alkyl halide in the presence of a base such as sodium hydride. A compound of formula XXXI can be prepared from a compound of formula XXX using N,O-dimethylhydroxylamine and standard coupling agents such as EDCI and HOBT. A compound of formula XXXII can be prepared from a hydroxamate XXXI by treatment with an organometallic reagent such as an alkyl or arylmagnesium halide. Wittig olefination of a compound of formula XXXII provides a compound of formula XXXIII (the Wittig reagent is prepared as reported: Danishefsky, S. E.; et. al., J. Org. Chem., 1996, 61, 7998–7999). N-Deprotection of a compound of formula XXXIII using methods known in the art provides a compound of formula XX.

Scheme 5

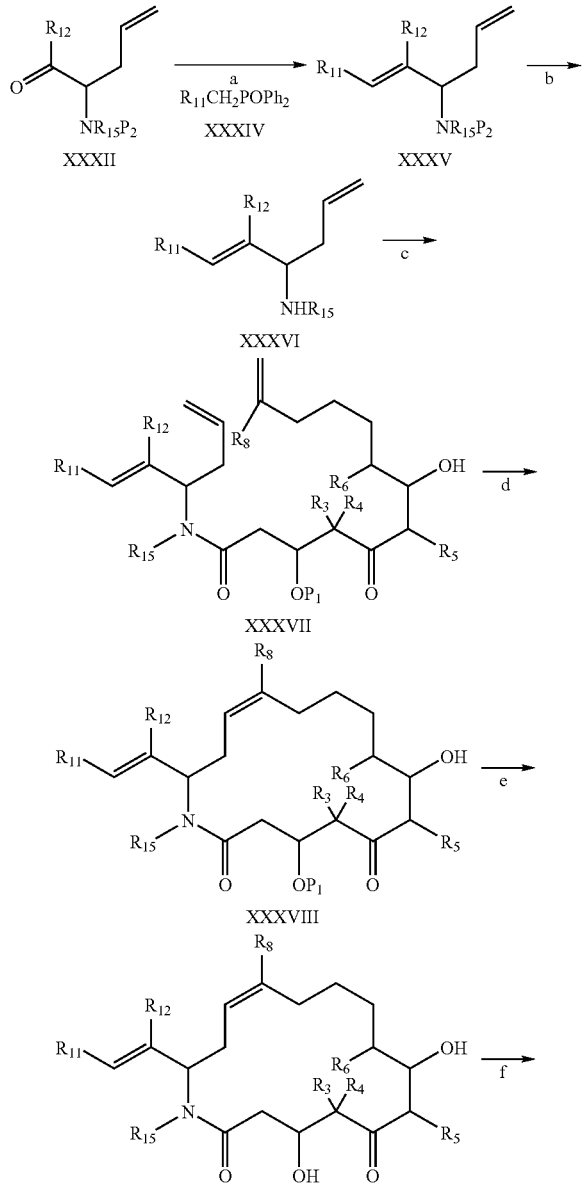

V(Q is ethylene group)

-continued

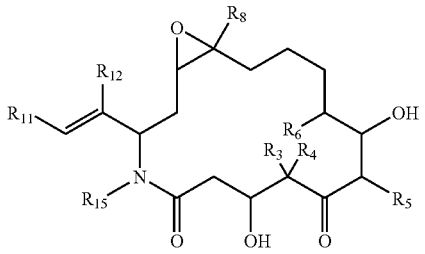

V(Q is oxirane group)

A compound of formula V where W is $NR_{15}$, X is oxygen, and G is a 1,2-disubstituted olefin can be prepared as shown in Scheme 5. A compound of formula XXXV can be prepared by Wittig olefination of a compound of formula XXXII. A compound of formula XXXIV can be prepared by methods known in the art. A compound of formula XXXVI can be prepared by N-deprotection of a compound of formula XXXV using methods known in the art. A compound of formula XXXVII can be prepared by coupling reaction of a compound of formula XXXVI and a compound of formula XIII using standard coupling agents such as EDCI and HOBT. A compound of formula XXXVIII can be prepared from a compound of formula XXXVII by methods described in Scheme 1 for the preparation of a compound of formula XXII. Using methods described in Scheme 1 (steps o and p), a compound of formula XXXVIII can be converted to compounds of formula V where W is $NR_{15}$, X is oxygen, and G is a 1,2-disubstituted olefin.

Scheme 6

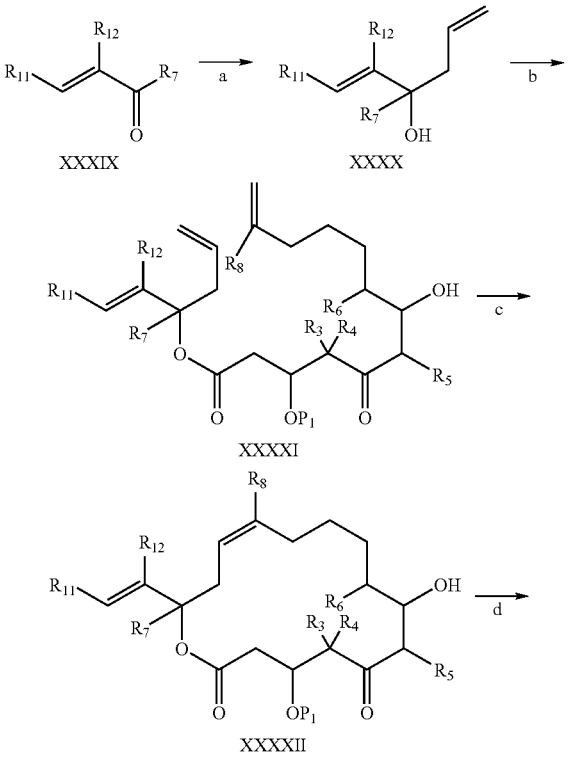

-continued

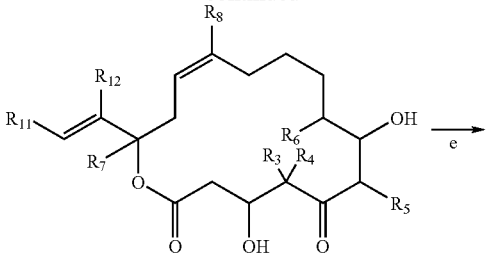

V(Q is ethylene group)

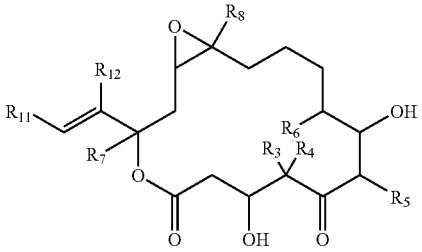

V(Q is oxirane group)

A compound of formula V where both W and X are oxygen, and G is a 1,2-disubstituted olefin can be prepared as shown in Scheme 6. A compound of formula XXXX can be prepared from a compound of formula XXXIX by treatment with an allylating agent such as allylmagnesium bromide. Enantiomerically pure XXXX can be prepared by employing chiral reagents (see, for example: Taylor, R. E.; et. al., Tetrahedron Lett., 1997, 38, 2061–2064; Nicolaou, K. C; et. al., Angew. Chem. Int. Ed. Engl., 1997, 36, 166–168, Keck, G., et. al., J. Am. Chem. Soc., 1993, 115, 8467). A compound of formula XXXXI can be prepared from compounds of formula XXXX and XIII by using standard esterification methods such as DCC and DMAP. A compound of formula XXXXII can be prepared from a compound of formula XXXXI via ring-closing olefin metathesis as described in Scheme 1 for the preparation of a compound of formula XXII. Compounds of formula V where both W and X are oxygen, and G is a 1,2-disubstituted olefin can be prepared from a compound of formula XXXXII by deprotection (where Q is an ethylene group) and, if desired, epoxidation (where Q is an oxirane group) as described above.

Scheme 7

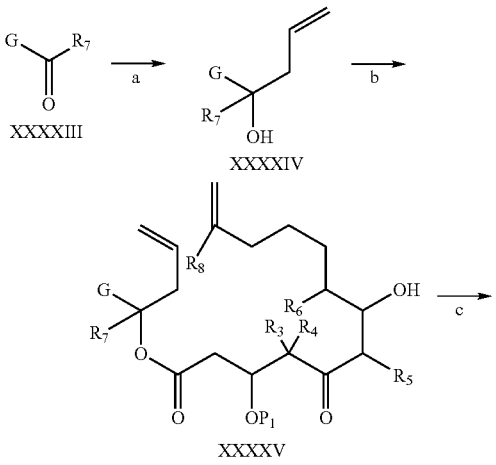

-continued

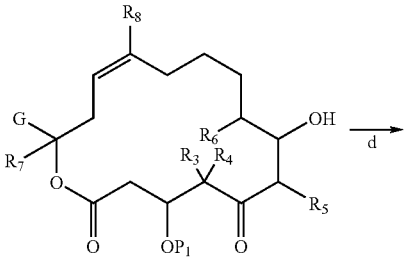

XXXXVI

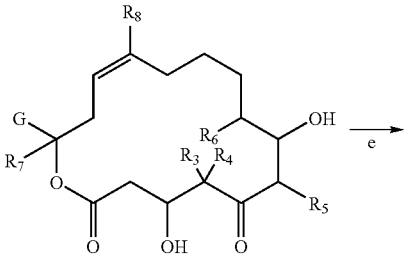

V(Q is ethylene group)

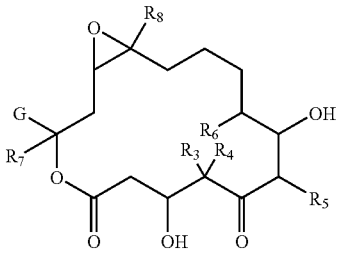

V(Q is oxirane group)

A compound of formula V where both W and X are oxygen, and G is alkyl, substituted alkyl, aryl, heteroaryl, bicycloaryl, or bicycloheteroaryl can be prepared as shown in Scheme 7. A compound of formula XXXXIV can be prepared by allylation of a compound of formula XXXXIII, where G is alkyl, substituted alkyl, aryl, heteroaryl, bicycloaryl, or bicycloheteroaryl, by reaction with an allylating reagent such as allyl magnesium bromide. A compound of formula XXXXV can be prepared from a compound of formula XXXXIV via esterification with a compound of formula XIII using, for example, DCC and DMAP. A compound of formula XXXXVI can be prepared from a compound of formula XXXXV by ring-closing metathesis as described above. Following the methods outlined above for Scheme 1, a compound of formula XXXXVI can be converted to compounds of formula V by deprotection and subsequent epoxidation.

Scheme 8

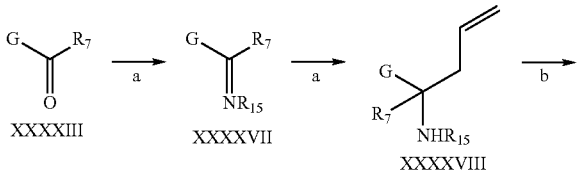

XXXXIII XXXXVII XXXXVIII

-continued

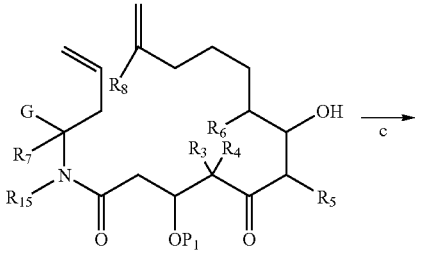

XXXXIX

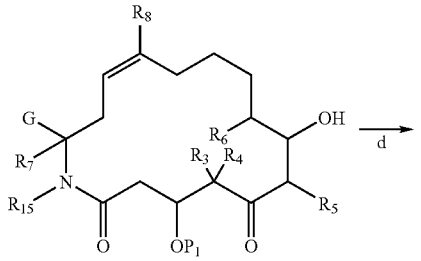

L

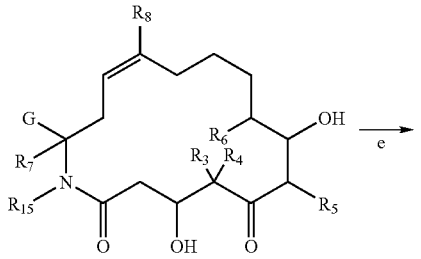

V(Q is ethylene group)

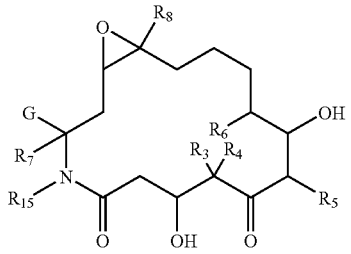

V(Q is oxirane group)

A compound of formula V where W is $NR_{15}$, X is oxygen, and G is alkyl, substituted alkyl, aryl, heteroaryl, bicycloaryl, or bicycloheteroaryl can be prepared as shown in Scheme 8. A compound of formula XXXXVII can be prepared by reaction of a compound of formula XXXXIII, where G is alkyl, substituted alkyl, aryl, heteroaryl, bicycloaryl, or bicycloheteroaryl, and an amine under dehydrating conditions. A compound of formula XXXXVIII can be prepared from a compound of formula XXXXVII by treatment with an allylating agent such as allylmagnesium bromide. A compound of formula XXXXIX can be prepared from a compound of formula XXXXVIII and a compound of formula XIII by standard amide bond coupling techniques using, for example, EDCI and HOBT. A compound of formula L can be prepared from a compound of formula XXXXIX by ring-closing metathesis as described above. Following the methods outlined above for Scheme 1, a compound of formula L can be converted to compounds of formulas V by deprotection and subsequent epoxidation.

Scheme 9

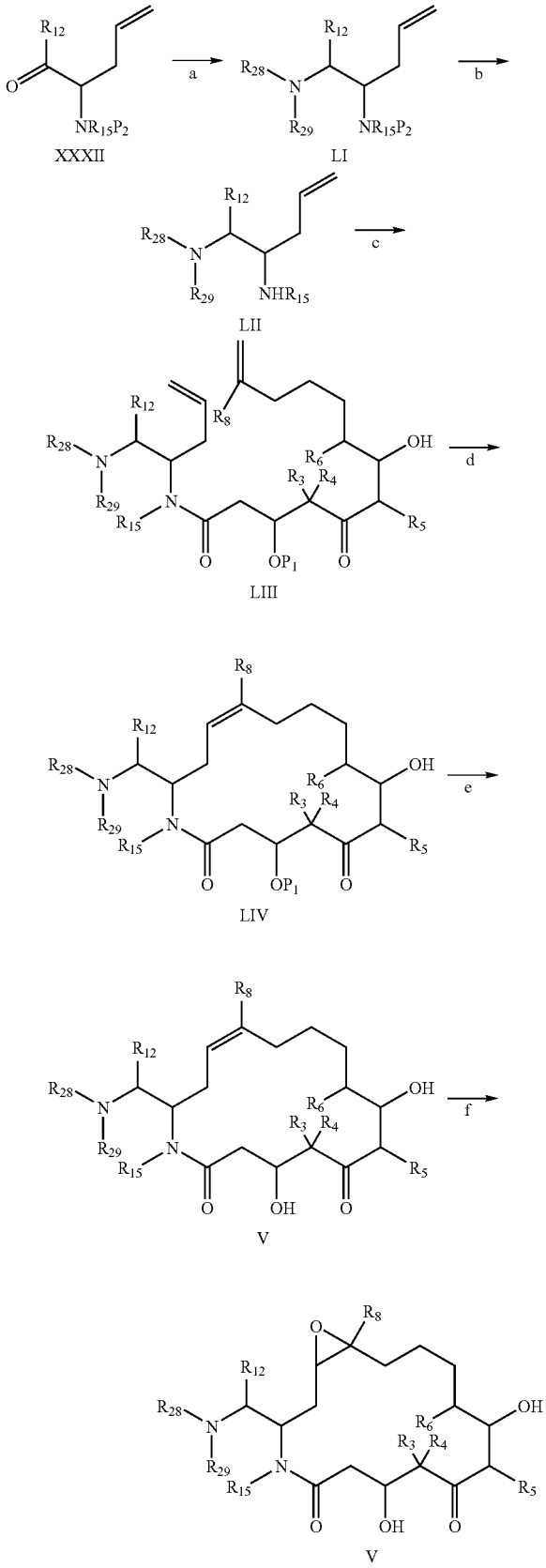

A compound of formula V where X is oxygen, W is $NR_{15}$, and G is

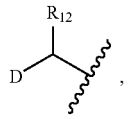

and D is selected from the group consisting of $NR_{28}R_{29}$, $NR_{30}COR_{31}$, and saturated heterocycle (i.e., piperidinyl, morpholinyl, piperazinyl, etc.) can be prepared as shown in Scheme 9. A compound of formula LI can be prepared from a compound of formula XXXII by reductive amination using a primary or secondary amine and a reducing agent such as sodium triacetoxyborohydride. Compounds of formula LIII, LIV, and V can then be prepared following methods described above in Scheme 1.

Scheme 10

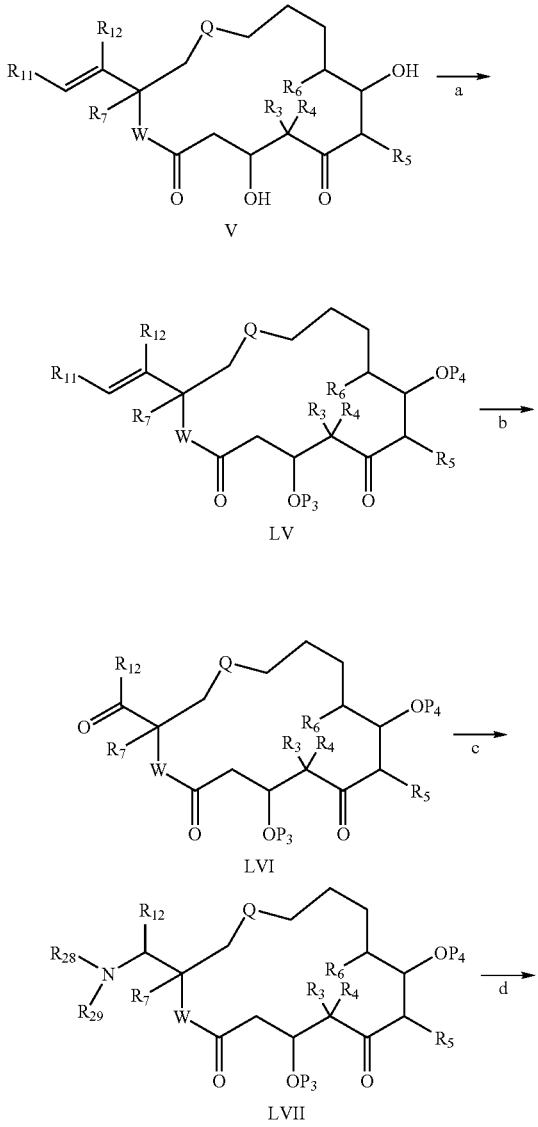

-continued

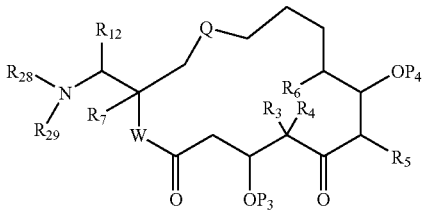

V

Alternatively, a compound of formula V where X is oxygen, W is oxygen or $NR_{15}$ or oxygen, and G is

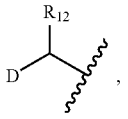

and D is selected from the group consisting of $NR_{28}R_{29}$, $NR_{30}COR_{31}$, and saturated heterocycle (i.e., piperidinyl, morpholinyl, piperazinyl, etc.) can be prepared from a compound of formula V as shown in Scheme 10. A compound of formula V can be converted to a compound of formula LV by protection of the hydroxyl groups with suitable protecting groups such as t-butyldimethylsilyl. A compound of formula LVI can be prepared from a compound of formula LV by ozonolysis. Treatment of a compound of formula LVI with an amine and a reducing agent such as sodium triacetoxyboro-hydride provides a compound of formula LVII. Removal of the protecting groups from a compound of formula LVII, with for example hydrogen fluoride, provides a compound of formula V where X is oxygen, W is $NR_{15}$ or oxygen, and G is

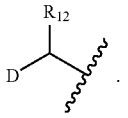

Scheme 11

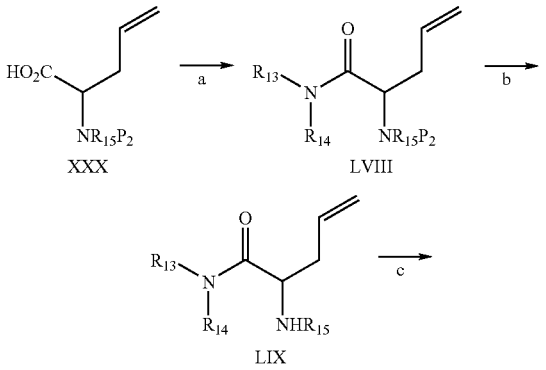

-continued

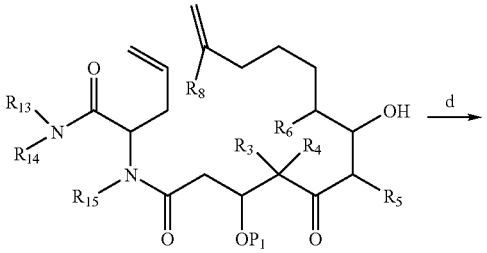

LX

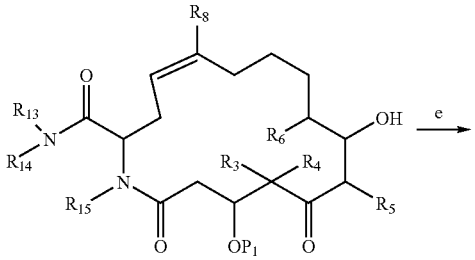

LXI

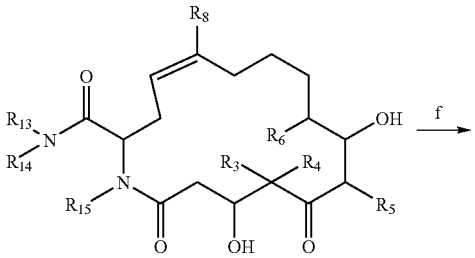

V

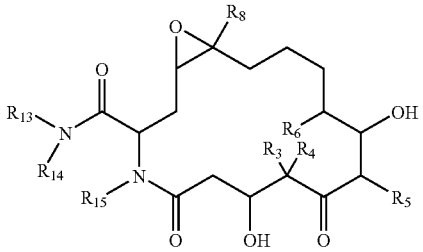

V

A compound of formula V where W is $NR_{15}$, X is oxygen, and G is

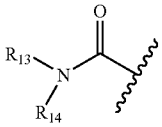

can be prepared as outline d in Scheme 11. A compound of formula LVIII can be prepared from a compound of formula XXX by treatment with an amine and standard amide bond coupling agents such as EDCI and HOBT. A compound of formula LX can be prepared from a compound of formula LVIII by N-deprotection, using for example trifluoroacetic acid when $P_2$ is a t-butyloxycarbonyl group, followed by coupling of compounds of formula LIX and XIII using standard amide bond coupling agents such as EDCI and HOBT.

A compound of formula LXI can be prepared from a compound of formula LX by ring-closing metathesis. A compound of formula V can be prepared from a compound of formula LXI following methods described in Scheme 1.

Scheme 12

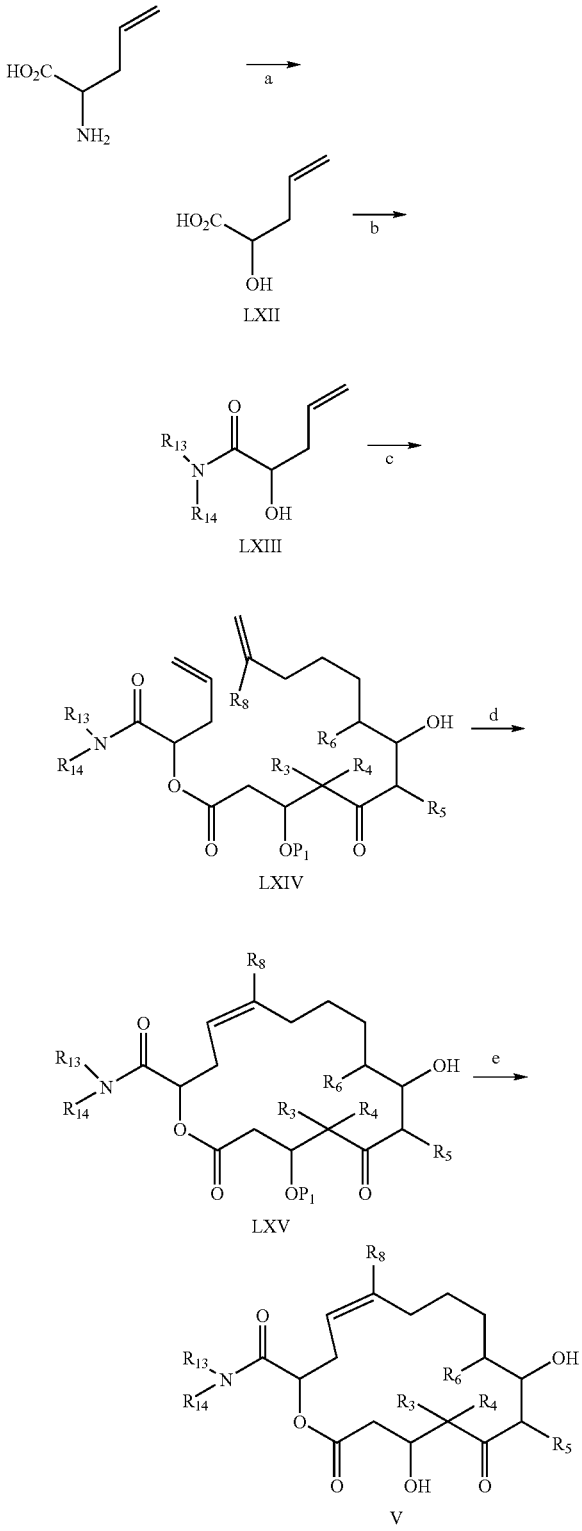

A compound of formula V where W is oxygen, X is oxygen, and G

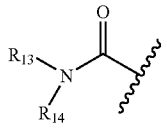

can be prepared as outlined in Scheme 12. A compound of formula LXII can be prepared from allylglycine by treatment with nitrous acid. A compound of formula LXIII can be prepared from a compound of formula LXII by treatment with an amine and standard amide bond coupling agents such as EDCI and HOBT. A compound of formula LXIV can be prepared from compounds of formula LXIII and XIII using standard amide bond coupling agents such as EDCI and HOBT. A compound of formula LXV can be prepared from a compound of formula LXIV by ring-closing metathesis. A compound of formula V can be prepared from a compound of formula LXV following methods described in Scheme 1.

Scheme 13

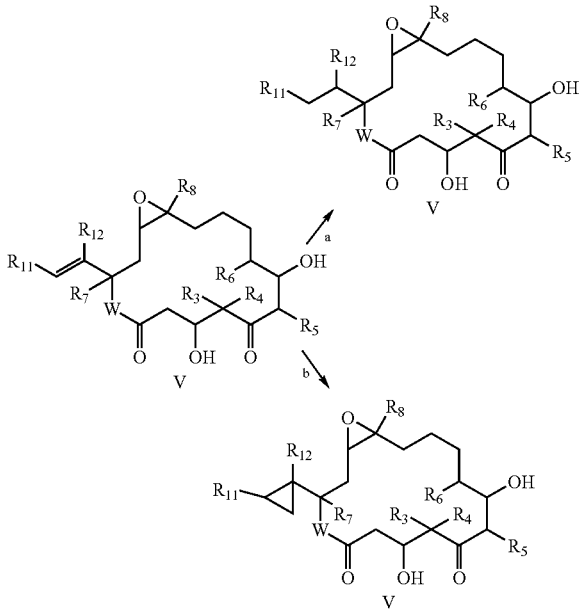

Compounds of formula V where G is a 1,2-disubstituted ethyl group can be prepared from a compound of formula V where G is a 1,2-disubstituted ethylene group by hydrogenation with a catalyst such as palladium on carbon, as shown in Scheme 13. Furthermore, compounds of formula V where G is a 1,2-disubstituted cyclopropyl group can be prepared from a compound of formula V where G is a 1,2-disubstituted ethylene group by cyclopropanation with diiodomethane and zinc-copper couple, as shown in Scheme 13.

Scheme 14

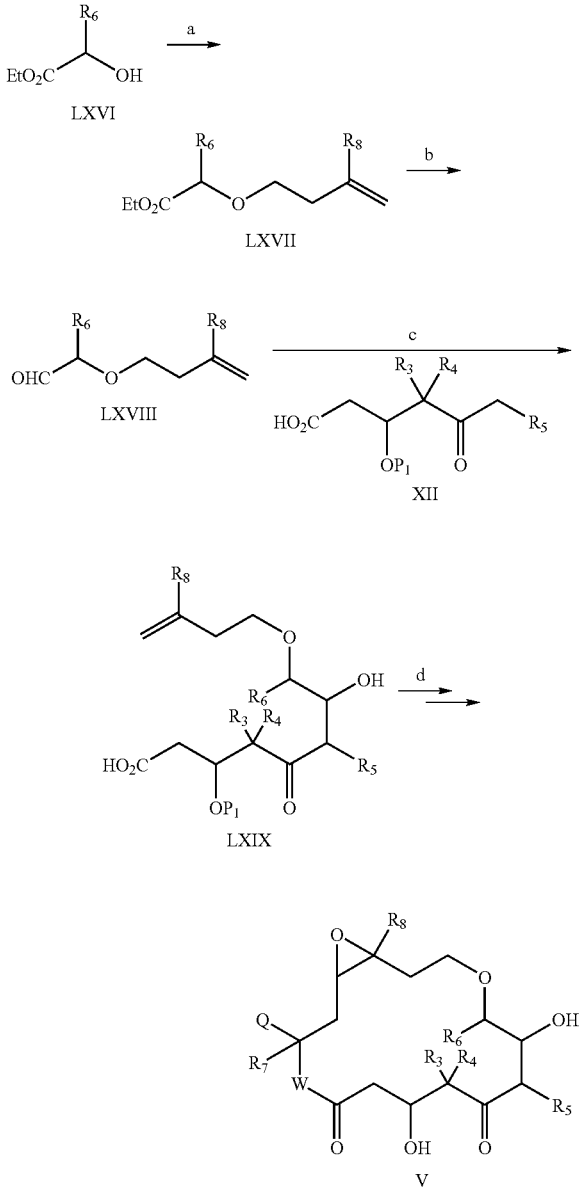

A compound of formula V where $Z_1$ is oxygen can be prepared as shown in Scheme 14. A compound of formula LXVII can be prepared from a alpha-hydroxy ester LXVI and a 3-buten-1-yl-trifluoromethanesulfonate (or with an 3-butenyl bromide and silver triflate). A compound of formula LXVII can be reduced with a reducing agent such as diisobutylaluminum hydride to provide a compound of formula LXVIII. Alternatively, a compound of formula LXVIII can be obtained from a compound of formula LXVII by a two step procedure involving reduction with lithium borohydride and oxidation with pyridinium chlorochromate. This compound of formula LXVIII can be substituted for a compound of formula XIV in Scheme 1 to give a compound of formula LXIX. Further elaboration of LXIX as described above provides a compound of formula V where $Z_1$ is oxygen.

Scheme 15

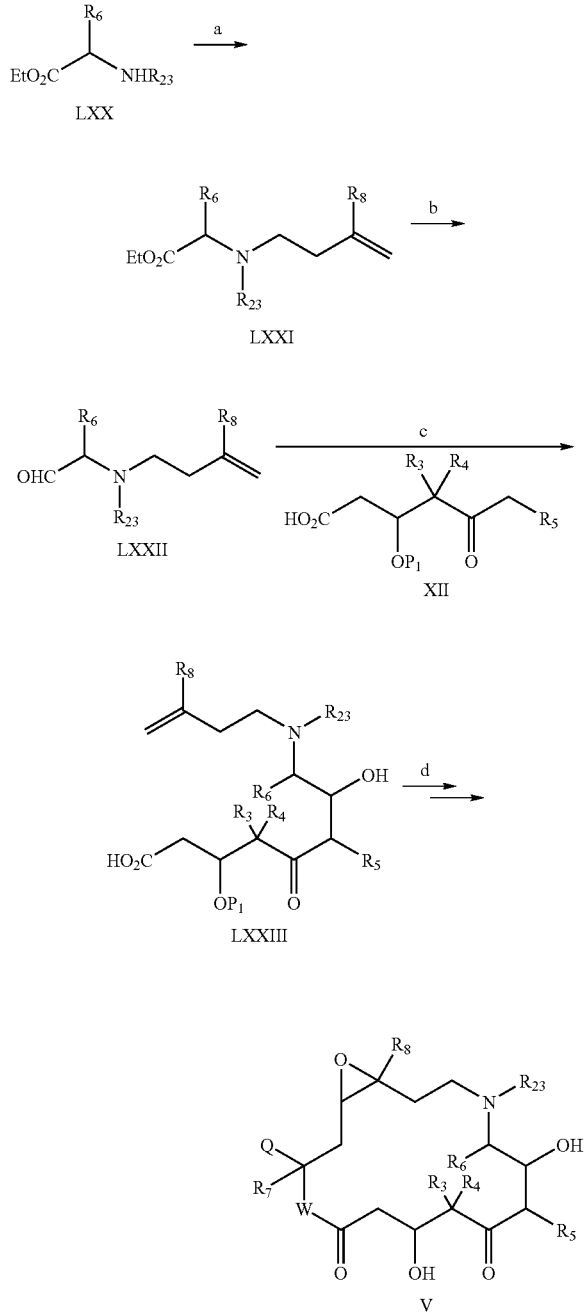

Similarly, a compound of formula V where $Z_1$ is $NR_{23}$ can be prepared as shown in Scheme 15. A compound of formula LXXI can be prepared from a alpha-amino ester LXX and a 3-buten-1-yl-bromide. A compound of formula LXXI can be reduced with a reducing agent such as diisobutylaluminum hydride to provide a compound of formula LXXII. Alternatively, a compound of formula LXXII can be obtained from a compound of formula LXXI by a two step procedure involving reduction with lithium borohydride and oxidation with pyridinium chlorochromate. This compound of formula LXXII can be substituted for a compound of formula XIV in Scheme 1 to give a compound of formula LXXIII. Further elaboration of LXXIII as described above provides a compound of formula V where $Z_1$ is $NR_{23}$.

Scheme 16

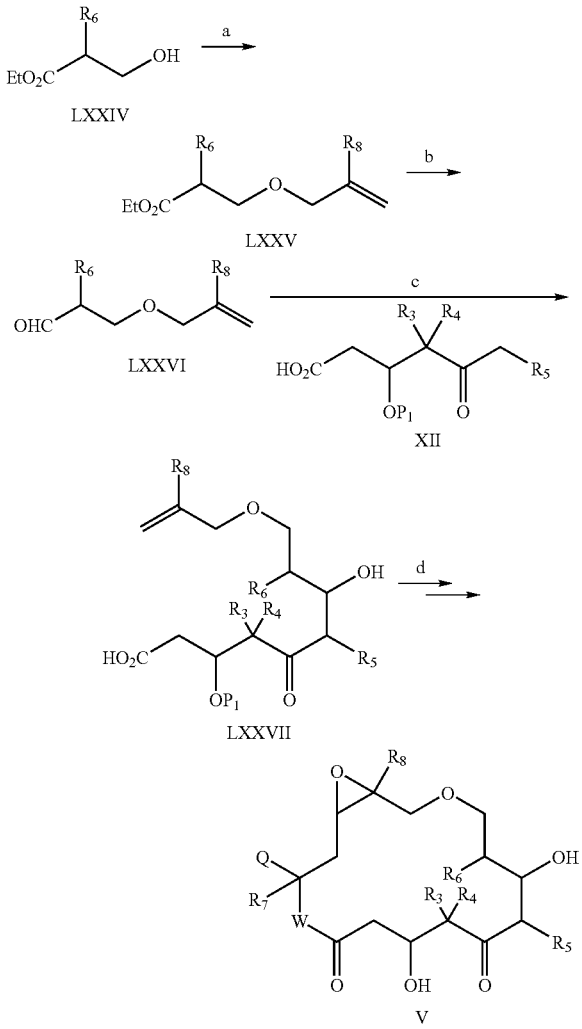

A compound of formula V where $Z_2$ is oxygen can be prepared as shown in Scheme 16. A compound of formula LXXV can be prepared from a beta-hydroxy ester LXXIV and an allylating agent such as allylbromide (or an allyl bromide and silver triflate). A compound of formula LXXV can be reduced with a reducing agent such as diisobutylaluminum hydride to provide a compound of formula LXXVI. Alternatively, a compound of formula LXXVI can be obtained from a compound of formula LXXV by a two step procedure involving reduction with lithium borohydride and oxidation with pyridinium chlorochromate. This compound of formula LXXVI can be substituted for a compound of formula XIV in Scheme 1 to give a compound of formula LXXVII. Further elaboration of LXXVII as described above provides a compound of formula V where $Z_2$ is oxygen.

Scheme 17

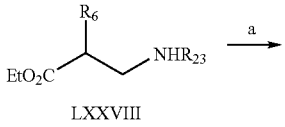

-continued

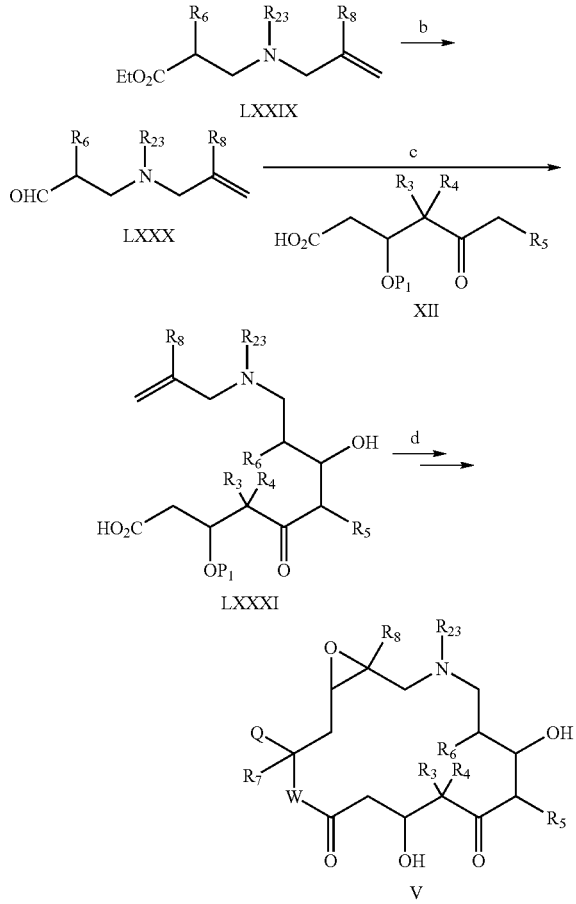

Similarly, a compound of formula V where $Z_2$ is $NR_{23}$ can be prepared as shown in Scheme 17. A compound of formula LXXIX can be prepared from a beta-amino ester LXXVIII and an allylating agent such as allylbromide. A compound of formula LXXIX can be reduced with a reducing agent such as diisobutylaluminum hydride to provide a compound of formula LXXX. Alternatively, a compound of formula LXXX can be obtained from a compound of formula LXXIX by a two step procedure involving reduction with lithium borohydride and oxidation with pyridinium chlorochromate. This compound of formula LXXX can be substituted for a compound of formula XIV in Scheme 1 to give a compound of formula LXXXI. Further elaboration of LXXXI as described above provides a compound of formula V where $Z_2$ is $NR_{23}$.

Scheme 18

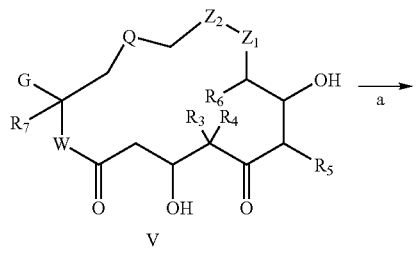

-continued

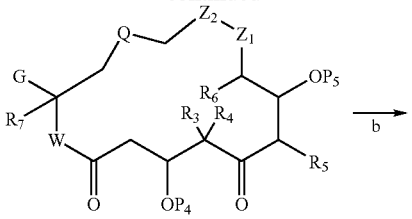

LXXXII

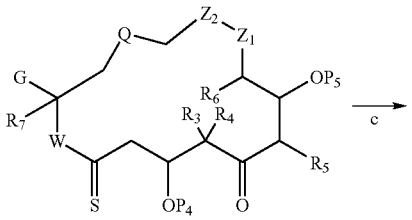

LXXXIII

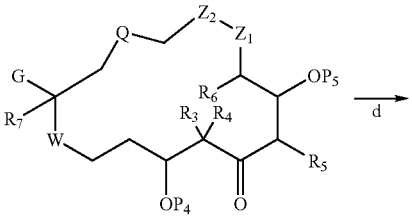

LXXXIV

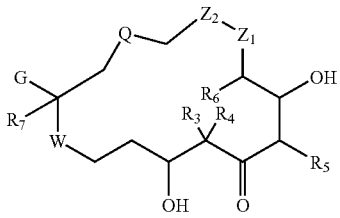

V

Scheme 19

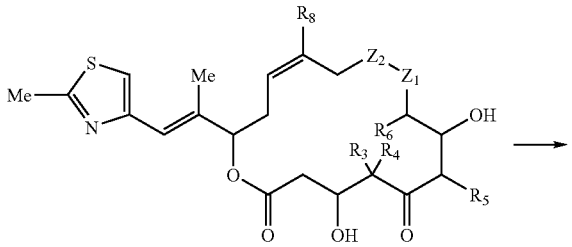

V

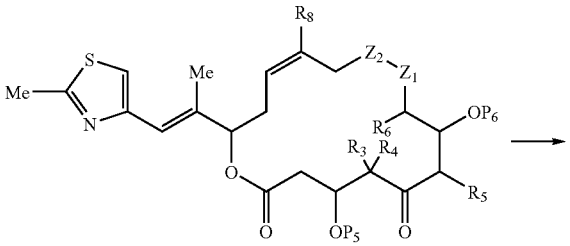

LXXXXV

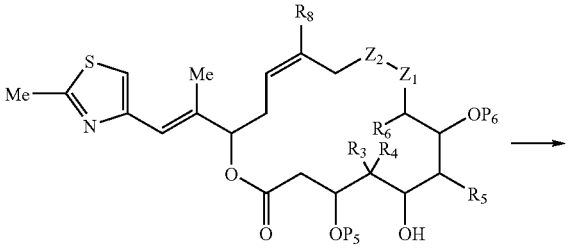

LXXXXVI

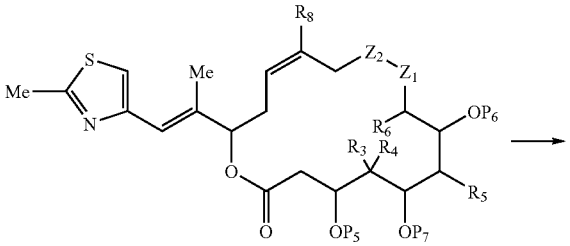

LXXXXVII

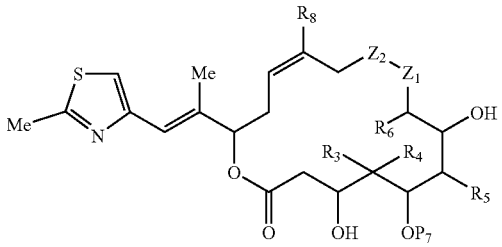

LXXXXVIII

A compound of formula V where W is oxygen or $NR_{15}$ and X is H,H can be prepared as shown in Scheme 18. A compound of formula V can be converted to a compound of formula [LXXIX] *LXXXII*, where $P_4$ and $P_5$ are hydroxyl protecting groups, by treatment with a reagent such as t-butyldimethylsilyltriflate. A compound of formula LXXXIII can be prepared from a compound of formula LXXXII by treatment with Lawesson's reagent. A compound of formula LXXXIV can be prepared from a compound of formula LXXXIII by using a reducing agent such as tri-n-butyltin hydride when W is oxygen or by treatment with methyl iodide and sodium borohydride when W is $NR_{15}$. Removal of the protecting groups from a compound of formula LXXXIV, using for example hydrogen fluoride when $P_4$ and $P_5$ are silyl groups, provides a compound of formula V where W is oxygen or $NR_{15}$, and X is H,H.

-continued

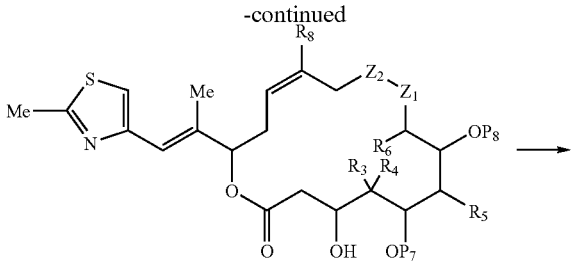

LXXXXIX

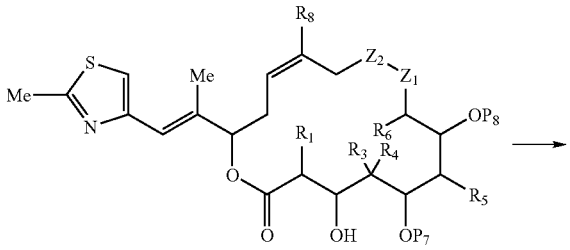

C

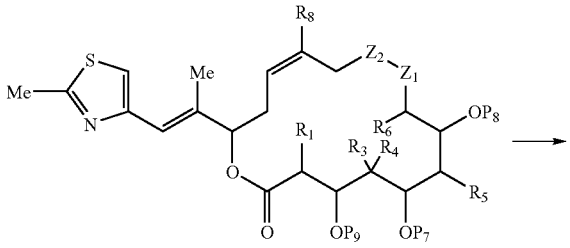

CI

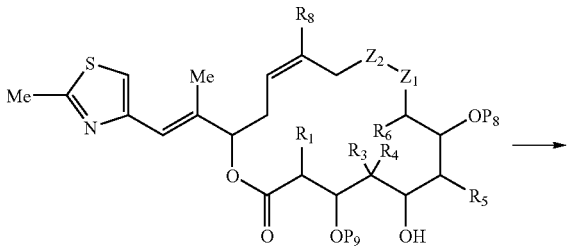

CII

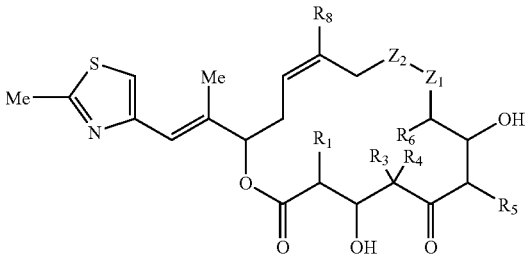

V

A compound of formula V where W, X and Y are oxygen, and $R_1$ is alkyl or substituted alkyl can be prepared as shown in Scheme 19. A compound of formula V can be protected to give a compound of formula LXXXXV, where $P_5$ and $P_6$ are hydroxyl protecting groups, by treatment with a reagent such as t-butyldimethylsilyl trifluoromethanesulfonate. A compound of formula LXXXXVI can be prepared from a compound of formula LXXXXV by treatment with a reducing agent such as sodium borohydride. A compound of formula LXXXXVII can be prepared from a compound of formula LXXXXVI by protection of the hydroxyl group, where $P_7$ is for example p-methoxybenzyl, using p-methoxybenzyl trichloroacetimidate. Removal of the protecting groups $P_5$ and $P_6$ of a compound of formula LXXXXVII using, for example, hydrogen fluoride in pyridine when $P_5$ and $P_6$ are t-butyldimethylsilyl groups provides a compound of formula LXXXXVIII which then can be selectively protected using for example t-butyldimethylsilyl chloride to give a compound of formula LXXXXIX where $P_8$ is a t-butyldimethylsilyl group. A compound of formula C can be prepared from a compound of formula LXXXXIX by treatment with a base such as lithium diisopropylamide followed by treatment with an alkylating agent such as methyl iodide. A compound of formula C can be protected to give a compound of formula CI, where $P_9$ is a hydroxyl protecting group, by treatment with a reagent such as t-butyldimethylsilyl trifluoromethanesulfonate. A compound of formula CII can be prepared from a compound of formula CI by removal of the $P_7$ group using, for example, DDQ when $P_7$ is a p-methoxybenzyl group. A compound of formula V, where W, X and Y are oxygen, and $R_1$ is alkyl or substituted alkyl, can be prepared from a compound of formula CII by oxidation using, for example, TPAP/NMO followed by removal of the protecting groups using, for example, hydrogen fluoride when $P_8$ and $P_9$ are silyl groups. This compound of formula V can be further oxidized with dimethyldioxirane as shown in Scheme 1 to provide the corresponding epoxide compound of formula V.

Scheme 20

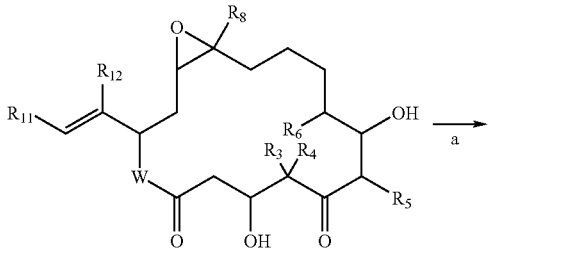

V(Q is oxirane group)

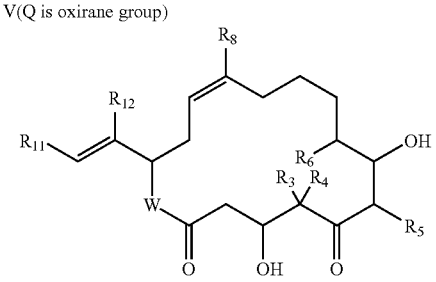

V(Q is ethylene group)

A compound of formula V where X is oxygen and Q is an olefin can be prepared from a compound of formula V where X is oxygen and Q is an oxirane ring by treatment with a reactive metallocene such as titanocene, zirconocene or niobocene as shown in Scheme 20 (see for example R. Schobert and U. Hohlein, Synlett (1990), 465–466.).

Scheme 21

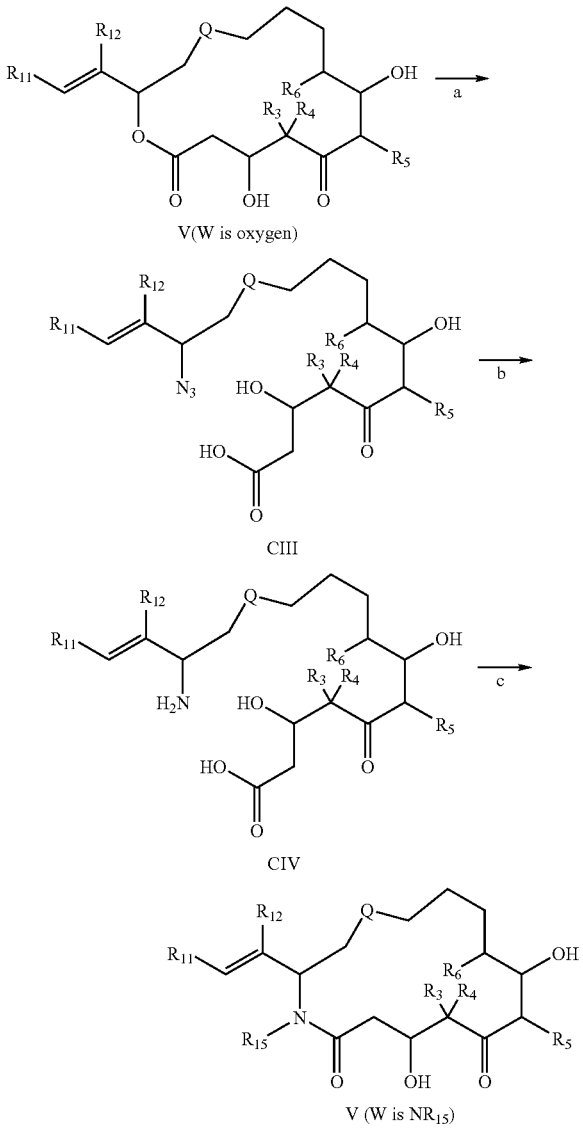

A compound of formula V where X is oxygen and W is $NR_{15}$, where $R_{15}$ is hydrogen, can be prepared from a compound of formula V where both X and W are oxygen as shown in Scheme 21. A compound of formula CIII can be prepared from a compound of formula V where both X and W are oxygen by formation of pi-allylpalladium complex using, for example, palladium tetrakistriphenylphosphine followed by treatment with sodium azide (see, for example: Murahashi, S.-I.; et. al. J. Org. Chem. 1989, 54, 3292). Subsequent reduction of a compound of formula CIII with a reducing agent such as triphenylphosphine provides a compound of formula CIV. A compound of formula V where X is oxygen and W is $NR_{15}$, where $R_{15}$ is hydrogen, can be prepared from a compound of formula CIV by macrolactamization using, for example, diphenylphosphoryl azide or bromotripyrrolidinophosphonium hexafluorophosphate (PyBroP).

Scheme 22

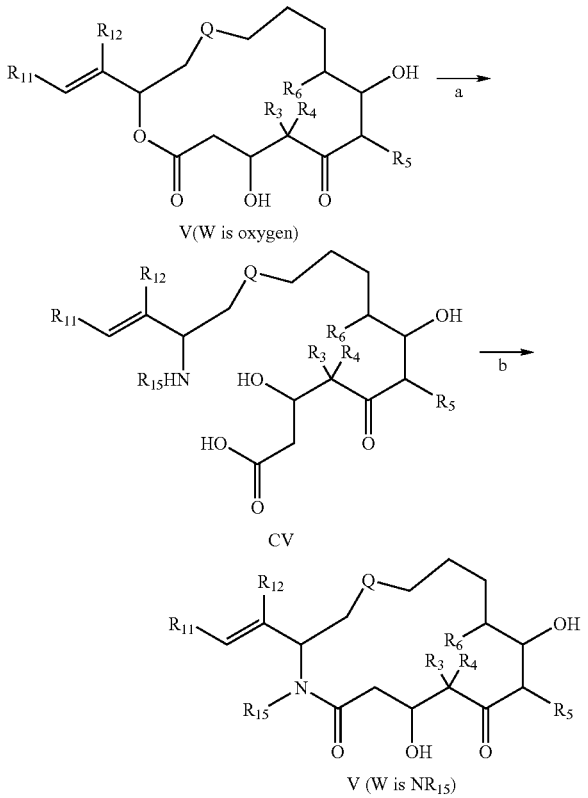

A compound of formula V where X is oxygen and W is $NR_{15}$, where $R_{15}$ is alkyl, substituted alkyl, aryl, heteroaryl, cycloalkyl, heterocyclo, O-alkyl, O-substituted alkyl, can be prepared from a compound of formula V where both X and W are oxygen as shown in Scheme 22. A compound of formula CV can be prepared from a compound of formula V where both X and W are oxygen by formation of pi-allylpalladium complex using, for example, palladium tetrakistriphenylphosphine followed by treatment with a primary amine. A compound of formula V where X is oxygen and W is $NR_{15}$, where $R_{15}$ is alkyl, substituted alkyl, aryl, heteroaryl, cycloalkyl, heterocyclo, OH, O-alkyl, O-substituted alkyl, can be prepared from a compound of formula CV by macrolactamization using, for example, diphenylphosphoryl azide or bromotripyrrolidinophosphonium hexafluorophosphate (PyBroP). In the case where $R_{15}$ is OH, it may be necessary to remove a protecting group such as t-butyldimethylsiiyl from an intermediate where $R_{15}$ is O-t-butyldimethylsilyl.

The in vitro assessment of biological activity of the compounds of Formula V was performed as follows:

In vitro Tubulin Polymerization.

Twice cycled (2×) calf brain tubulin was prepared following the procedure of Williams and Lee (see Williams, R. C., Jr., and Lee, J. C. Preparation of tubulin from brain. Methods in Enzymology 85, Pt. D: 376–385, 1982) and stored in liquid nitrogen before use. Quantification of tubulin polymerization potency is accomplished following a modified procedure of Swindell, et al., (see Swindell, C. S., Krauss, N. E., Horwitz, S. B., and Ringel, I. Biologically active taxol analogues with deleted A-ring side chain substituents and variable C-2' configurations. J. Med. Chem. 34: 1176–1184, 1991). These modifications, in part, result in the expression of tubulin polymerization potency as an effective concentration for any given compound. For this method, different concentrations of compound in polymerization buffer (0.1M MES, 1 mM EGTA, 0.5 mM $MgCl_2$, pH 6.6) are added to tubulin in polymerization buffer at 37° in microcuvette wells of a Beckman (Beckman Instruments) Model DU 7400 UV spectrophotometer. A final microtubule protein concentration of 1.0 mg/ml and compound concentration of generally 2.5, 5.0, and 10 μM are used. Initial slopes of OD change measured every 10 seconds were calculated by the program accompanying the instrument after initial and final times of the linear region encompassing at least 3 time points were manually defined. Under these conditions linear variances were generally $<10^{-6}$, slopes ranged from 0.03 to 0.002 absorbance unit/minute, and maximum absorbance was 0.15 absorbance units. Effective concentration ($EC_{0.01}$) is defined as the interpolated concentration capable of inducing an initial slope of 0.01 OD/minute rate and is calculated using the formula: $EC_{0.01}$=concentration/slope. $EC_{0.01}$ values are expressed as the mean with standard deviation obtained from 3 different concentrations. $EC_{0.01}$ values for the compounds in this invention fall in the range 0.01–1000μM.

Cytotoxicity (In-Vitro)

Cytoxicity was assessed in HCT-116 human colon carcinoma cells by MTS (3-(4,5-dimethylthiazol-2-yl)-5-(3-carboxymethoxyphenyl)-2-(4-sulphenyl)-2H-tetrazolium, inner salt) assay as reported in T. L. Riss, et. al., "Comparison of MTT, XTT, and a novel tetrazolium compound MTS for in vitro proliferation and chemosensitivity assays.," Mol. Biol. Cell 3 (Suppl.):184a, 1992. Cells were plated at 4,000 cell/well in 96 well microliter plates and 24 hours later drugs were added and serial diluted. The cells were incubated at 37° form 72 hours at which time the tetrazolium dye, MTS at 333 μg/ml (final concentration), in combination with the electron coupling agent phenazine methosulfate at 25 μM (final concentration) was added. A dehydrogenase enzyme in live cells reduces the MTS to a form that absorbs light at 492 nM which can be quantitated spectrophotometrically. The greater the absorbance the greater the number of live cells. The results are expressed as an $IC_{50}$, which is the drug concentration required to inhibit cell proliferation (i.e. absorbance at 450 nM) to 50% of that of untreated control cells. The $IC_{50}$ values for compounds of this invention fall in the range 0.01–1000 nM.

The following examples illustrate the present invention.

EXAMPLE 1

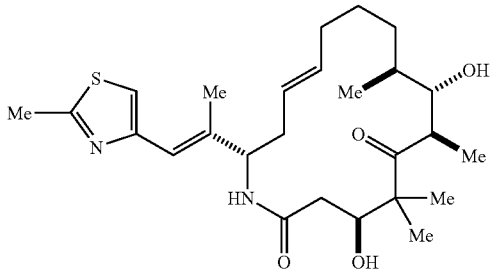

[4S-[4R*,7S*,8R*,9R*,15R*(E)]]4,8-Dihydroxy-5,5,7,9-tetramethyl-16-[1-methyl-[2-(2-methyl-4thiazolyl)ethenyl]-1-aza-13(E)-cyclohexadecene-2,6-dione A. N-[(2-Methyl)-1-propenyl]morpholine.

To stirring morpholine (165.5 g, 1.9 mol) was added isobutyraldehyde (173 mL, 1.9 mol) at a rate which did not allow the temperature of the reaction to exceed 30° C. After complete addition, the reaction mixture was stirred at room temperature for 2 h, and then the flask was equipped with a Dean-Stark trap and heated at 160° C. for 20 h. The reaction mixture was then cooled to room temperature, and the flask was equipped with a vigreux column distillation apparatus. Distillation under high vacuum gave 135 g (50%) of Compound A as a clear colorless oil. MS (M+H, 142).

B. 2,2[-Dimethyl-3-oxopentanal.

To a stirring solution of propionyl chloride (44 mL, 0.50 mol) in ether (135 mL) at 0° C. under nitrogen was added a solution of Compound A (69 g, 0.50 mol) in ether (135 mL) over 45 min. After addition was complete, the reaction mixture was stirred at reflux for 2 h, and then stirred at room temperature for 16 h. The reaction mixture was filtered, and the filter cake was washed with ether (50 mL). The volatiles were removed in vacuo. The residue was taken into $H_2O$ (80 mL) and the solution was adjusted to a pH of 4. Ether was added (80 mL) and the biphasic mixture was stirred for 16 h. The reaction mixture was poured into a separatory funnel, the layers separated, and the aqueous layer was extracted with ether (5×100 mL). The combined organics were dried ($MgSO_4$), filtered, and evaporated in vacuo. The residue was distilled under high vacuum to give 10.4 g (16%) of Compound B as a clear, colorless oil. MS (M−H, 127).

C. 4-tert-Butyldimethylsilyloxy-5,5-dimethyl-6-oxo-1-octene.

To a solution of (−)-B-methoxydiisopinocamphenylborane (25.7 g, 81 mmol) in ether (80 mL) at 0° C. under nitrogen was added 1.0 M allylmagnesium bromide in ether (77 mL, 77 mmol) over 1.5 h. The reaction mixture was stirred at 25° C. for 1 h, and then concentrated in vacuo. The residue was extracted with pentane (2×150 mL), and the extracts were filtered through Celite under nitrogen. The combined extracts were then evaporated in vacuo to give the B-allyldiisopinocamphenylborane. This material was taken up in ether (200 mL) and cooled to −100° C. under nitrogen. A solution of Compound B (11.42 g, 89 mmol) in ether (90 mL) at −78° C. was then added over a 1 h period. The reaction mixture was stirred for an additional 0.5 h and methanol (1.5 mL) was added. The reaction mixture was brought to room temperature, treated with 3 N NaOH (32 mL) and 30% $H_2O_2$ (64 mL), and then kept at reflux for 2 h. The reaction mixture was cooled to room temperature, the layers were separated, and the organic phase was washed with $H_2O$ (500 mL). The combined aqueous washes were re-extracted with ether (2×100 mL). The combined organic extracts were washed with saturated aqueous NaCl (100 mL), dried ($MgSO_4$), filtered, and concentrated in vacuo. This residue was taken up in $CH_2Cl_2$ (250 mL), cooled to 0° C., and diisopropylethylamine (93 mL, 535 mmol) was added. To the stirring solution was then added tert-butyldimethylsilyl trifluoromethanesulfonate (69 g, 260 mmol) slowly as to not increase the temperature above 10° C. After complete addition, the reaction mixture was poured into $H_2O$ (650 mL), the layers were separated, and the aqueous layer was extracted with $CH_2Cl_2$ (2×650 mL). The combined organics were dried ($Na_2SO_4$), filtered, and concentrated in vacuo. The residue was purified by flash chromatography eluting with hexanes followed by 10% EtOAc/hexanes to give 17.2 g (78%) of Compound C as a clear, colorless oil. The enantiomeric excess was found to be 94% determined by $^1H$ NMR analysis of the Mosher's ester of the alcohol. $^{13}C$ NMR ($CDCl_3$, 80 MHz) d 215.8, 136.1, 116.5, 52.8, 39.0, 31.9, 26.0, 22.4, 20.1, 18.1, 7.6, −3.6, −4.4.

D. 3-tert-Butyldimethylsiloxy-4,4-dimethyl-5-oxoheptanal.

Through a solution of Compound C (10.8 g, 38.0 mmol) in $CH_2Cl_2$ at −78° C. was bubbled $O_3$ until the solution remained blue (1 h). Oz was then bubbled through for 15 min followed by $N_2$ for 30 min after which time the solution became clear. Triphenylphosphine (10 g, 38 mmol) was then added and the reaction mixture was warmed to −35° C. and stored for 16 h. The volatiles were removed in vacuo and the residue was purified by flash chromatography eluting with 8% EtOAc/hexanes to give 8.9 g (74%) of Compound D as a clear, colorless oil. $^1$H NMR ($CDCl_3$, 300 MHz) d 9.75 (m, 1H), 4.53 (t, J=4.8 Hz, 1H), 3.40–3.60 (m, 4H), 1.10 (s, 3H), 1.07 (s, 3H), 0.98 (t, J=7.0 Hz, 3H), 0.83 (s, 9H), 0.07 (s, 3H), 0.04 (s, 3H).

E. 3tert-Butyldimethylsiloxy-4,4-dimethyl-5-oxoheptanoic acid.

To a solution of Compound D (3.90 g, 13.6 mmol) in t-butanol (75 mL) was added 2-methyl-2-butene (5.85 mL, 55.2 mmol), and then a solution of sodium chlorite (4.61 g, 40.8 mmol) and sodium phosphate monobasic (2.81 g, 20.4 mmol) in $H_2O$ (15 mL) was added dropwise at room temperature. The reaction mixture was stirred for 0.5 h and then the solvents were removed in vacuo. To the residue was added $H_2O$ (150 mL) followed by extraction with EtOAc (3×150 mL). The combined organic extracts were dried ($MgSO_4$), filtered, and the volatiles were removed in vacuo. The residue was purified by flash chromatography eluting with 20% EtOAc/hexanes/1% AcOH to give 3.79 g (92%) of Compound E as a clear, colorless, viscous oil. MS (M+H, 303)

F. (R,R)-N-(2-Hydroxy-1-methyl-2-phenethyl)-N,2-(S)-dimethyl-6-hepteneamide.

A suspension of LiCl (6.9 g, 0.16 mol) and preformed lithium diisopropylamide (Aldrich, 2.0 M solution in heptane/ethylbenzene/THF, 27.6 mL, 55 mmol) in additional THF (70 mL) at −78° C. was treated dropwise with a solution of (R,R)-N-(2-hydroxy-1-methyl-2-phenylethyl)-N-methyl propionamide (6.0 g, 27 mmol, Meyers, A. G. et al. J. Am. Chem. Soc. 1994, 116, 9361) in THF (30 mL) over 10 min. The bright yellow, reaction mixture was stirred at −78° C. (1 h), at 0° C. (15 min), and at 25° C. (5 min) before being recooled to 0° C. and treated with a solution of 5-bromo-1-pentene (4.8 mL, 40 mmol) in THF (5 mL). The reaction mixture was stirred at 0° C. (24 h), poured into saturated aqueous $NH_4Cl$ (100 mL) and EtOAc (100 mL). The two phases were separated and the aqueous phase was further extracted with EtOAc (3×100 mL). The organic extracts were combined, washed with saturated aqueous NaCl (200 mL), dried (Na2$SO_4$), and concentrated in vacuo. Flash chromatography ($SiO_2$, 4.0×25 cm, 2 % MeOH—$CHCl_3$) afforded Compound F (6.9 g, 88%) as a pale yeUow oil. MS (ESI$^+$): 290 $(M+H)^+$; MS(ESI$^-$): 288.2 $(M-H)^-$.

G. (S)-2-Methyl-6-heptenol.

A 250 mL round-bottom flask at 0° C. was charged sequentially with pyrrolidine (2.6 mL, 30 mmol) and $BH_3$-THF complex (1.0 M in THF, 31 mL, 30 mmol). The borane-pyrrolidine complex was warmed to 25° C. (1 h), recooled to 0° C., and treated with n-butyllithium (1.6 M in hexane, 19 mL, 30 mmol) dropwise over 30 min while carefully maintaining an internal temperature below 5.5° C. The reaction mixture was stirred at 0° C. for an additional 30 min before a solution of Compound F (3.0 g, 10 mmol) in THF (23 mL) was added dropwise over 10 min. The reaction mixture was stirred at 25° C. (6 h) before being quenched by the dropwise addition of aqueous 3 N HCl (25 mL). The reaction mixture was then poured into aqueous 1 N HCl (200 mL) and extracted with $Et_2O$ (4×80 mL). The combined organics were washed with a 1:1 solution of saturated aqueous NaCl-aqueous 1 N HCl (2×150 mL) and concentrated in vacuo. An aqueous solution of NaOH (1 N, 200 mL) was added to the residue and the suspension was stirred for 30 min. The mixture was extracted with $Et_2O$ (3×100 mL) and the combined ether layers were washed with a 1:1 solution of saturated aqueous NaCl-aqueous 1 N NaOH (2×200 mL), dried ($Na_2SO_4$), and concentrated in vacuo. Flash chromatography ($SiO_2$, 4.0×25 cm, 15–25% $Et_2O$-pentane gradient elution) afforded Compound G (1.26 g, 95%) as a colorless oil. $[a]^{25}$D-11 (c 12, $CH_2Cl_2$).

H. (S)-2-Methyl-6-heptenal.

A solution of Compound G (0.24 g, 1.9 mmol) in $CH_2Cl_2$ (6 mL) was treated with pyridinium chlorochromate (0.61 g, 2.8 mmol) and the reaction mixture was stirred at 25° C. for 5 h. The resulting dark brown viscous slurry was passed through a silica gel-Celite plug (Celite 1.0×1 cm on top of $SiO_2$, 1.0×5 cm, eluting with 50 mL of $CH_2Cl_2$). The solvent was removed in vacuo to afford crude Compound H (0.15 g, 63%) as a colorless oil, which was sufficiently pure to use in subsequent reactions. $^1$H NMR (300 MHz, $CD_2Cl_2$) d 9.62 (s, 1H), 5.88–5.68 (m, 1H), 5.13–4.92 (m, 2H), 2.37–2.24 (m, 1H), 2.15–2.05 (m, 2H), 1.62–1.78 (m, 1H), 1.51–1.32 (m, 3H), 1.07 (d, 3H, J=7.0 Hz).

I. (3S,6R,7S,8S)-3-tert-Butyldimethylsiloxy-4,4,6,8-tetramethyl-7-hydroxy-5-oxo-12-tridecenoic acid.

To a preformed LDA solution (Aldrich, 2.0 M solution in heptane/ethylbenzene/THF, 3.8 mL, 7.6 mmol) in additional THF (25 mL) at −78° C. was added a solution of Compound E (1.0 g, 3.4 mmol) in THF (5 mL) dropwise over 3 min. The reaction mixture was stirred at −78° C. (10 min), warmed to −40° C. (20 min), and recooled to −78° C. before Compound H (0.56 g, 4.4 mmol) in THF (5 mL) was added. The reaction mixture was warmed to −40° C., stirred for 1 h, and : diluted with saturated aqueous $NH_4Cl$ (50 mL). The two layers were separated and the aqueous phase was extracted with EtOAc (4×50 mL). The combined organic layers were washed with saturated aqueous NaCl (100 mL), dried ($Na_2SO_4$), and concentrated in vacuo. Flash chromatography ($SiO_2$, 2.5×20 cm, 2–5% MeOH—$CHCl_3$ gradient elution) followed by HPLC (YMC S-10, ODS, 30×500 mm column, eluting with MeOH at a flow rate of 20 mL/min) separation afforded the desired syn-aldol product Compound I (0.60 g, 43%) and an undesired diastereomer (0.32 g, 22%) along with starting Compound E (~10%).

MS (ESI$^+$): 879.3 $(2M+Na)^+$, 451.2 $(M+Na)^+$, 429.2 $(M+H)^+$; MS(ESI$^-$): 427.3 $(M-H)^-$.

Stereochemistry was confirmed by direct comparison of both the $^{13}$C and $^1$H NMRs of the subsequent ester derivative (used in the synthesis of Epothilone C) to the same intermediate previously described by K. C. Nicolaou et al. Angew. Chem. Int. Ed. Engl. 1997, 36, 166.

J. (S)-2[N-[(tert-Butyloxy)carbonyl]amino]-4pentenoic acid.

A solution L-2-amino-4-pentenoic acid (NovaBiochem, 3.0 g, 26 mmol) in THF-$H_2O$ (1:1, 200 mL) at 0° C. was treated sequentially with $NaHCO_3$ (6.6 g, 78 mmol) and di-tert-butyl dicarbonate (10.4 g, 1.8 mmol). The reaction mixture was warmed to 25° C. and stirred for 16 h. The pH of the mixture was adjusted to 4 by the careful addition of saturated aqueous citric acid at 0° C., and the mixture was extracted with EtOAc (4×50 mL). The combined organic layers were washed with saturated aqueous NaCl (75 mL), dried ($Na_2SO_4$), and concentrated in vacuo. Flash chromatography ($SiO_2$, 4.0×6 cm, 5–10% MeOH—$CHCl_3$ gradient elution) afforded Compound J (5.5 g, 99%) as a colorless oil. MS(ESI$^-$): 429.3 $(2M-H)^-$, 214.1 $(M-H)^-$.

K. (S)-2-[$N^2$-[(tert-Butyloxy)carbonyl]amino]-N-methoxy-N-methyl-4-penteneamide.

A solution Compound J (2.9 g, 13 mmol) in $CHCl_3$ (55 mL) at 0° C. was treated sequentially with N,O-dimethylhydroxylamine hydrochloride (1.4 g, 15 mmol), 1-hydroxybenzotriazole (2.0 g, 15 mmol), 4-methylmorpholine (4.4 mL, 40 mmol), and 1-(3-dimethylaminopropyl)-3-ethylcarbodiimide hydrochloride (3.4 g, 18 mmol). The reaction mixture was gradually warmed to 25° C., stirred for 16 h, and diluted with $H_2O$ (100 mL). The two layers were separated and the aqueous phase was extracted with EtOAc (3×75 mL). The combined organic phases were washed with aqueous 5% HCl (100 mL), saturated aqueous $NaHCO_3$ (100 mL), saturated aqueous NaCl (100 mL), dried ($Na_2SO_4$), and concentrated in vacuo. Flash chromatography ($SiO_2$, 3.0×20 cm, 25–50% EtOAc-hexane gradient elution) afforded Compound K (2.5 g, 71%) as a colorless oil. MS ($ESI^+$): 258.9 $(M+H)^+$, 202.9 (M-isobutylene), 158.9 (M-BOC); MS($ESI^-$): 257.2 $(M-H)^-$.

L. (S)-3-[N-[(tert-Butyloxy)carbonyl]amino]-hexen-2-one.

A solution of Compound K (2.5 g, 1.0 mmol) in THF (65 mL) at 0° C. was treated with methylmagnesium bromide (3.0 M in $Et_2O$, 8.1 mL, 2.4 mmol). The reaction mixture was stirred at 0° C. (2.5 h) and carefully poured into saturated aqueous $NH_4Cl$ (100 mL). The two layers were separated and the aqueous phase was extracted with EtOAc (3×75 mL). The combined organic extracts were washed with saturated aqueous $NH_4Cl$ (75 mL), $H_2O$ (75 mL), saturated aqueous NaCl (75 mL), dried ($MgSO_4$), and concentrated in vacuo. Flash chromatography ($SiO_2$, 3.0×20 cm, 10–25% EtOAc-hexane gradient elution) afforded (S)-2-[N-[(tert-Butyloxy)carbonyl]amino]-5-hexene-2-one (2.2 g, 67%) as a colorless oil. MS ($ESI^+$): 213.9 $(M+H)^+$, 157.9 (M-isobutylene), 113.9 (M-BOC); MS($ESI^-$): 212.2 $(M-H)^-$.

M. (S)-4-[3-[N-[(tert-Butyloxy)carbonyl]amino]-2-methyl-1(E),5-hexadienyl]-2-methylthiazole.

A solution of 2-methyl-4-thiazolylmethyl diphenylphosphine oxide (2.5 g, 8.0 mmol, Danishefsky et al. J. Org. Chem. 1996, 61, 7998) in THF (38 mL) at −78° C. was treated with n-butyllithium (1.6 M in hexane, 5.2 mL, 8.4 mmol) dropwise over 5 min. The resulting brilliant orange mixture was stirred for 15 min at −78° C., and treated with a solution of Compound L (0.81 g, 3.8 mmol) in THF (5 mL). After 10 min at −78° C., the cooling bath was removed and the reaction mixture was allowed to warm to 25° C. (2 h). The mixture was poured into saturated aqueous $NH_4Cl$ (50 mL) and the two layers were separated. The aqueous phase was extracted with $Et_2O$ (3×50 mL) and the combined organic extracts were washed successively with $H_2O$ (75 mL), saturated aqueous $NaHCO_3$ (75 mL), saturated aqueous NaCl (75 mL), dried ($Na_2SO_4$), and concentrated in vacuo. Flash chromatography ($SiO_2$, 4.0×30 cm, 10–20% EtOAc-hexane gradient elution) afforded Compound M (0.23 g, 18%) as a colorless oil along with recovered starting ketone (20–30%). MS ($ESI^+$): 309.1 $(M+H)^+$, 253.0 (M-isobutylene); MS($ESI^-$): 307.3 $(M-H)^-$.

N. (S)-4-(3-Amino-2-methyl-1(E),5-hexadienyl)-2-methylthiazole.

Compound M (0.15 g, 0.49 mmol) was treated with 4.0 N HCl in 1,4-dioxane (5 mL) at 0° C. (30 min) under Ar. The volatiles were removed in vacuo, and the resulting white foam was dissolved in cold saturated aqueous $NaHCO_3$ (3 mL). The solution was extracted with EtOAc (4×10 mL), and the combined EtOAc layers were dried ($Na_2SO_4$) and concentrated in vacuo. Flash chromatography ($SiO_2$, 1.0×5 cm, 5–10% MeOH—$CHCl_3$ gradient elution) afforded Compound N (88 mg, 88%) as a colorless oil. MS ($ESI^+$): 209.0 $(M+H)^+$; MS($ESI^-$): 207.2 $(M-H)^-$.

O. (3S,6R,7S,8S)-N-(S)-[1-(2-Methyl-4-thiazolyl)-2-methyl-1(E),5-hexadien-3-yl]-3-tert-butyldimethylsiloxy-4,4,6,8-tetramethyl-7-hydroxy-5-oxo-12-trideceneamide.

A solution of Compound N (88 mg, 0.42 mmol) in DMF (1.3 mL) at 0° C. was treated sequentially with Compound I (0.15 g, 0.35 mmol), 1-hydroxybenzotriazole (49 mg, 0.36 mmol), and 1-(3-dimethylaminopropyl)-3-ethylcarbodiimide hydrochloride (0.10 g, 0.52 mmol). The reaction mixture was gradually warmed to 25° C., stirred for 15 h, and diluted with $H_2O$ (3 mL). The mixture was extracted with EtOAc (3×10 mL), an the combined organic phases were washed with aqueous 5% HCl (10 mL), saturated aqueous $NaHCO_3$ (10 mL), saturated aqueous NaCl (10 mL), dried ($Na_2SO_4$), and concentrated in vacuo. Flash chromatography ($SiO_2$, 1.5×20 cm, 2.5% MeOH—$CHCl_3$) afforded Compound O (0.17 g, 77%) as a white foam. MS ($ESI^+$): 619.3 $(M+H)^+$.

P. [4S-[4R*,7S*,8R*,9R*,15R*(E)]]-4tert-Butyldimethylsiloxyhydroxy-5,5,7,9-tetramethyl-16-[1-methyl-2-(2-methyl-4-thiazolyl)ethenyl]-1-aza-13(E)-cyclohexadecene-2,6-dione.

A solution of Compound O (17 mg, 27 mmol) in degassed benzene (8.0 mL) was treated with Grubb's catalyst [bis (tricyclohexylphosphine)benzylidine ruthenium dichloride, Strem Chemicals, 11 mg, 14 mmol) under Ar. The reaction mixture was stirred at 25° C. for 15 h and treated again with an additional portion of catalyst (5.0 mg, 4.5 mmol). After 7 additional hours, the benzene was removed in vacuo, and the black viscous residue was passed through a pad of silica gel (1.0×3 cm) eluting with $Et_2O$ (25 mL). The eluent was concentrated in vacuo to afford a separable 5:1 (E/Z) mixture of geometric isomers. PTLC ($SiO_2$, 1 mm plate, 2 elutions with a 1:1:1 solution of hexane-toluene-ethyl acetate) afforded the E-isomer Compound P (5.1 mg, 34%) and the corresponding Z-isomer (1.0 mg, 6.7%). For Compound P: MS ($ESI^+$): 1181.7 $(2M+H)^+$, 591.4 $(M+H)^+$. For the Z-isomer: MS ($ESI^+$): 1181.5 $(2M+H)^+$, 613.2 $(M+Na)^+$, 591.2 $(M+H)^+$; MS ($ESI^-$): 589.3 $(M-H)^-$.

Q. [4S-[4R*,7S*,8R*,9R*,15R*(E)]]-4,8-Dihydroxy-5,5,7,9-tetramethyl-16-[1-methyl-2-(2-methyl-4-thiazolyl)ethenyl]-1-aza-13(E)-cyclohexadecene-2,6-dione.

To a 1 dram vial charged with Compound P (2.3 mg, 3.9 mmol) in $CH_2Cl_2$ (0.4 mL) at 0° C. was added trifluoroacetic acid (0.1 mL). The reaction mixture was sealed under a blanket of Ar and stirred at 0° C. After 4 h, the volatiles were removed under a constant stream of Ar at 0° C. Saturated aqueous $NaHCO_3$ (1 mL) and EtOAc (1 mL) were added to the residue and the two layers were separated. The aqueous phase was extracted with EtOAc (4×1 mL), and the combined EtOAc layers were dried ($Na_2SO_4$) and concentrated in vacuo. PTLC ($SiO_2$, 20×10×0.025 cm, eluting with 5% MeOH—$CHCl_3$) afforded [4S-[4R*,7S*,8S*,9R*,15R*(E)]]-4,8-dihydroxy-5,5,7,9-tetramethyl-16-[1-methyl-2-(2-methyl-4-thiazolyl)ethenyl]-1-aza-13(E)-cyclohexadecene-2,6-dione (1.3 mg, 68%) as a white film. MS ($ESI^+$): 953.5 $(2M+H)^+$, 477.3 $(M+H)^+$; MS ($ESI^-$): 475.5 $(M-H)^-$.

EXAMPLE 2

The following compounds can be made following the reaction schemes previously disclosed:

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4,13,17-trioxabicyclo[14.1.0]heptadecane-5,9-dione;

[1S[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-4,13,17-trioxabicyclo[14.1.0]heptadecane-5,9-dione;

[4S-[4R*,7S*,8R*,9R*,15R*(E)]]-4,8-Dihydroxy-5,5,7,9,13-pentamethyl-16-[1-methyl-2-(2-methyl-4-thiazolyl)ethenyl]-1,10-dioxa-13-cyclohexadecene-2,6-dione;

[4S-[4R*,7S*,8R*,9R*,15R*(E)]]-4,8-Dihydroxy-5,5,7,9-tetramethyl-16-[1-methyl-2-(2-methyl-4-thiazolyl)ethenyl]-1,10-dioxa-13-cyclohexadecene-2,6-dione;

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4,14,17-trioxabicyclo[14.1.0]heptadecane-5,9-dione;]

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-4,14,17-trioxabicyclo[14.1.0]heptadecane-5,9-dione;

[4S-[4R*,7S*,8R*,9R*,15R*(E)]]-4,8-Dihydroxy-5,5,7,9,13-pentamethyl-16-[1-methyl-2-(2-methyl-4-thiazolyl)ethenyl]-1,11-dioxa-13-__cyclohexadecene-2,6-dione;

[4S-[4R*,7S*,8R*,9R*,15R*(E))]]-4,8-Dihydroxy-5,5,7,9-tetramethyl-16-[1-methyl-2-(2-methyl-4-thiazolyl)ethenyl]-1,11-dioxa-13-cyclohexadecene-2,6-dione;

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4,17-dioxabicyclo[14.1.0]heptadecane-9-one;

1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-4,17-dioxabicyclo[14.1.0]heptadecane-9-one;

[1S-[1R*,3R*(E),7R*,10S*,11R*,12R*,16S*]]-7,11-Dihydroxy-3,8,8,10,12,16-hexamethyl-3-[1-methyl-2-(2-methyl-4-thiazolyl)ethenyl]-4,17-dioxabicyclo[14.1.0]heptadecane-5,9-dione;

[1S-[1R*,3R*(E),7R*,10S*,11R*,12R*,16S*]]-7,11-Dihydroxy-3,8,8,10,12-pentamethyl-3-[1-methyl-2-(2-methyl-4-thiazolyl)ethenyl]-4,17-dioxabicyclo[14.1.0]heptadecane-5,9-dione;

[4S-[4R*,7S*,8R*,9R*,15R*(E)]]-4,8-Dihydroxy-5,5,7,9,13,16-hexamethyl-16-[1-methyl-2-(2-methyl-4-thiazolyl)ethenyl]-1-oxa-13-cyclohexadecene-2,6-dione;

[4S-[4R*,7S*,8R*,9R*,15R*(E)]]-4,8-Dihydroxy-5,5,7,9,16-pentamethyl-16-[1-methyl-2-(2-methyl-4-thiazolyl)ethenyl]-1-oxa-13-cyclohexadecene-2,6-dione;

[1S-[1R*,3R*(E),7R*,10S*,11R*,12R*,16S*]]-7,11-Dihydroxy-6,8,8,10,12,16-hexamethyl-3-[1-methyl-2-(2-methyl-4-thiazolyl)ethenyl]-4,17-dioxabicyclo[14.1.0]heptadecane-5,9-dione;

[1S-[1R*,3R*(E),7R*,10S*,11R*,12R*,16S*]]-7,11-Dihydroxy-6,8,8,10,12-pentamethyl-3-[1-methyl-2-(2-methyl-4-thiazolyl)ethenyl]-4,17-dioxabicyclo[14.1.0]heptadecane-5,9-dione; ethenyl]-1-aza-13-cyclohexadecene-2,6-dione;

[1S-[1R*,3R*(E),7R*,10S*,11R*,12R*,16S*]]-7,11-Dihydroxy-4,8,8,10,12,16-hexamethyl-3-[1-methyl-2-(2-methyl-4-thiazolyl)ethenyl]-4-aza-17-oxabicyclo[14.1.0]heptadecane-5,9-dione;]

[1S-[1R*,3R*(E),7R*,10S*,11R*,12R*,16S*]]-7,11-Dihydroxy-4,8,8,10,12[-pentamethyl-3-[1-methyl-2-(2-methyl-4-thiazolyl)ethenyl]-4-aza-17-oxabicyclo[14.1.0]heptadecane-5,9-dione;

[4S-[4R*,7S*,8R*,9R*,15R*(E)]]-4,8-Dihydroxy-1,5,5,7,9,13-hexamethyl-16-[1-methyl-2-(2-methyl-4-thiazolyl)ethenyl]-1-aza-13-cyclohexadecene-2,6-dione;

[4S-[4R*,7S*,8R*,9R*,15R*(E)]]-4,8-Dihydroxy-1,5,5,7,9-pentamethyl-16-[1-methyl-2-(2-methyl-4-thiazolyl)ethenyl]-1-aza-13-cyclohexadecene-2,6-dione;

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-13-aza-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-13-aza-4,17-dioxabicyclo[14.1.0]heptadecane-5,9-dione;

[4S-[4R*,7S*,8R*,9R*,15R*(E)]]-4,8-Dihydroxy-5,5,7,9,13-pentamethyl-16-[1-methyl-2-(2-methyl-4-thiazolyl)ethenyl]-10-aza-1-oxa-13-cyclohexadecene-2,6-dione;

[4S-[4R*,7S*,8R*,9R*,15R*(E)]]-4,8-Dihydroxy-5,5,7,9-tetramethyl-16-[1-methyl-2-(2-methyl-4-thiazolyl)ethenyl]-10-aza-1-oxa-13-__cyclohexadecene-2,6-dione;

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-14-aza-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-14-aza-4,17-dioxabicyclo[14.1.0]heptadecane-5,9-dione;

[4S-[4R*,7S*,8R*,9R*,15R*(E)]]-4,8-Dihydroxy-5,5,7,9,13-pentamethyl-16-[1-methyl-2-(2-methyl-4-thiazolyl)ethenyl]-11-aza-1-oxa-13-cyclohexadecene-2,6-dione; 2

[4S-[4R*,7S*,8R*,9R*,15R*(E)]]-4,8-Dihydroxy-5,5,7,9-tetramethyl-16-[1-methyl-2-(2-methyl-4-thiazolyl)ethenyl]-11-aza-1-oxa-13-cyclohexadecene-2,6-dione;

[1S-[1R*,3R*,7R*,10S*,11R*,12R*,16S*]]-N-Phenyl-7,11-dihydroxy-8,8,10,12,16-pentamethyl-5,9-dioxo-4,17-dioxabicyclo[14.1.0]heptadecane-3-carboxamide;

[1S-[1R*,3R*,7R*,10S*,11R*,12R*,16S*]]-N-Phenyl-7,11-dihydroxy-8,8,10,12-tetramethyl-5,9-dioxo-4,17-dioxabicyclo[14.1.0]heptadecane-3-carboxamide;

[4S-[4R*,7S*,8R*,9R*,15R*]]-N-Phenyl-4,8-dihydroxy-5,5,7,9,13-pentamethyl-2,6-dioxo-1-oxa-13-cyclohexadecene-16-carboxamide;

[4S-[4R*,7S*,8R*,9R*,15R*]]-N-Phenyl-4,8-dihydroxy-5,5,7,9-tetramethyl-2,6-dioxo-1-oxa-13-cyclohexadecene-16-carboxamide.

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)cyclopropyl]-4,17-dioxabicyclo[14.1.0]heptadecane-5,9-dione.

[1S-[R*,3R*(E),7R*,10S*,11R*,12R*,16S*]]-7,11-Dihydroxy-8,8,10,12-tetramethyl-3-[1-methyl-2-(2-methyl-4-thiazolyl)cyclopropyl]-4,17-dioxabicyclo[14.1.0]heptadecane-5,9-dione.

EXAMPLE 3

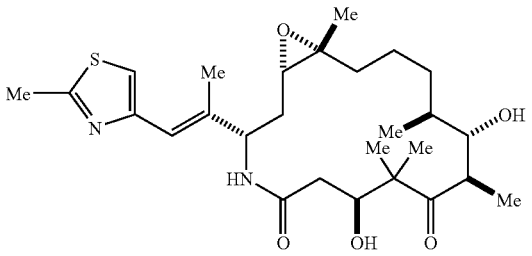

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione.

A. (3S,6R,7S,8S,12R,13S,15S)-15-Azido-12,13-epoxy-4,4,6,8,12,16-hexamethyl-7-hydroxy-17-(2-methyl-4-thiazolyl)-5-oxo-16-heptadecenoic acid.

A solution of epothilone B (0.35 g, 0.69 mmol) in degassed THF (4.5 mL) was treated with a catalytic amount (80 mg, 69 mmol) of tetrakis(triphenylphosphine) palladium (0) and the suspension was stirred at 25° C., under Ar for 30 min. The resulting bright yellow, homogeneous solution was treated all at once with a solution of sodium azide (54 mg, 0.83 mmol) in degassed $H_2O$ (2.2 mL). The reaction mixture was warmed to 45° C. for 1 h, diluted with $H_2O$ (5 mL) and extracted with EtOAc (4×7 mL). The organic extracts were washed with saturated aqueous NaCl (15 mL), dried ($Na_2SO_4$), and concentrated in vacuo. The residue was purified by flash chromatography ($SiO_2$, 3.0×15 cm, 95:5.0:0.5 $CHCl_3$—MeOH—AcOH) to afford Compound A (0.23 g, 61%) as a colorless oil. MS ($ESI^+$): 551 $(M+H)^+$; MS($ESI^-$): 549 $(M-H)^-$.

B. (3S,6R,7S,8S,12R,13S,15S)-15-Amino-12,13epoxy-4,4,6,8,12,16-hexamethyl-7-hydroxy-17-(2-methyl-4-thiazolyl)-5-oxo-16-heptadecenoic acid.

A solution of Compound A (0.23 g, 0.42 mmol) in THF (4.0 mL) was treated with $H_2O$ (23 mL, 1.25 mmol) and polymer supported triphenylphosphine (Aldrich, polystyrene cross-linked with 2% DVB, 0.28 g, 0.84 mmol) at 25° C. The resulting suspension was stirred at 25° C. under Ar (32 h), filtered through a Celite pad and concentrated in vacuo. The residue was purified by flash chromatography ($SiO_2$, 1.5×10 cm, 95:5.0:0.5 to 90:10:1.0 $CHCl_3$—MeOH—AcOH gradient elution) to afford Compound B (96 mg, 44%) as a colorless oil. MS ($ESI^+$): 525.2 $(M+H)^+$; MS($ESI^-$): 523.4 $(M-H)^-$.

Alternatively, to a 25 mL round-bottom flask charged with Compound A (0.26 g, 0.47 mmol) and $PtO_2$ (0.13 g, 50 wt %) was added absolute EtOH under Ar. The resulting black mixture was stirred under one atmosphere of $H_2$ for 10 h, after which time the system was purged with $N_2$ and an additional portion of $PtO_2$ (65 mg, 25 wt %) was added. Once again the reaction mixture was stirred under a blanket of $H_2$ for 10 h. The system was then purged with $N_2$, and the reaction mixture was filtered through a Celite pad eluting with $CH_2Cl_2$ (3×25 mL). The solvents were removed in vacuo and the residue was purified as described above to afford Compound B (0.19 g, 75%).

Alternatively, a solution of Compound A (20 mg, 36 mmol) in THF (0.4 mL) was treated with triphenylphosphine (19 mg, 73 mmol) under Ar. The reaction mixture was warmed to 45° C., stirred for 14 h and cooled to 25° C. The resulting iminophosphorane was treated with ammonium hydroxide (28%, 0.1 mL) and once again the reaction mixture was warmed to 45° C. After 4 h, the volatiles were removed in vacuo and the residue was purified as described above to afford Compound B (13 mg, 70%).

C. [1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione.

A solution of Compound B (0.33 g, 0.63 mmol) in degassed DMF (250 mL) was treated with solid $NaHCO_3$ (0.42 g, 5.0 mmol) and diphenylposphoryl azide (0.54 mL, 2.5 mmol) at 0° C. under Ar. The resulting suspension was stirred at 4° C. for 24 h, diluted with phosphate buffer (250 mL, pH=7) at 0° C. and extracted with EtOAc (5×100 mL). The organic extracts were washed with 10% aqueous LiCl (2×125 mL), dried ($Na_2SO_4$) and concentrated in vacuo. The residue was first purified by flash chromatography ($SiO_2$, 2.0×10 cm, 2–5% MeOH—$CHCl_3$ gradient elution) and then repurified using a Chromatotron (2 mm $SiO_2$, GF rotor, 2–5% MeOH—$CHCl_3$ gradient elution) to afford the title compound (0.13 g, 40%) as a colorless oil: $^1H$ NMR ($CDCl_3$, 400 MHz) δ 6.98 (s, 1H), 6.71 (d, 1H, NH, J=8.1 Hz), 6.56 (s, 1H), 4.69–4.62 (m, 1H), 4.18–4.12 (m, 1H), 4.01–3.96 (m, 1H), 3.86 (s, 1H), 3.38–3.34 (m, 1H), 2.82 (dd, 1H, J=5.6, 6.0 Hz), 2.71 (s, 3H), 2.58 (s, 1H), 2.43 (dd, 1H, J=9.0, 14.5 Hz), 3.34 (dd, 1H, J=3.0, 14.5 Hz), 2.14 (s, 3H), 2.05–1.92 (m, 2 H), 1.82–1.41 (a series of multiplets, 7H), 1.35 (s, 3H), 1.28 (s, 3H), 1.18 (d, 3H, J=6.8 Hz), 1.14 (s, 3H), 1.00 (d, 3H, J=6.8 Hz); MS ($ESI^+$): 507.2 $(M+H)^+$; MS($ESI^-$): 505.4 $(M-H)^-$.

EXAMPLE 4

Process for reduction of oxirane ring of epothilone and epothilone analogs.

To a two-necked flask was added chopped pieces of magnesium turnings (24 mg, 1.0 mmol). The flask was flame-dried under vacuum and cooled under argon. Bis (cyclopentadienyl)titanium dichloride (250 mg, 1.0 mmol) was added followed by anhydrous THF (5 mL). The stirring suspension was evacuated with low vacuum, and the reaction flask was refilled with argon. The red suspension became dark, turning a homogeneous deep green after 1.5 h with nearly all the magnesium metal being consumed. An aliquot (3.5 mL, 0.70 mmol, 3.5 eq) was removed and cooled to −78° C. under argon. To this solution was added epothilone A (99 mg, 0.20 mmol, 1.0 eq). The reaction mixture was warmed to room temperature and stirred for 15 min. The volatiles were removed in vacuo and the residue was chromatographed two times on silica (25 g), eluting with 35% EtOAc/hexanes to give 76 mg (80%) of epothilone C as a pale yellow viscous oil.

EXAMPLE 5

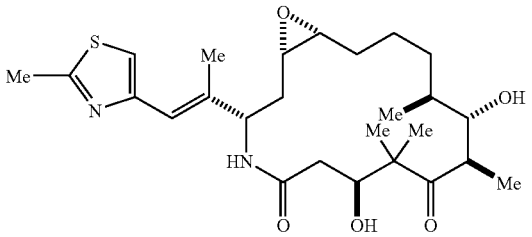

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-4-aza-17-oxabicyclo[14.1.0]heptadecane-5,9-dione.

A. (3S,6R,7S,8S,12R,13S,15S)-15-Azido-3,7-dihydroxy-12,13-epoxy-4,4,6,8,16-pentamethyl-17-(2-methyl-4-thiazolyl)oxo-16(E)-heptadecenoic acid.

Tetrakis(triphenylphosphine)palladium(0) (1.17 g, 1.01 mmol, 0.10 eq) was added to a solution of epothilone A (4.97 g, 10.1 mmol, 1.0 eq) in degassed THF (100 ml) at room temperature and was stirred for 30 minutes under argon. Sodium azide (0.980 g, 15.1 mmol, 1.5 eq) was added to the above reaction mixture followed by the addition of degassed water (10 ml). The reaction mixture was heated to 45° C. for one hour, cooled to room temperature, diluted with ethyl acetate (300 ml) and further diluted with water (150 ml). The aqueous layer was extracted with ethyl acetate (3×100 ml). The combined organic extracts were washed with brine (150 ml), dried (sodium sulfate), filtered and concentrated under vacuum. The oily residue was purified by flash silica gel chromatography (eluting 0–5% methanol/chloroform with 0.1% of acetic acid) to afford Compound A (1.84 g, 34.0% yield) as glassy solid. MS ($ESI^+$): 537 $(M+H)^+$; MS ($ESI^-$): 535 $(M-H)^-$ B. (3S,6R,7S,8S,12R,13S,15S)-15-Amino-3,7-dihydroxy-12,13-epoxy-4,4,6,8,16-pentamethyl-17-(2-methyl-4-thiazolyl)-5-oxo-16(E)-heptadecenoic acid.

Platinum oxide (0.980 g, 4.30 mmol, 1.25 eq) was added to a solution of Compound A (1.85 g, 3.44 mmol, 1.0 eq) in absolute ethanol (137 ml). The reaction mixture was stirred vigorously under a hydrogen balloon for 16 hours at room temperature. The reaction mixture was filtered and the filtrate was concentrated under vacuum. The oily residue was purified by preparative HPLC (YMC S-15 ODS 50×500 mm column, 45 minutes/gradient, 0–100% B, 50 ml/min, retention time=17 minutes, A=0.1% acetic acid /5% acetonitrile/95% water, B=0.1% acetic acid/5% water/95% acetonitrile). The appropriate fractions were concentrated under vacuum and the residue was lyophilized from aqueous acetonitrile to afford Compound B (1.33 g, 76.0% yield) as a colorless solid. MS ($ESI^+$): $511(M+H)^+$; MS ($ESI^-$): $509\ (M-H)^-$ C. [1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-4-aza-17-oxabicyclo[14.1.0]heptadecane5,9-dione.

Compound Compound B (0.860 g, 1.68 mmol, 1.0 eq) was dissolved in anhydrous DMF (0.00250M, 672 ml) and degassed for one hour at room temperature. The solution was cooled to 0° C., and anhydrous sodium bicarbonate (1.13 g, 13.4 mmol, 4.0 eq) and diphenylphosphoryl azide (1.85 g, 6.72 mmol, 8.0 eq) were added under argon. The reaction mixture was kept at 4° C. under argon and stirred 16 hours. The reaction mixture was then cooled to −60° C., and pH 7 phosphate buffer (400 ml) was added slowly to quench the reaction. Temperature was kept below −30° C. The above mixture was allowed to warm to room temperature slowly and extracted with ethyl acetate (1 liter). The aqueous layer was washed with ethyl acetate (4×300 ml). The organic extracts were combined, washed with 10% LiCl (500 ml), dried (sodium sulfate), filtered and concentrated under vacuum. The oily residue was purified by preparative HPLC (YMC S-15 ODS 50×500 mm column, 45 minutes/gradient, 0–100% B, 50 ml/min, retention time=35 minutes, A=5% acetonitrile/95% water, B=5% water/95% acetonitrile). The appropriate fractions were concentrated under vacuum and the residue was lyophilized from aqueous acetonitrile to afford title compound (0.220 g, 26.0% yield) as a colorless solid. MS ($ESI^+$): 493 $(M+H)^+$; MS ($ESI^-$): 491 $(M-H)^-$

EXAMPLE 6

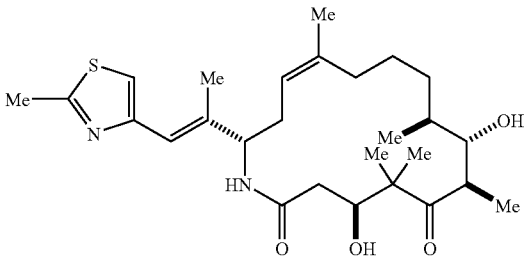

[4S-[4R*,7S*,8R*,9R*,15R*(E)]]-4,8-Dihydroxy-5,5,7,9,13-pentamethyl-16-[1-methyl-2-(2-methyl-4-thiazolyl)ethenyl]-1-aza-13(Z)-cyclohexadecene-2,6dione.

Tungsten hexachloride (0.19 g, 0.49 mmol, 0.5 equiv) was dissolved in THF (5.0 ml) and the solution was cooled to −78° C. n-Butyllithium in hexane (1.6M, 0.63 ml, 1.0 mmol, 1.0 equiv) was added in one portion and the reaction mixture was allowed to warm to room temperature over 20 minutes (the solution turned dark green upon warming to rt). A 0.1M solution of the prepared tungsten reagent (0.79 ml, 0.079 mmol, 2.0 mmol) was added to Compound 4C (0.020 g, 0.039 mmol, 1.0 equiv) at room temperature. The reaction mixture was stirred a room temperature for 30 minutes and then was quenched with saturated $NaHCO_3$ (2.0 ml). The quenched solution was diluted with water (10 ml) and the solution was extracted with $CH_2Cl_2$ (4×20 ml). The combined organic extracts were dried ($Na_{SO4}$), filtered and concentrated under vacuum. The inorganics were removed by passing the residue through a silica gel plug (eluting with 19/1 $CHCl_3$/MeOH). The eluent was concentrated under vacuum. The residue was purified by phplc (YMC-S5 ODS, 30–100% B, A=5% aq $CH_3CN$, B=95% aqueous $CH_3CN$, 3 ml/min., 220 nm., 30 min. gradient) and the appropriate fractions were concentrated under vacuum. The sticky solid was lyophilized from aqueous acetonitrile to afford title compound (4.3 mg, 29%) as a white solid. TLC: Rf=0.57 (9/1 CHCl3/MeOH, visualization by UV); HRMS: (M+H)+calc=491.29436, found=491.2934

EXAMPLE 7

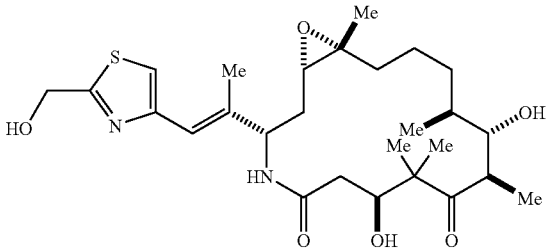

[1S-[1R*,3R*(E),7R*,10S*,11R*,12R*,16S*]]-7,11-Dihydroxy-8,8,10,12,16-pentamethyl-3-[1-methyl-2-(2-hydroxymethyl-4-thiazolyl)ethenyl]-4-aza-17-oxabicyclo[14.1.0]heptadecane-5,9-dione.

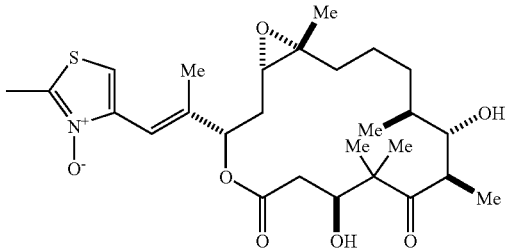

A. [1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4,17-dioxabicyclo[14.1.0]heptadecane-5,9-dione, N-oxide.

A solution of epothilone B (2.0 g, 3.9 mmol) in $CH_2Cl_2$ (30 mL) was treated with 3-chloroperoxybenzoic acid (1.0 g, 5.9 mmol) at 25° C., under Ar for 2 h. An additional 0.5 g (3.0 mmol) of 3-chloroperoxybenzoic acid was added and the reaction mixture was then stirred for 2 h. The reaction mixture was filtered and the filtrate was concentrated in vacuo. The residue was dissolved in EtOAc (100 mL), washed with saturated aqueous $NaHCO_3$ (75 mL), 5% aqueous $Na_2SO_3$ (75 mL), $H_2O$ (75 mL), dried ($Na_2SO_4$) and concentrated in vacuo. The residue was purified by flash chromatography ($SiO_2$, 4.5×30 cm, 2–10% MeOH—$CHCl_3$ gradient elution) to afford Compound A (1.04 g, 50%) as a white solid. MS ($ESI^+$): 524.3 $(M+H)^+$; MS ($ESI^-$): 522.5 $(M-H)^-$.

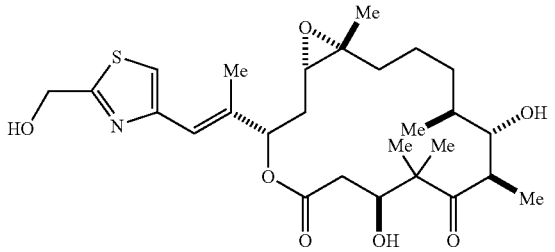

B. [1S-[1R*,3R*(E),7R*,10S*,11R*,12R*,16S*]]-7,11-Dihydroxy-8,8,10,12,16-pentamethyl-3-[1-methyl-2-(2-hydroxymethyl-4-thiazolyl)ethenyl]-4,17-dioxabicyclo[14.1.0]heptadecane-5,9-dione, [Epothilone F]. To a solution of compound A (0.46 g, 0.88 mmol) in $CH_2Cl_2$ (10 mL) in a resealable tube was added 2,6-lutidine (0.82 mL, 7.0 mmol) and trifluoroacetic anhydride (0.87 mL, 6.2 mmol) under Ar. The reaction vessel was sealed under Ar, heated to 75° C. (12 min), cooled to 25° C., and the volatiles were removed under a steady stream of $N_2$. The reaction tube was then placed on a high vacuum pump for 15 min. The resulting residue was dissolved in MeOH (10 mL) and treated with ammonium hydroxide (28–30% $NH_4$ in $H_2O$, 1.0 mL). The mixture was heated to 45° C. (10 min), and the volatiles were removed in vacuo. The crude reaction mixture was purified by HPLC (YMC S-15 ODS 30×500 mm column, 50% acetonitrile-$H_2O$ isocratic conditions, flow rate=20 mL/min, retention time=28 min). The appropriate fractions were concentrated under vacuum and the residue was lyophilized from aqueous acetonitrile to afford Compound B (0.22 g, 48%) as a white solid. MS ($ESI^+$): 524.3 $(M+H)^+$, 1047.6 $(2M+H)^+$; MS ($ESI^-$): 522.5 $(M-H)^-$.

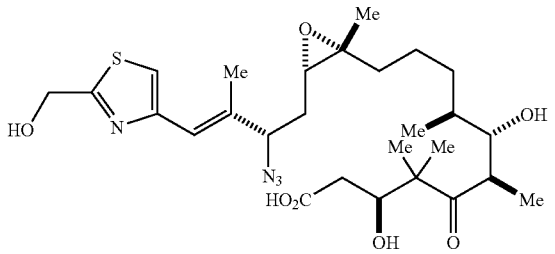

C. (3S,6R,7S,8S,12R,13S,15S)-15-Azido-3,7-Dihydroxy-12,13-epoxy-4,4,6,8,12,16-hexamethyl-17-(2-hydroxymethyl-4-thiazolyl)-5-oxo-16(E)-heptadecenoic acid. A solution of Compound B (0.18 g, 0.34 mmol) in degassed THF (3.0 mL) was treated with a catalytic amount (40 mg, $3.4\times10^{-2}$ mmol) of tetrakis(triphenylphosphine) palladium(0) and the suspension was stirred at 25° C., under Ar for 30 min. The resulting bright yellow, homogeneous solution was treated all at once with a solution of sodium azide (27 mg, 0.41 mmol) in degassed $H_2O$ (1.5 mL). The reaction mixture was warmed to 45° C. for 1 h, diluted with $H_2O$ (5 mL) and extracted with EtOAc (4×10 mL). The organic extracts were washed with saturated aqueous NaCl (15 mL), dried ($Na_2SO_4$), and concentrated in vacuo. The residue was purified by flash chromatography ($SiO_2$, 2.5×15 cm, 95:5 $CHCl_3$—MeOH to 95:5.0:0.5 $CHCl_3$—MeOH—AcOH gradient elution) to afford Compound C (39 mg, 20%) as a colorless oil. MS ($ESI^+$): 567.4 $(M+H)^+$, 1133.6 $(2M+H)^+$; MS ($ESI^-$): 565.5 $(M-H)^-$, 1131.8 $(2M-H)^-$.

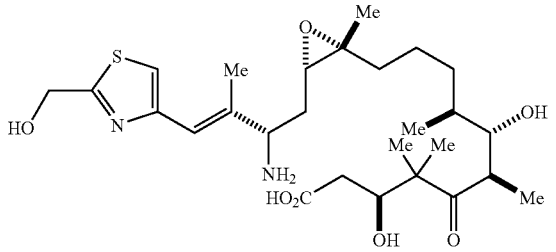

D. (3S,6R,7S,8S,12R,13S,15S)-15-Amino-3,7dihydroxy-12,13-epoxy-4,4,6,8,12,16-hexmethyl-17-(2-hydroxymethyl-4-thiazolyl)-5-oxo-16(E)-heptadecenoic acid. To a 10 mL round-bottom flask charged with compound C (40 mg, 71 mmol) and $PtO_2$ (12 mg, 30 wt %) was added absolute EtOH (3 mL) under Ar. The resulting black mixture was stirred under one atmosphere of $H_2$ for 10 h. The system was then purged with $N_2$ and the reaction mixture was filtered through a nylon membrane (washing with 25 mL of MeOH). The solvents were removed in vacuo to afford Compound D (29 mg, 76%) as a foam, which was sufficiently pure to use in the next step. LCMS: 541.3 $(M+H)^+$.

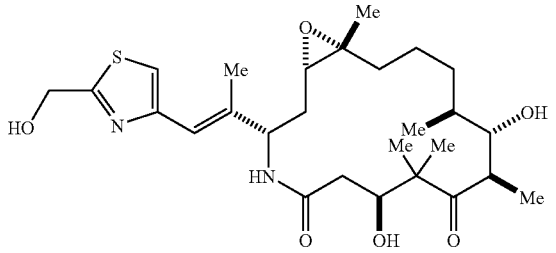

E. [1S-[1R*,3R*(E),7R*,10S*,11R*,12R*,16S*]]-7,11-Dihydroxy-8,8,10,12,16-pentamethyl-3-[1-methyl-2-(2-hydroxymethyl-4-thiazolyl)ethenyl]-4-aza-17-oxabicyclo[14.1.0]heptadecane-5,9-dione.

A solution of compound D (29 mg, 54 mmol) in degassed DMF (21 mL) was treated with solid $NaHCO_3$ (36 mg, 0.43 mmol) and diphenylphosphoryl azide (46 mL, 0.21 mmol) at 0° C. under Ar. The resulting suspension was stirred at 4° C. for 19 h, cooled to −40° C., diluted with 25 mL of pH 7 phosphate buffer (carefully adding such that the internal temperature remains below −30° C.), and extracted with EtOAc (4×10 mL). The organic extracts were washed with cold 10% aqueous LiCl (25 mL), dried ($Na_2SO_4$) and concentrated in vacuo. The residue was purified using a chromatotron (1 mm $SiO_2$ GF rotor, 2–5% MeOH—$CHCl_3$ gradient elution) to afford the title Compound E (9.1 mg, 34%) as a colorless oil. MS ($ESI^+$): 523.2 $(M+H)^+$; MS ($ESI^-$): 521.5 $(M-H)^-$.

EXAMPLE 8

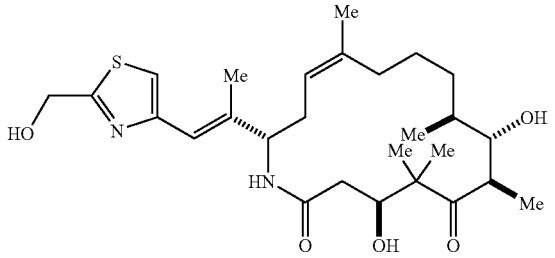

[4S-[4R*,7S*,8R*,9R*,15R*(E)]]-4,8-Dihydroxy-5,5,7,9,13-pentamethyl-16-[1-methyl-2-(2-hydroxymethyl-4-thiazolyl)ethenyl]-1-aza-13(Z)-cyclohexadecene-2,6-dione.

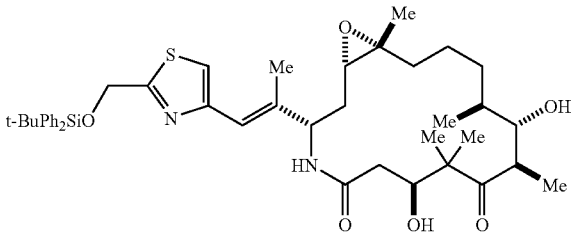

A. [1S-[1R*,3R*(E),7R*,10S*,11R*,12R*,16S*]]-7,11-Dihydroxy-8,8,10,12,16-pentamethyl-3-[1-methyl-2-(2-tert-butyldiphenylsilyloxymethyl-4-thiolyl)ethenyl]-4-aza-17-oxabicyclo[14.1.0]heptadecane-6,9-dione.

A solution of Compound 7E (6.8 mg, 13 mmol) in $CH_2Cl_2$ (0.5 mL) was treated with triethylamine (2.7 mL, 20 mmol), 4-N,N-dimethylaminopyridine (0.2 mg, 1.3 mmol) and tert-butyldiphenylsilyl chloride (3.7 mL, 14 mmol) at 0° C. under Ar. The reaction mixture was gradually warmed to 25° C. (1 h), cooled to 0° C., quenched by the addition of saturated aqueous $NaHCO_3$ (1 mL), and extracted with EtOAc (4×2 mL). The combined organic extracts were washed with brine (5 mL), dried ($Na_2SO_4$) and concentrated in vacuo. The residue was purified by flash chromatography ($SiO_2$, 1.0×5 cm, 2–5% MeOH—$CHCl_3$ gradient elution) to afford Compound A (7.0 mg, 71%) as a colorless oil. MS ($ESI^+$): 761.5 $(M+H)^+$; MS ($ESI^-$): 759.7 $(M-H)^-$.

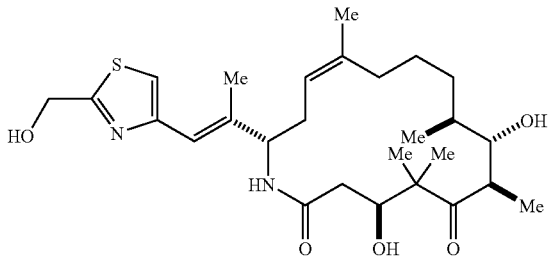

B. [4S-[4R*,7S*,8R*,9R*,16R*(E)]]-4,8-Dihydroxy-5,6,7,9,13-pentamethyl-16-[1-methyl-2-(2-hydroxymethyl-4thiazolyl)ethenyl]-1-aza-13(Z)-cyclohexadecene-2,6-dione.

A solution of tungsten(IV) chloride (0.10 g, 0.25 mmol) in anhydrous THF at −78° C. was treated with n-BuLi (1.6 M in hexanes, 0.32 mL, 0.50 mmol) under Ar. The reaction mixture was warmed to 25° C. over 40 min and then recooled to 0° C. An aliquot of the resulting deep-green, homogeneous solution (0.2 mL, 20 mmol) was added to a 1 dram vial charged with compound A (7.0 mg, 9.2 mmol) at 0° C. under Ar. The reaction mixture was warmed to 25° C., stirred for 30 min, quenched by the addition of saturated aqueous $NaHCO_3$ (0.5 mL) and extracted with EtOAc (4×1 mL). The combined organic extracts were dried ($Na_2SO_4$) and concentrated in vacuo. The residue was purified by preparative TLC ($SiO_2$, 20×20×0.025 cm, eluting with 5% MeOH—$CHCl_3$) to afford an inseparable mixture of the silyl-protected (13Z) isomer of Compound B along with a small amount (<10%) of the minor (13E) isomer, which was immediately deprotected in the next step.

The silyl-protected isomeric mixture of compound B (2.3 mg, 3.1 mmol) was treated with 0.3 mL of a buffered solution of HF-pyridine in THF (2:1:0.5 THF/pyridine/HF-pyridine solution from Aldrich Chemical Co.) at 25° C. After 1 h, the reaction mixture was neutralized with saturated aqueous $NaHCO_3$ (0.5 mL) and extracted with EtOAc (4×1 mL). The combined organic extracts were washed with saturated aqueous $NaHCO_3$ (1 mL), dried ($Na_2SO_4$) and the volatiles were removed in vacuo. The residue was purified by preparative TLC ($SiO_2$, 20×10×0.025 cm, eluting with 5% MeOH—$CHCl_3$) to afford title compound (13Z-isomer) along with an inseparable amount (<10%) of the minor (13E) isomer (0.96 mg, 20% for the two steps) as a thin film. MS ($ESI^+$): 507.3 $(M+H)^+$; MS ($ESI^-$): 505.6 $(M-H)^-$.

What is claimed:

[1. A compound of the formula:

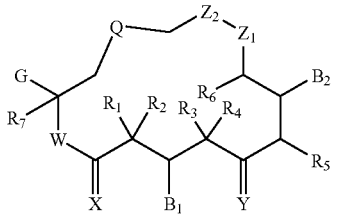

V wherein:

Q is selected from the group consisting of:

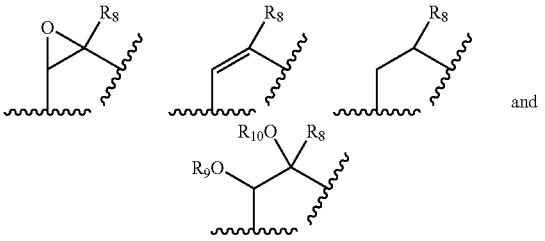

G is selected from the group consisting of alkyl; substituted alkyl; substituted aryl; a 4 to 7 membered monocyclic, 7 to 11 membered bicyclic, or 10 to 15 membered tricyclic saturated or unsaturated ring system having between 1 and 3 heteroatoms selected from nitrogen, oxygen, and sulfur;

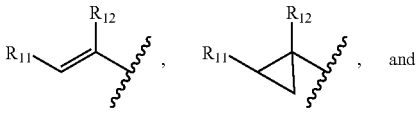

-continued

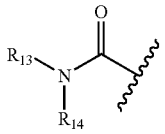

W is O or $NR_{15}$;

X is O or H, H;

Y is selected from the group consisting of O; H, $OR_{16}$; $OR_{17}$, $OR_{17}$; $NOR_{18}$; H,$NHOR_{19}$; H, $NR_{20}R_{21}$; H, H; and $CHR_{22}$; wherein $OR_{17}$, $OR_{17}$ can be a cyclic ketal;

$Z_1$ and $Z_2$ are independently $CH_2$;

$B_1$ and $B_2$ are independently selected from the group consisting of $OR_{24}$, $OCOR_{25}$, and O—C(=0)—$NR_{26}R_{27}$, and when $B_1$ is OH and Y is OH, H, they can form a six-membered ring ketal or acetal;

$R_1$, $R_2$, $R_3$, $R_4$, $R_5$, $R_7$, $R_{13}$, $R_{14}$, $R_{18}$, $R_{19}$, $R_{20}$, $R_{21}$, $R_{22}$, $R_{26}$ and $R_{27}$ are selected from the group consisting of H, alkyl, substituted alkyl, and aryl, and when $R_1$ and $R_2$ are alkyl can be joined to form a cycloalkyl, and when $R_3$ and $R_4$ are alkyl can be joined to form a cycloalkyl;

$R_6$is methyl;

$R_9$, $R_{10}$, $R_{16}$, $R_{17}$, $R_{24}$, $R_{25}$ and $R_{31}$ are selected from the group consisting of H, alkyl, and substituted alkyl;

$R_{11}$, $R_{12}$, $R_{28}$, $R_{30}$, $R_{32}$, and $R_{33}$ are selected from the group consisting of H; alkyl; substituted alkyl; aryl; substituted aryl; cycloalkyl containing 1 to 3 rings and 3 to 7 carbons per ring which may be further fused with an unsaturated $C_3$–$C_7$ carbocyclic ring; and a 4 to 7 membered monocyclic, 7 to 11 membered bicyclic, or 10 to 15 membered tricyclic saturated or unsaturated ring system having between 1 and 3 heteroatoms selected from nitrogen, oxygen, and sulfur;

$R_8$ is hydrogen or methyl;

$R_{15}$, $R_{23}$ and $R_{29}$ are selected from the group consisting of H; alkyl; substituted alkyl; aryl; substituted aryl; cycloalkyl containing 1 to 3 rings and 3 to 7 carbons per ring which may be further fused with an unsaturated $C_3$–$C_7$ carbocyclic ring; a 4 to 7 membered monocyclic, 7 to 11 membered bicyclic, or 10 to 15 membered tricyclic saturated or unsaturated ring system having between 1 and 3 heteroatoms selected from nitrogen, oxygen, and sulfur; $R_{32}C{=}O$; $R_{33}SO_2$; hydroxy; O-alkyl or O-substituted alkyl;

or pharmaceutically acceptable salts thereof, hydrates, solvates or geometric, optical or stereoisomers thereof;

with the proviso that compounds wherein

W and X are both O; and $R_1$, $R_2$ and $R_7$ are H; and $R_3$, $R_4$ and $R_6$ are methyl; and $R_8$ is H or methyl; and G is 1-methyl-2-(substituted-4-thiazolyl)ethenyl; and Q is as defined above are excluded.]

[2. The compound of claim 1 wherein

Q is

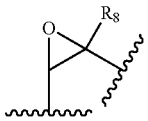

or

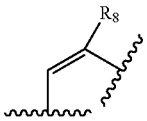

X is O;

Y is O;

$Z_1$, and $Z_2$, are $CH_2$; and

W is $NR_{15}$.]

[3. A compound selected from the group consisting of:

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4,13,17-trioxabicyclo [14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-4,13,17-trioxabicyclo [14.1.0]heptadecane-5,9-dione;

[4S-[4R*,7S*,8R*,9R*,15R*(E)]]-4,8-Dihydroxy-5,5,7,9,13-pentamethyl-16-[1-methyl-2-(2-methyl-4-thiazolyl) ethenyl]-1,10-dioxa-13-cyclohexadecene-2,6-dione;

[4S-[4R*,7S*,8R*,9R*,15R*(E)]]-4,8-Dihydroxy-5,5,7,9-tetramethyl-16-[1-methyl-2-(2-methyl-4-thiazolyl) ethenyl]-1,10-dioxa-13-cyclohexadecene-2,6-dione;

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4,14,17-trioxabicyclo [14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-4,14,17-trioxabicyclo [14.1.0]heptadecane-5,9-dione;

[4S-[4R*,7S*,8R*,9R*,15R*(E)]]-4,8-Dihydroxy-5,5,7,9,13-pentamethyl-16-[1-methyl-2-(2-methyl-4-thiazolyl) ethenyl]-1,11-dioxa-13-cyclohexadecene-2,6-dione;

[4S-[4R*,7S*,8R*,9R*,15R*(E)]]-4,8-Dihydroxy-5,5,7,9-tetramethyl-16-[1-methyl-2-(2-methyl-4-thiazolyl) ethenyl]-1,11-dioxa-13-cyclohexadecene-2,6-dione;

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4,17-dioxabicyclo [14.1.0] heptadecane-9-one;

1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-4,17-dioxabicyclo[14.1.0] heptadecane-9-one;

[1S-[1R*,3R*(E),7R*,10S*,11R*,12R*,16S*]]-7,11-Dihydroxy-3,8,8,10,12,16-hexamethyl-3-[1-methyl-2-(2-methyl-4-thiazolyl)ethenyl]-4,17-dioxabicyclo [14.1.0] heptadecane-5,9-dione;

[1S-[1R*,3R*(E),7R*,10S*,11R*,12R*,16S*]]-7,11-Dihydroxy-3,8,8,10,12-pentamethyl-3-[1-methyl-2-(2-methyl-4-thiazolyl)ethenyl]-4,17-dioxabicyclo[14.1.0] heptadecane-5,9-dione;

[4S-[4R*,7S*,8R*,9R*,15R*(E)]]-4,8-Dihydroxy-5,5,7,9,13,16-hexamethyl-16-[1-methyl-2-(2-methyl-4-thiazolyl) ethenyl]-1-oxa-13-cyclohexadecene-2,6-dione;

[4S-[4R*,7S*,8R*,9R*,15R*(E)]]-4,8-Dihydroxy-5,5,7,9,16-pentamethyl-16-[1-methyl-2-(2-methyl-4-thiazolyl) ethenyl]-1-oxa-13-cyclohexadecene-2,6-dione;

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4,17-dioxabicyclo [14.1.0] heptadecane-5,9-dione;

[1S-[1R*,3R*(E),7R*,10S*,11R*,12R*,16S*]]-7,11-Dihydroxy-6,8,8,10,12-pentamethyl-3-[1-methyl-2-(2-methyl-4-thiazolyl)ethenyl]-4,17-dioxabicyclo[14.1.0] heptadecane-5,9-dione;

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4-aza-17-oxabicyclo [14.1.0] heptadecane-5,9-dione;

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-4-aza-17-oxabicyclo [14.1.0] heptadecane-5,9-dione;

[4S-[4R*,7S*,8R*,9R*,15R*(E)]]-4,8-Dibydroxy-5,5,7,9,13-pentamethyl-16-[1-methyl-2-(2-methyl-4-thiazolyl) ethenyl]-1-aza-13-cyclohexadecene-2,6-dione;

[4S-[4R*,7S*,8R*,9R*,15R*(E)]]-4,8-Dihydroxy-5,5,7,9-tetramethyl-16-[1-methyl-2-(2-methyl-4-thiazolyl) ethenyl]-1-aza-13-cyclohexadecene-2,6-dione;

[1S-[1R*,3R*(E),7R*,10S*,11R*,12R*,16S*]]-7,11-Dihydroxy-4,8,8,10,12,16-hexamethyl-3-[1-methyl-2-(2-methyl-4-thiazolyl)ethenyl]-4-aza-17-oxabicyclo [14.1.0] heptadecane-5,9-dione;

[1S-[1R*,3R*(E),7R*,10S*,11R*,12R*,16S*]]-7,11-Dihydroxy-4,8,8,10,12,-pentamethyl-3-[1-methyl-2-(2-methyl-4-thiazolyl)ethenyl]-4-aza-17-oxabicyclo [14.1.0] heptadecane-5,9-dione;

[4S-[4R*,7S*,8R*,9R*,15R*(E)]]-4,8-Dihydroxy-1,5,5,7,9,13-hexamethyl-16-[1-methyl-2-(2-methyl-4-thiazolyl) ethenyl]-1-aza-13-cyclohexadecene-2,6-dione;

[4S-[4R*,7S*,8R*,9R*,15R*(E)]]-4,8-Dihydroxy-1,5,5,7,9,13-pentamethyl-16-[1-methyl-2-(2-methyl-4-thiazolyl) ethenyl]-1-aza-13-cyclohexadecene-2,6-dione;

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-13-aza-4,17-dioxabicyclo [14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-13-aza-4,17-dioxabicyclo [14.1.0]heptadecane-5,9-dione;

[4S-[4R*,7S*,8R*,9R*,15R*(E)]]-4,8-Dihydroxy-5,5,7,9,13-pentamethyl-16-[1-methyl-2-(2-methyl-4-thiazolyl) ethenyl]-10-aza-1-oxa-13-cyclohexadecene-2,6-dione;

[4S-[4R*,7S*,8R*,9R*,15R*(E)]]-4,8-Dihydroxy-5,5,7,9-tetramethyl-16-[1-methyl-2-(2-methyl-4-thiazolyl) ethenyl]-10-aza-1-oxa-13-cyclohexadecene-2,6-dione;

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-14-aza-4,17-dioxabicyclo [14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-14-aza-4,17-dioxabicyclo [14.1.0]heptadecane-5,9-dione;

[4S-[4R*,7S*,8R*,9R*,15R*(E)]]-4,8-Dihydroxy-5,5,7,9,13-pentamethyl-16-[1-methyl-2-(2-methyl-4-thiazolyl) ethenyl]-11-aza-1-oxa-13-cyclohexadecene-2,6-dione;

[4S-[4R*,7S*,8R*,9R*,15R*(E)]]-4,8-Dihydroxy-5,5,7,9-tetramethyl-16-[1-methyl-2-(2-methyl-4-thiazolyl) ethenyl]-11-aza-1-oxa-13-cyclohexadecene-2,6-dione;

[1S-[1R*,3R*,7R*,10S*,11R*,12R*,16S*]]-N-Phenyl-7,11-dihydroxy-8,8,10,12,16-pentamethyl-5,9-dioxo-4,17-dioxabicyclo[14.1.0]heptadecane-3-carboxamide;

[1S-[1R*,3R*,7R*,10S*,11R*,12R*,16S*]]-N-Phenyl-7,11-dihydroxy-8,8,10,12-tetramethyl-5,9-dioxo-4,17-dioxabicyclo[14.1.0]heptadecane-3-carboxamide;

[4S-[4R*,7S*,8R*,9R*,15R*]]-N-Phenyl-4,8-dihydroxy-5,5,7,9,13-pentamethyl-2,6-dioxo-1-oxa-13-cyclohexadecene-16-carboxamide;

[4S-[4R*,7S*,8R*,9R*,15R*]]-N-Phenyl-4,8-dihydroxy-5,5,7,9-tetramethyl-2,6-dioxo-1-oxa-13-cyclohexadecene-16-carboxamide;

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)cyclopropyl]-4,17-dioxabicyclo [14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)cyclopropyl]-4,17-dioxabicyclo [14.1.0]heptadecane-5,9-dione;

[4S-[4R*,7S*,8R*,9R*,15R*(E)]]-4,8-Dibydroxy-5,5,7,9,13-pentamethyl-16-[1-methyl-2-(2-hydroxymethyl-4-thiazolyl)ethenyl]-1-aza-13(Z)-cyclohexadecene-2,6-dione;

and the pharmaceutically acceptable salts, solvates and hydrates thereof.]

[4. A method of treating breast cancer, ovarian cancer, colon cancer, head and neck cancer, lung cancer, gynecological cancers, brain cancer, germ cell cancer, urothelial cancer, esophageal cancer, prostate cancer, bladder cancer, or pancreatic cancer in a patient in need of said treatment which comprises administering to said patient a therapeutically effective amount of a compound of claim 1.]

[5. The method of claim 4, wherein the cancer is cancer of the breast, ovary, or colon.]

[6. A method of treating breast cancer, ovarian cancer, colon cancer, head and neck cancer, lung cancer, gynecological cancers, brain cancer, germ cell cancer, urothelial cancer, esophageal cancer, prostate cancer, bladder cancer, or pancreatic cancer in a patient in need of said treatment which comprises administering to said patient a therapeutically effective amount of a compound of claim 2.]

[7. A method of treating breast cancer, ovarian cancer, colon cancer, head and neck cancer, lung cancer, gynecological cancers, brain cancer, germ cell cancer, urothelial cancer, esophageal cancer, prostate cancer, bladder cancer, or pancreatic cancer in a patient in need of said treatment which comprises administering to said patient a therapeutically effective amount of a compound of claim 3.]

[8. A compound having the formula:

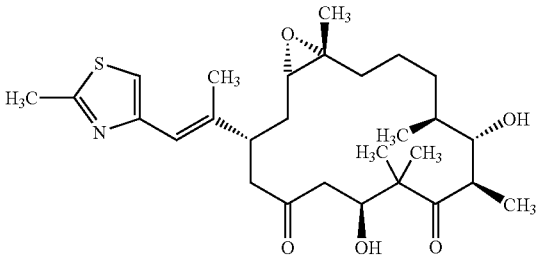

or a pharmaceutically acceptable salt, hydrate, solvate, geometrical isomer, optical isomer or stereoisomer thereof.]

[9. A method of treating breast cancer, ovarian cancer, colon cancer, head and neck cancer, lung cancer, gynecological cancers, brain cancer, germ cell cancer, urothelial cancer, esophageal cancer, prostate cancer, bladder cancer, or pancreatic cancer in a patient in need of said treatment which comprises administering to said patient a therapeutically effective amount of a compound of claim 8.]

[10. The method of claim 9, wherein the cancer is cancer of the breast, ovary, or colon.]

[11. The method of claim 6, wherein the cancer is cancer of the breast, ovary, or colon.]

[12. The method of claim 7, wherein the cancer is cancer of the breast, ovary, or colon.]

[13. The compound of claim 1, wherein G is 1-methyl-2-(substituted-4-thiazolyl) ethenyl group.]

[14. The compound of claim 1, wherein Q is

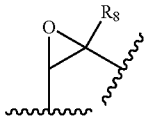

.]

[15. The compound of claim 1, wherein W is $NR_{15}$.]

[16. The compound of claim 1, wherein X and Y are each O.]

[17. A method of treating breast cancer, ovarian cancer, colon cancer, head and neck cancer, lung cancer, gynecological cancers, brain cancer, germ cell cancer, urothelial cancer, esophageal cancer, prostate cancer, bladder cancer, or pancreatic cancer in a patient in need of said treatment which comprises administering to said patient a therapeutically effective amount of a compound of claim 13.]

[18. The method of claim 17, wherein the cancer is cancer of the breast, ovary, or colon.]

[19. A method of treating breast cancer, ovarian cancer, colon cancer, head and neck cancer, lung cancer, gynecological cancers, brain cancer, germ cell cancer, urothelial cancer, esophageal cancer, prostate cancer, bladder cancer, or pancreatic cancer in a patient in need of said treatment which comprises administering to said patient a therapeutically effective amount of a compound of claim 14.]

[20. The method of claim 19, wherein the cancer is cancer of the breast, ovary, or colon.]

[21. A method of treating breast cancer, ovarian cancer, colon cancer, head and neck cancer, lung cancer, gynecological cancers, brain cancer, germ cell cancer, urothelial cancer, esophageal cancer, prostate cancer, bladder cancer, or pancreatic cancer in a patient in need of said treatment which comprises administering to said patient a therapeutically effective amount of a compound of claim 15.]

[22. The method of claim 21, wherein the cancer is cancer of the breast, ovary, or colon.]

[23. A method of treating breast cancer, ovarian cancer, colon cancer, head and neck cancer, lung cancer, gynecological cancers, brain cancer, germ cell cancer, urothelial cancer, esophageal cancer, prostate cancer, bladder cancer, or pancreatic cancer in a patient in need of said treatment which comprises administering to said patient a therapeutically effective amount of a compound of claim 16.]

[24. The method of claim 23, wherein the cancer is cancer of the breast, ovary, or colon.]

[25. A method of treating a cancer responsive to microtubule stabilization in a patient comprising administering to a patient in need of such treatment a therapeutically effective amount of a compound of claim 1.]

[26. A method of treating a cancer responsive to microtubule stabilization in a patient comprising administering to a patient in need of such treatment a therapeutically effective amount of a compound of claim 2.]

[27. A method of treating a cancer responsive to microtubule stabilization in a patient comprising administering to a patient in need of such treatment a therapeutically effective amount of a compound of claim 3.]

[28. A method of treating a cancer responsive to microtubule stabilization in a patient comprising administering to a patient in need of such treatment a therapeutically effective amount of a compound of claim 8.]

[29. A method of treating a cancer responsive to microtubule stabilization in a patient comprising administering to a patient in need of such treatment a therapeutically effective amount of a compound of claim 13.]

[30. A method of treating a cancer responsive to microtubule stabilization in a patient comprising administering to a patient in need of such treatment a therapeutically effective amount of a compound of claim 14.]

[31. A method of treating a cancer responsive to microtubule stabilization in a patient comprising administering to a patient in need of such treatment a therapeutically effective amount of a compound of claim 15.]

[32. A method of treating a cancer responsive to microtubule stabilization in a patient comprising administering to a patient in need of such treatment a therapeutically effective amount of a compound of claim 16.]

[33. The method of claim 4, further comprising administering one or more of an additional anti-cancer agent.]

[34. The method of claim 33, wherein the additional anti-cancer agent acts in a phase of the cell cycle other than the $G_2$-M phase.]

[35. The method of claim 34, wherein the additional anti-cancer is a thymidilate synthase inhibitor, a DNA cross linking agent, a topoisomerase I or II inhibitor, a DNA alkylating agent, a ribonuclase reductase inhibitor, a cytotoxic factor, or a growth factor inhibitor.]

[36. The method of claim 4, further comprising administering radiation therapy.]

[37. A pharmaceutical composition comprising the compound of claim 1 and a pharmaceutically acceptable vehicle or diluent.]

[38. A pharmaceutical composition comprising the compound of claim 2 and a pharmaceutically acceptable vehicle or diluent.]

[39. A pharmaceutical composition comprising the compound of claim 3 and a pharmaceutically acceptable vehicle or diluent.]

[40. A pharmaceutical composition comprising the compound of claim 8 and a pharmaceutically acceptable vehicle or diluent.]

[41. A pharmaceutical composition comprising the compound of claim 13 and a pharmaceutically acceptable vehicle or diluent.]

[42. A pharmaceutical composition comprising the compound of claim 14 and a pharmaceutically acceptable vehicle or diluent.]

[43. A pharmaceutical composition comprising the compound of claim 15 and a pharmaceutically acceptable vehicle or diluent.]

[44. A pharmaceutical composition comprising the compound of claim 16 and a pharmaceutically acceptable vehicle or diluent.]

[45. A method of treating melanoma, non-Hodgkin's lymphoma, multiple myeloma, or Karposi's sarcoma in a patient in need of said treatment which comprises administering to said patient a therapeutically effective amount of a compound of claim 1.]

[46. A method of treating melanoma, non-Hodgkin's lymphoma, multiple myeloma, or Karposi's sarcoma in a patient in need of said treatment which comprises administering to said patient a therapeutically effective amount of a compound of claim 2.]

[47. A method of treating melanoma, non-Hodgkin's lymphoma, multiple myeloma, or Karposi's sarcoma in a patient in need of said treatment which comprises administering to said patient a therapeutically effective amount of a compound of claim 3.]

[48. A method of treating melanoma, non-Hodgkin's lymphoma, multiple myeloma, or Karposi's sarcoma in a patient in need of said treatment which comprises administering to said patient a therapeutically effective amount of a compound of claim 8.]

[49. A method of treating melanoma, non-Hodgkin's lymphoma, multiple myeloma, or Karposi's sarcoma in a patient in need of said treatment which comprises administering to said patient a therapeutically effective amount of a compound of claim 13.]

[50. A method of treating melanoma, non-Hodgkin's lymphoma, multiple myeloma, or Karposi's sarcoma in a patient in need of said treatment which comprises administering to said patient a therapeutically effective amount of a compound of claim 14.]

[51. A method of treating melanoma, non-Hodgkin's lymphoma, multiple myeloma, or Karposi's sarcoma in a patient in need of said treatment which comprises administering to said patient a therapeutically effective amount of a compound of claim 15.]

[52. A method of treating melanoma, non-Hodgkin's lymphoma, multiple myeloma, or Karposi's sarcoma in a patient in need of said treatment which comprises administering to said patient a therapeutically effective amount of a compound of claim 16.]

[53. A compound of the formula:

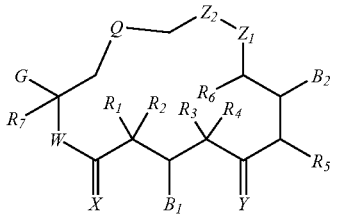

wherein:

Q is selected from the group consisting of:

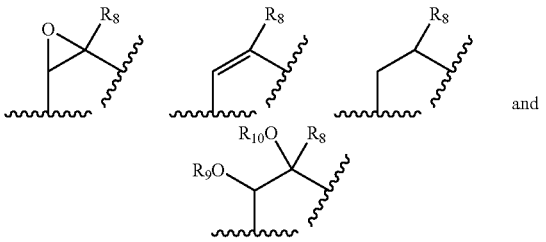

G is selected from the group consisting of alkyl; substituted alkyl; substituted aryl; a 4 to 7 membered monocyclic, 7 to 11 membered bicyclic, or 10 to 15 membered tricyclic saturated or unsaturated ring system having between 1 and 3 heteroatoms selected from nitrogen, oxygen, and sulfur;

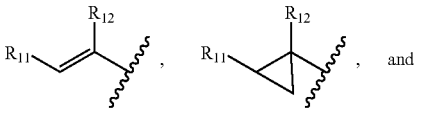

-continued

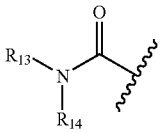

X is O or H, H;

Y is selected from the group consisting of O; H, $OR_{16}$; $OR_{17}$, $OR_{17}$; $NOR_{18}$; H, $NHOR_{19}$; H, $NR_{20}R_{21}$; H, H; and $CHR_{22}$; wherein $OR_{17}$, $OR_{17}$ can be a cyclic ketal;

$Z_1$ and $Z_2$ are independently $CH_2$;

$B_1$ and $B_2$ are independently selected from the group consisting of $OR_{24}$, $OCOR_{25}$, and O—C(═O)-$NR_{26}R_{27}$, and when $B_1$ is OH and Y is OH, H, they can form a six-membered ring ketal or acetal;

$R_1$, $R_2$, $R_3$, $R_4$, $R_5$, $R_7$, $R_{13}$, $R_{14}$, $R_{18}$, $R_{19}$, $R_{20}$, $R_{21}$, $R_{22}$, $R_{26}$ and $R_{27}$ are selected from the group consisting of H, alkyl, substituted alkyl, and aryl, and when $R_1$ and $R_2$ are alkyl can be joined to form a cycloalkyl, and when $R_3$ and $R_4$ are alkyl can be joined to form a cycloalkyl;

$R_6$ is methyl;

$R_9$, $R_{10}$, $R_{16}$, $R_{17}$, $R_{24}$, $R_{25}$ and $R_{31}$ are selected from the group consisting of H, alkyl, and substituted alkyl;

$R_{11}$, $R_{12}$, $R_{28}$, $R_{30}$, $R_{32}$, and $R_{33}$ are selected from the group consisting of H; alkyl; substituted alkyl; aryl; substituted aryl; cycloalkyl containing 1 to 3 rings and 3 to 7 carbons per ring which may be further fused with an unsaturated $C_3$–$C_7$ carbocyclic ring; and a 4 to 7 membered monocyclic, 7 to 11 membered bicyclic, or 10 to 15 membered tricyclic saturated or unsaturated ring system having between 1 and 3 heteroatoms selected from nitrogen, oxygen, and sulfur;

$R_8$ is hydrogen or methyl;

$R_{15}$, $R_{23}$ and $R_{29}$ are selected from the group consisting of H; alkyl; substituted alkyl; aryl; substituted aryl; cycloalkyl containing 1 to 3 rings and 3 to 7 carbons per ring which may be further fused with an unsaturated $C_3$–$C_7$ carbocyclic ring; a 4 to 7 membered monocyclic, 7 to 11 membered bicyclic, or 10 to 15 membered tricyclic saturated or unsaturated ring system having between 1 and 3 heteroatoms selected from nitrogen, oxygen, and sulfur; $R_{32}C$═O; $R_{33}SO_2$; hydroxy; O-alkyl or O-substituted allcyl;

or pharmaceutically acceptable salts, hydrates, solvates or geometric, optical or steroisomers thereof.]

[54. A method of treating breast cancer, ovarian cancer, colon cancer, head and neck cancer, lung cancer, gynecological cancers, brain cancer, germ cell cancer, urothelial cancer, esophageal cancer, prostate cancer, bladder cancer, or pancreatic cancer in a patient in need of said treatment which comprises administering to said patient a therapeutically effective amount of a compound of claim 53.]

[55. The method of claim 54 wherein the cancer is cancer of the breast, ovary, or colon.]

[56. A method of treating a cancer responsive to microtubule stabilization in a patient comprising administering to a patient in need of such treatment a therapeutically effective amount of a compound of claim 53.]

[57. The method of claim 54 further comprising administering one or more of an additional anti-cancer agent.]

[58. The method of claim 57 wherein the additional anti-cancer agent acts in a phase of the cell cycle other than the $G_2$-M phase.]

[59. The method of claim 58 wherein the additional anticancer is a thymidilate synthase inhibitor, a DNA cross linking agent, a topoisomerase I or II inhibitor, a DNA alkylating agent, a ribonuclease reductase inhibitor, a cytotoxic factor, or a growth factor inhibitor.]

[60. A method of treating melanoma, non-Hodgkin's lymphoma, multiple myeloma, or Karposi's sarcoma in a patient in need of said treatment which comprises administering to said patient a therapeutically effective amount of a compound of claim 53.]

[61. A pharmaceutical composition comprising the compound of claim 53 and a pharmaceutically acceptable vehicle or diluent.]

[62. A compound of the formula:

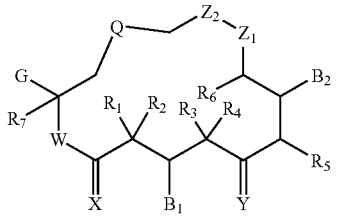

V wherein:

Q is selected from the group consisting of:

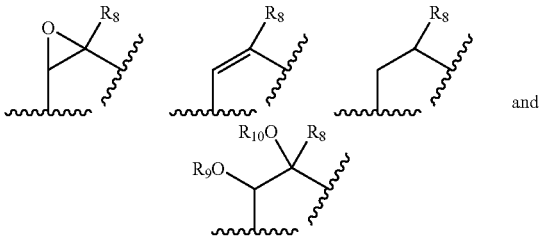

G is selected from the group consisting of alkyl; substituted alkyl; substituted aryl; a 4 to 7 membered monocyclic, 7 to 11 membered bicyclic, or 10 to 15 membered tricyclic saturated or unsaturated ring system having between 1 and 3 heteroatoms selected from nitrogen, oxygen, and sulfur;

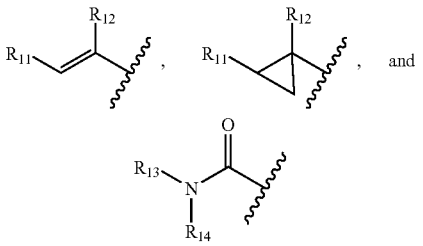

W is O or $NR_{15}$;

X is O or H, H;

Y is selected from the group consisting of O; H, $OR_{16}$; $OR_{17}$, $OR_{17}$; $NOR_{18}$; H, $NHOR_{19}$; H, $NR_{20}R_{21}$; H, H; and $CHR_{22}$; wherein $OR_{17}$, $OR_{17}$ can be a cyclic ketal;

$Z_1$ and $Z_2$ are independently $CH_2$;

$B_1$ and $B_2$ are independently selected from the group consisting of $OR_{24}$, $OCOR_{25}$, and O—C(=O)—$NR_{26}R_{27}$, and when $B_1$ is OH and Y is OH, H, they can form a six-membered ring ketal or acetal;

$R_1$, $R_2$, $R_3$, $R_4$, $R_5$, $R_7$, $R_{13}$, $R_{14}$, $R_{18}$, $R_{19}$, $R_{20}$, $R_{21}$, $R_{22}$, $R_{26}$ and $R_{27}$ are selected from the group consisting of H, alkyl, substituted alkyl, and aryl, and when $R_1$ and $R_2$ are alkyl can be joined to form a cycloalkyl, and when $R_3$ and $R_4$ are alkyl can be joined to form a cycloalkyl;

$R_6$ is methyl;

$R_9$, $R_{10}$, $R_{16}$, $R_{17}$, $R_{24}$, $R_{25}$ and $R_{31}$ are selected from the group consisting of H, alkyl, and substituted alkyl;

$R_{11}$, $R_{12}$, $R_{28}$, $R_{30}$, $R_{32}$, and $R_{33}$ are selected from the group consisting of H; alkyl; substituted alkyl; aryl; substituted aryl; cycloalkyl containing 1 to 3 rings and 3 to 7 carbons per ring which may be further fused with an unsaturated $C_3$–$C_7$ carbocyclic ring; and a 4 to 7 membered monocyclic, 7 to 11 membered bicyclic, or 10 to 15 membered tricyclic saturated or unsaturated ring system having between 1 and 3 heteroatoms selected from nitrogen, oxygen, and sulfur;

$R_8$ is hydrogen or methyl;

$R_{15}$, $R_{23}$ and $R_{29}$ are selected from the group consisting of H; alkyl; substituted alkyl; aryl; substituted aryl; cycloalkyl containing 1 to 3 rings and 3 to 7 carbons per ring which may be further fused with an unsaturated $C_3$–$C_7$ carbocyclic ring; a 4 to 7 membered monocyclic, 7 to 11 membered bicyclic, or 10 to 15 membered tricyclic saturated or unsaturated ring system having between 1 and 3 heteroatoms selected from nitrogen, oxygen, and sulfur; $R_{32}C{=}O$; $R_{33}SO_2$; hydroxy; O-alkyl or O-substituted alkyl;

or pharmaceutically acceptable salts, hydrates, solvates or geometric, optical or steroisomers thereof;

wherein substituted alkyl is an alkyl group substituted with from one to four substituents selected from the group consisting of halo; trifluoromethyl; trifluoromethoxy; hydroxy; alkoxy; cycloalkoxy; heterocyclooxy; oxo; alkanoyl; aryloxy; alkanoyloxy; amino; alkylamino; arylamine; aralkylamino; cycloalkylamino; heterocycloamino; disubstituted amines wherein the substituents are selected from alkyl, aryl, and aralkyl; alkanoylamino; optionally substituted with halogen, alkyl, alkoxy, aryl, or araralkyl; arylamino optionally substituted with halogen, alkyl, alkoxy, aryl, or araralkyl; aralkanoylamino optionally substituted with halogen, alkyl, alkoxy, aryl, or araralkyl; thio; alkylthio; aralkylthio; cycloalkylthio; heterocyclothio; alkylthiono; arylthiono; aralkylthiono; alkylsulfonyl; arylsulfonyl; aralkylsulfonyl; sulfonamido optionally substituted with halogen, alkyl, alkoxy, aryl, or araralkyl; nitro; cyano; carboxy; carbamyl optionally substituted with halogen, alkyl, alkoxy, aryl, or araralkyl; alkoxycarbonyl; aryl; substituted aryl; guanidino; and heterocyclo; and substituted aryl is an aryl group substituted with from one to four substituents selected from the group consisting of alkyl; substituted alkyl; halo; trifluoromethyl; trifluoromethoxy; hydroxy; alkoxy; cycloalkoxy; heterocyclooxy; alkanoyl; alkanoyloxy; amino; alkylamino; aralkylamino; cycloalkylamino; heterocycloamino; dialkylamino; alkanoylamino; thio; alkylthio; cycloalkylthio; heterocyclothio; ureido; nitro; cyano; carboxy; carboxyalkyl; carbamyl; alkoxycarbonyl; alkylthiono; arylthiono; alkylsulfonyl; sulfonamido; and aryloxy each of which may be optionally substituted with halo, hydroxy, alkyl, alkoxy, substituted aryl, substituted alkyl, or substituted aralkyl;

with the proviso that compounds wherein

W and X are both O; and $R_1$, $R_2$ and $R_7$ are H; and $R_3$, $R_4$ and $R_6$ are methyl; and $R_8$ is H or methyl; and G is 1-methyl-2-(substituted-4-thiazolyl)ethenyl; and Q is as defined above are excluded.]

*63. The compound of claim 96, wherein Q is*

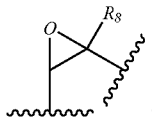

*64. A method of treating breast cancer, ovarian cancer, colon cancer, head and neck cancer, lung cancer, gynecological cancers, brain cancer, germ cell cancer, urothelial cancer, esophageal cancer, prostate cancer, bladder cancer, or pancreatic cancer in a patient in need of said treatment which comprises administering to said patient a therapeutically effective amount of a compound of claim 96.*

*65. The method of claim 64, wherein the cancer is cancer of the breast, ovary, or colon*

.

*66. A method of treating breast cancer, ovarian cancer, colon cancer, head and neck cancer, lung cancer, gynecological cancers, brain cancer, germ cell cancer, urothelial cancer, esophageal cancer, prostate cancer, bladder cancer, or pancreatic cancer in a patient in need of said treatment which comprises administering to said patient a therapeutically effective amount of a compound of claim 63*

.

*67. The method of claim 66, wherein the cancer is cancer of the breast, ovary, or colon.*

*68. A method of treating a cancer responsive to microtubule stabilization in a patient comprising administering to a patient in need of such treatment a therapeutically effective amount of a compound of claim 96.*

*69. A method of treating a cancer responsive to microtubule stabilization in a patient comprising administering to a patient in need of such treatment a therapeutically effective amount of a compound of claim 63.*

*70. A pharmaceutical composition comprising the compound of claim 96 and a pharmaceutically acceptable vehicle or diluent.*

*71. A pharmaceutical composition comprising the compound of claim 63 and a pharmaceutically acceptable vehicle or diluent.*

*72. A method of treating melanoma, non-Hodgkin's lymphoma, multiple myeloma, or Karposi's sarcoma in a patient in need of said treatment which comprises administering to said patient a therapeutically effective amount of a compound of claim 96.*

*73. A method of treating melanoma, non-Hodgkin's lymphoma, multiple myeloma, or Karposi's sarcoma in a patient in need of said treatment which comprises administering to said patient a therapeutically effective amount of a compound of claim 63.*

*74. A compound of the formula:*

V

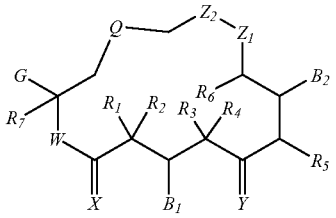

*wherein:*

*Q is selected from the group consisting of:*

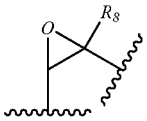

*and*

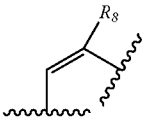

*G is selected from the group consisting of substituted aryl; a 4 to 7 membered monocyclic, 7 to 11 membered bicyclic, or 10 to 15 membered tricyclic saturated or unsaturated ring system having between 1 and 3 heteroatoms selected from nitrogen, oxygen, and sulfur; and*

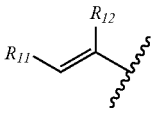

*W is O;*

*X is O or H, H;*

*Y is selected from the group consisting of O; H, $OR_{16}$; $OR_{17}$, $OR_{17}$; $NOR_{18}$; H,$NHOR_{19}$; H, $NR_{20}R_{21}$; H, H; and $CHR_{22}$; wherein $OR_{17}$, $OR_{17}$ can be a cyclic ketal;*

*$Z_1$ and $Z_2$ are independently $CH_2$;*

*$B_1$ is selected from the group consisting of $OR_{24}$, $OCOR_{25}$, and O—C(═O)—$NR_{26}R_{27}$;*

*$B_2$ is selected from the group consisting of OH, $OCOR_{25}$, and O—C(═O)—$NR_{26}R_{27}$;*

*$R_1$ and $R_2$ are both hydrogen;*

*$R_2$, $R_3$, $R_4$, $R_5$, $R_7$, $R_{13}$, $R_{14}$, $R_{18}$, $R_{19}$, $R_{20}$, $R_{21}$, $R_{22}$, $R_{26}$ and $R_{27}$ are selected from the group consisting of H, alkyl, substituted alkyl, and aryl, and when $R_1$ and $R_2$ are alkyl can be joined to form a cycloalkyl, and when $R_3$ and $R_4$ are alkyl can be joined to form a cycloalkyl; $R_6$ is methyl;*

*$R_9$, $R_{10}$, $R_{16}$, $R_{17}$, $R_{24}$, $R_{25}$ and $R_{31}$ are selected from the group consisting of H, alkyl, and substituted alkyl;*

*$R_{11}$ is selected from the group consisting of alkyl; substituted alkyl; aryl; substituted aryl; cycloalkyl containing 1 to 3 rings and 3 to 7 carbons per ring which may be further fused with an unsaturated $C_3$-$C_7$ carbocyclic ring; and a 4 to 7 membered monocyclic, 7 to 11 membered bicyclic, or 10 to 15 membered tricyclic saturated or unsaturated ring system having between 1 and 3 heteroatoms selected from nitrogen, oxygen, and sulfur;*

$R_{12}$, $R_{28}$, $R_{30}$, $R_{32}$, and $R_{33}$ are selected from the group consisting of H; alkyl; substituted alkyl; aryl; substituted aryl; cycloalkyl containing 1 to 3 rings and 3 to 7 carbons per ring which may be further fused with an unsaturated $C_3$-$C_7$ carbocyclic ring; and a 4 to 7 membered monocyclic, 7 to 11 membered bicyclic, or 10 to 15 membered tricyclic saturated or unsaturated ring system having between 1 and 3 heteroatoms selected from nitrogen, oxygen, and sulfur;

$R_8$ is hydrogen or methyl;

$R_{23}$ and $R_{29}$ are selected from the group consisting of H; alkyl; substituted alkyl; aryl; substituted aryl; cycloalkyl containing 1 to 3 rings and 3 to 7 carbons per ring which may be further fused with an unsaturated $C_3$-$C_7$ carbocyclic ring; a 4 to 7 membered monocyclic, 7 to 11 membered bicyclic, or 10 to 15 membered tricyclic saturated or unsaturated ring system having between 1 and 3 heteroatoms selected from nitrogen, oxygen, and sulfur; $R_{32}C{=}O$; $R_{33}SO_2$; hydroxy; O-alkyl or O-substituted alkyl;

or pharmaceutically acceptable hydrates or solvates thereof;

with the proviso that a compound wherein

W and X are both O; and $R_7$ is H; and $R_3$, $R_4$ and $R_6$ are methyl; and $R_8$ is H or methyl; and G is 1-methyl-2-(substituted-4-thiazolyl)ethenyl; and Q is as defined above is excluded.

75. The compound of claim 74 wherein X and Y are O.

76. A method of treating breast cancer, ovarian cancer, colon cancer, head and neck cancer, lung cancer, gynecological cancers, brain cancer, germ cell cancer, urothelial cancer, esophageal cancer, prostate cancer, bladder cancer, or pancreatic cancer in a patient in need of said treatment which comprises administering to said patient a therapeutically effective amount of a compound of claim 74.

77. The method of claim 76, wherein the cancer is cancer of the breast, ovary, or colon.

78. A method of treating breast cancer, ovarian cancer, colon cancer, head and neck cancer, lung cancer, gynecological cancers, brain cancer, germ cell cancer, urothelial cancer, esophageal cancer, prostate cancer, bladder cancer, or pancreatic cancer in a patient in need of said treatment which comprises administering to said patient a therapeutically effective amount of a compound of claim 75.

79. The method of claim 78, wherein the cancer is cancer of the breast, ovary, or colon.

80. A method of treating a cancer responsive to microtubule stabilization in a patient comprising administering to a patient in need of such treatment a therapeutically effective amount of a compound of claim 74.

81. A method of treating a cancer responsive to microtubule stabilization in a patient comprising administering to a patient in need of such treatment a therapeutically effective amount of a compound of claim 75.

82. The method of claim 76, further comprising administering one or more of an additional anti-cancer agent.

83. The method of claim 82, wherein the additional anti-cancer agent acts in a phase of the cell cycle other than the $G_2$-M phase.

84. The method of claim 83, wherein the additional anti-cancer is a thymidilate synthase inhibitor, a DNA cross linking agent, a topoisomerase I or II inhibitor, a DNA alkylating agent, a ribonuclase reductase inhibitor, a cytotoxic factor, or a growth factor inhibitor.

85. The method of claim 76, further comprising administering radiation therapy.

86. A pharmaceutical composition comprising the compound of claim 74 and a pharmaceutically acceptable vehicle or diluent.

87. A pharmaceutical composition comprising the compound of claim 75 and a pharmaceutically acceptable vehicle or diluent.

88. A method of treating melanoma, non-Hodgkin's lymphoma, multiple myeloma, or Karposi's sarcoma in a patient in need of said treatment which comprises administering to said patient a therapeutically effective amount of a compound of claim 74.

89. A method of treating melanoma, non-Hodgkin's lymphoma, multiple myeloma, or Karposi's sarcoma in a patient in need of said treatment which comprises administering to said patient a therapeutically effective amount of a compound of claim 75.

90. A compound of the formula:

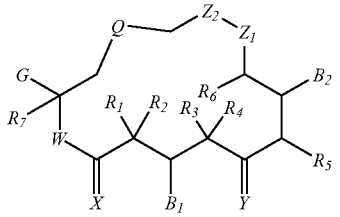

wherein:

Q is selected from the group consisting of:

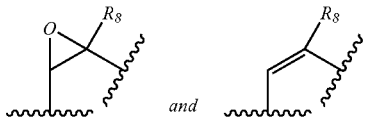

G is a 1-methyl-2-(substituted R') ethenyl group, wherein R' is a monocyclic group selected from the group consisting of pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxopyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl; or a bicyclic heterocyclic group selected from the group consisting of benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl, furo[2,3-c]pyridinyl, furo[3,1-b]pyridinyl], furo[2,3-b]pyridinyl, dihydroisoindolyl, dihydroquinazolinyl, 3,4-dihydro-4-oxo-quinazolinyl, benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, and thienothienyl; wherein the R' substituents are selected from alkyl, hydroxyalkyl, and oxo;

W is O;

X is O or H, H;

Y is selected from the group consisting of O; H, $OR_{16}$; $OR_{17}$, $OR_{17}$; $NOR_{18}$; H,$NHOR_{19}$; H, $NR_{20}R_{21}$; H, H; and $CHR_{22}$; wherein $OR_{17}$, $OR_{17}$ can be a cyclic ketal;

$Z_1$ and $Z_2$ are independently $CH_2$;

$B_1$ is selected from the group consisting of $OR_{24}$, $OCOR_{25}$, and O—C(═O)—$NR_{26}R_{27}$;

$B_2$ is selected from the group consisting of OH, $OCOR_{25}$, and O—C(═O)—$NR_{26}R_{27}$;

$R_1$ and $R_2$ are both hydrogen;

$R_3$, $R_4$, $R_5$, $R_7$, $R_{13}$, $R_{14}$, $R_{18}$, $R_{19}$, $R_{20}$, $R_{21}$, $R_{22}$, $R_{26}$ and $R_{27}$ are selected from the group consisting of H, alkyl, substituted alkyl, and aryl, and when $R_1$ and $R_2$ are alkyl can be joined to form a cycloalkyl, and when $R_3$ and $R_4$ are alkyl can be joined to form a cycloalkyl; $R_6$ is methyl;

$R_9$, $R_{10}$, $R_{16}$, $R_{17}$, $R_{24}$, $R_{25}$ and $R_{31}$ are selected from the group consisting of H, alkyl, and substituted alkyl;

$R_{28}$, $R_{30}$, $R_{32}$, and $R_{33}$ are selected from the group consisting of H; alkyl; substituted alkyl; aryl; substituted aryl; cycloalkyl containing 1 to 3 rings and 3 to 7 carbons per ring which may be further fused with an unsaturated $C_3$-$C_7$ carbocyclic ring; and a 4 to 7 membered monocyclic, 7 to 11 membered bicyclic, or 10 to 15 membered tricyclic saturated or unsaturated ring system having between 1 and 3 heteroatoms selected from nitrogen, oxygen, and sulfur;

$R_8$ is hydrogen or methyl;

$R_{23}$ and $R_{29}$ are selected from the group consisting of H; alkyl; substituted alkyl; aryl; substituted aryl; cycloalkyl containing 1 to 3 rings and 3 to 7 carbons per ring which may be further fused with an unsaturated $C_3$-$C_7$ carbocyclic ring; a 4 to 7 membered monocyclic, 7 to 11 membered bicyclic, or 10 to 15 membered tricyclic saturated or unsaturated ring system having between 1 and 3 heteroatoms selected from nitrogen, oxygen, and sulfur; $R_{32}C$═O; $R_{33}SO_2$; hydroxy; O-alkyl or O-substituted alkyl;

or pharmaceutically acceptable hydrates or solvates thereof;

wherein substituted alkyl is an alkyl group substituted with from one to four substituents selected from the group consisting of halo; trifluoromethyl; trifluoromethoxy; hydroxy; alkoxy; cycloalkoxy; heterocyclooxy; oxo; alkanoyl; aryloxy; alkanoyloxy; amino; alkylamino; arylamine; aralkylamino; cycloalkylamino; heterocycloamino; disubstituted amines wherein the substituents are selected from alkyl, aryl, and aralkyl; alkanoylamino; optionally substituted with halogen, alkyl, alkoxy, aryl, or araralkyl; arylamino optionally substituted with halogen, alkyl, alkoxy, aryl, or araralkyl; aralkanoylamino optionally substituted with halogen, alkyl, alkoxy, aryl, or araralkyl; thio; alkylthio; aralkylthio; cycloalkylthio; heterocyclothio; alkylthiono; arylthiono; aralkylthiono; alkylsulfonyl; arylsulfonyl; aralkylsulfonyl; sulfonamido optionally substituted with halogen, alkyl, alkoxy, aryl, or araralkyl; nitro; cyano; carboxy; carbamyl optionally substituted with halogen, alkyl, alkoxy, aryl, or araralkyl; alkoxycarbonyl; aryl; substituted aryl; guanidino; and heterocyclo; and substituted aryl is an aryl group substituted with from one to four substituents selected from the group consisting of alkyl; substituted alkyl; halo; trifluoromethyl; trifluoromethoxy; hydroxy; alkoxy; cycloalkoxy; heterocyclooxy; alkanoyl; alkanoyloxy; amino; alkylamino; aralkylamino; cycloalkylamino; heterocycloamino; dialkylamino; alkanoylamino; thio; alkylthio; cycloalkylthio; heterocyclothio; ureido; nitro; cyano; carboxy; carboxyalkyl; carbamyl; alkoxycarbonyl; alkylthiono; arylthiono; alkylsulfonyl; sulfonamido; and aryloxy each of which may be optionally substituted with halo, hydroxy, alkyl, alkoxy, substituted aryl, substituted alkyl, or substituted aralkyl;

with the proviso that a compound wherein

W and X are both O; and $R_7$ is H; and $R_3$, $R_4$ and $R_6$ are methyl; and $R_8$ is H or methyl; and G is 1-methyl-2-(substituted-4-thiazolyl)ethenyl; and Q is as defined above, is excluded.

91. The compound of claim 90, wherein G is a 1-methyl-2-(substituted-4-thiazolyl) ethenyl group.

92. The compound of claim 91, wherein G is a 1-methyl-2-(2-methyl-4-thiazolyl) ethenyl group.

93. The compound of claim 90, wherein G is a 1-methyl-2-(alkyl oxazolyl) ethenyl group.

94. The compound of claim 94, wherein G is a 1-methyl-2-(methyl oxazolyl) ethenyl group.

95. A compound of the formula:

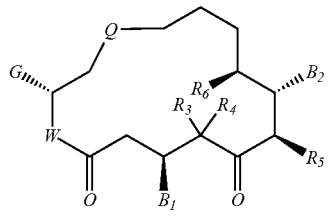

wherein

Q is

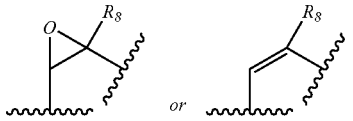

G is 1-methyl-2-(substituted-4-thiazolyl) ethenyl group;

W is O;

$B_1$ is selected from the group consisting of $OR_{24}$, $OCOR_{25}$, and O—C(═O)—$NR_{26}R_{27}$; and $B_2$ is selected from the group consisting of OH, $OCOR_{25}$, and O-C(═O)—$NR_{26}R_{27}$;

$R_3$, $R_4$, $R_5$, $R_{26}$, and $R_{27}$ are selected from the group consisting of H, alkyl, substituted alkyl, and aryl;

$R_6$ is methyl;

$R_8$ is hydrogen or methyl;

$R_{24}$ and $R_{25}$ selected from the group consisting of H, alkyl, and substituted alkyl;

or pharmaceutically acceptable hydrates and solvates thereof;

*with the proviso that compounds wherein*

*$R_3$ and $R_4$ are methyl; and*

*Q is as defined above,*

*are excluded.*

*96. A compound according to claim 95, wherein the substituents for the substituted 4-thiazolyl group of G are selected from alkyl, hydroxyalkyl, and oxo.*

* * * * *

UNITED STATES PATENT AND TRADEMARK OFFICE

CERTIFICATE OF CORRECTION

PATENT NO. : RE41,895 E
APPLICATION NO. : 12/539496
DATED : October 26, 2010
INVENTOR(S) : Gregory D. Vite et al.

It is certified that error appears in the above-identified patent and that said Letters Patent is hereby corrected as shown below:

In the Specification:

Column 1, line 9, change "*2009;*" to -- *2009,* --.

Column 1, line 11, change "*application*);" to -- *application*), --.

Column 1, line 17, change "FIELD OF THE INVENTION" to -- CROSS-REFERENCE TO RELATED APPLICATIONS --.

Column 1, line 22, below "524, filed Dec. 4, 1997.", insert

-- FIELD OF THE INVENTION --.

In the Claims:

Claim 72:

Column 59, line 61, change "*Karposi's*" to -- *Kaposi's* --.

Claim 73:

Column 59, line 66, change "*Karposi's*" to -- *Kaposi's* --.

Claim 74:

Column 60, line 42, change "$H,NHOR_{19}$" to -- $H, NHOR_{19}$ --.

Column 60, line 51, before "$R_3$," delete "$R_2$,".

Claim 84:

Column 61, line 62, change "*thymidilate*" to -- *thymidylate* --.

Column 61, line 64, change "*ribonuclase*" to -- *ribonuclease* --.

Claim 88:

Column 62, line 8, change "*Karposi's*" to -- *Kaposi's* --.

Claim 89:

Column 62, line 13, change "*Karposi's*" to -- *Kaposi's* --.

Signed and Sealed this
Thirteenth Day of December, 2011

David J. Kappos

David J. Kappos
*Director of the United States Patent and Trademark Office*

Claim 90:

Column 62, line 47, change "*4-piperidonyl*" to -- *piperidinyl* --.

Column 62, line 62, change "*pyridinyl*]" to -- *pyridinyl* --.

Column 63, line 11, change "$H,NHOR_{19}$" to -- $H, NHOR_{19}$ --.

Column 63, line 59, change "*araralkyl*" to -- *aralkyl* --.

Column 63, line 61, change "*araralkyl*" to -- *aralkyl* --.

Column 64, line 23, change "*above,*" to -- *above* --.

UNITED STATES PATENT AND TRADEMARK OFFICE
Certificate

Patent No. RE. 41,895 E

Patented: October 26, 2010

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Gregory D. Vite, Titusville, NJ (US); Soong-Hoon Kim, Lawrenceville, NJ (US); Robert M. Borzilleri, Lawrenceville, NJ (US); James A. Johnson, Lawrenceville, NJ (US); Florenz Sasse, Braunschweig (DE); and Gerhard Hofle, Braunschweig (DE).

Signed and Sealed this Twenty-sixth Day of February 2013.

ANDREW D. KOSAR
*Supervisory Patent Examiner*
Art Unit 1622
Technology Center 1600